United States Patent [19]
Myers et al.

[11] Patent Number: 6,090,576
[45] Date of Patent: Jul. 18, 2000

[54] DNA ENCODING A TRANSFERRIN RECEPTOR OF MORAXELLA

[75] Inventors: Lisa E. Myers, Guelph; Anthony B. Schryvers, Calgary; Robin E. Harkness, Willowdale; Sheena M. Loosmore, Aurora; Run-Pan Du, Thornhill; Yan-Ping Yang; Michel H. Klein, both of Willowdale, all of Canada

[73] Assignee: Connaught Laboratories Limited, North York, Canada

[21] Appl. No.: 08/613,009

[22] Filed: Mar. 8, 1996

[51] Int. Cl.⁷ .......................... C12N 15/31; C12N 15/63; C12N 1/21; C12N 5/10

[52] U.S. Cl. .................. 435/69.1; 435/71.1; 435/325; 435/252.3; 435/320.1; 536/23.1; 536/23.7; 536/24.3

[58] Field of Search ................. 536/23.7, 23.1, 536/24.3; 435/69.1, 6, 7.2, 320.1, 252.3, 252.1, 325, 71.1; 530/350; 514/2

[56] References Cited

U.S. PATENT DOCUMENTS 5,292,869  3/1994  Schryvers ................................ 530/413

FOREIGN PATENT DOCUMENTS

WO 90/12591  11/1990  WIPO.
WO 93/08283  4/1993  WIPO.
WO 95/33049  12/1995  WIPO.
WO 97/13785  4/1997  WIPO.

OTHER PUBLICATIONS

Yu et al. (1993) Micro Bial. Pathogenesis 15:433–445.
Gerla CH et al. (1992) Infection and Immunity 60:3253–3261.
Anderson et al. (1994) J. Bacteriology 176:3162–3170.
Gray–Owen et al. (1995) Infection and Immunity 63:1201–1210.
Bowie et al. (1990) Science 247:1306–1310.
Regenmortel (1986) TIBS 11:36–39.
George et al. (1988) Macromolecular Sequencing and Synthesis (Ed. by D.H. Schlesinger) Alan R. Liss, Inc., New York, pp. 127–149.
Raong–Hua Yu et al; Microbial Pathogenesis, vol. 15, 1993, pp. 433–445 XP000612196.
Brorson, J–E., A. Axelsson, and S.E. Holm. 1976. Studies on *Branhamella catarrhalis* (*Neisseria catarrhalis*) with special reference to maxillary sinusitis. Scan. J. Infect. Dis. 8:151–155.
Catlin, B.W., 1990, *Branhamella catarrhalis*: an organism gaining respect as a pathogen. Clin. Microbiol. Rev. 3:293–320.
Hager, H., A. Verghese, S. Alvarez, and S.L. Berk. 1987. *Branhamella catarrhalis* respiratory infections. Rev. Infect. Dis. 9:1140–1149.

McLeod, D.T., F. Ahmad, M.J. Croughan, and M.A. Calder. 1986. Bronchopulmonary infection due to *M. catarrhalis*. Clinical features and therapeutic response. Drugs 31(Suppl.3):109–112.
Nicotra, B., M. Rivera, J.I. Luman, and R.J. Wallace. 1986. *Branhamella catarrhalis* as a lower respiratory tract pathogen in patients with chronic lung disease. Arch.Intern.Med. 146:890–893.
Ninane, G., J. Joly, and M. Kraytman. 1978. Bronchopulmonary infection due to *Branhamella catarrhalis* 11 cases assessed by transtracheal puncture. Br.Med.Jr. 1:276–278.
Srinivasan, G., M.J. Raff, W.C. Templeton, S.J. Givens, R.C. Graves, and J.C. Mel. 1981. *Branhamella catarrhalis* pneumonia. Report of two cases and review of the literature. Am.Rev. Respir. Dis. 123:553–555.
West, M., S.L. Berk, and J.K. Smith. 1982. *Branhamella catarrhalis* pneumonia. South.Med. J. 75:1021–1023.
Christensen, J.J., and B. Bruun, 1985. Bacteremia caused by a beta–lactamase producing strain of *Branhamella catarrhalis*. Acta.Pathol. Microbiol. Immunol. Scand. Sect.B 93:273–275.
Craig, D.B., and P.A. Wehrle, 1983. *Branhamella catarrhalis* septic arthritis. J. Rheumatol. 10:985–986.
Guthrie, R., K. Bakenhaster, R.Nelson, and R. Woskobnick. 1988. *Branhamella catarrhalis* sepsis: a case report and review of the literature. J.Infect.Dis. 158:907–908.
Hiroshi, S., E.J. Anaissie, N.Khardori, and G.P. Bodey. 1988. *Branhamella catarrhalis* septicemia in patients Cancer 61:2315–2317.
O'Neill, J.H., and P.W. Mathieson, 1987. Meningitis due to *Branhamella catarrhalis*. Aust. N.Z. J. Med. 17:241–242.
Murphy, T.F. 1989. The surface of *Branhamella catarrhalis*: a systematic approach to the surface antigens of an emerging pathogen. Pediatr. Infect. Dis. J. 8:S75–S77.
Van Hare, G.F., P.A. Shurin, C.D. Marchant, N.A. Cartelli, C.E.Johnson, D. Fulton, S. Carlin, and C.H. Kim. Acute otitis media caused by *Branhamella catarrhalis*: biology and therapy. Rev. Infect. Dis. 9:16–27.
Jorgensen, J.H., Doem, G.V., Maher, L.A., Howell, A.W., and Redding, J.S., 1990 Antimicrobial resistance among respiratory isolates of *Haemophilus influenza, Moraxella catarrhalis*, and Streptococcus pneumoniae in the United States. Antibicrob. Agents Chemother. 34: 2075–2080.
Schryvers, A.B. and Morris, L.J. 1988 Identification and Characterization of the transferrin receptor from *Neisseria meningitidis*. Mol. Microbiol. 2:281–288.

(List continued on next page.)

*Primary Examiner*—Paula K. Hutzell
*Assistant Examiner*—Michael Pak
*Attorney, Agent, or Firm*—Sim & McBurney

[57] ABSTRACT

Purified and isolated nucleic acid molecules are provided which encode transferrin receptor proteins of Moraxella, such as *M. catarrhalis* or a fragment or an analog of the transferrin receptor protein. The nucleic acid sequence may be used to produce recombinant transferrin receptor proteins Tbp1 and Tbp2 of the strain of Moraxella free of other proteins of the Moraxella strain for purposes of diagnostics and medical treatment. Furthermore, the nucleic acid molecule may be used in the diagnosis of infection.

11 Claims, 57 Drawing Sheets

OTHER PUBLICATIONS

Lee, B.C., Schryvers, A.B. Specificity of the lactoferrin and transferrin receptors in *Neisseria gonorrhoeae*. Mol. Microbiol. 1988; 2–827–9.

Schryvers, A.B. Characterization of the human transferrin and lactoferrin receptors in *Haemophilus influenzae*. Mol. Microbiol. 1988; 2: 467–72.

Schryvers, A.B. and Lee, B.C. (1988) Comparative analysis of the transferrin and lactoferrin binding proteins in the family Neisseriaceae. Can. J. Microbiol. 35, 409–415.

Yu, R. and Schryvers, A.B., 1993. The interaction between human tranferrin and transferrin binding protein 2 from *Moraxella* (*Branhamella*) *catarrhalis* differs from that of other human pathogens. Microbiol. Pathogenesis, 15:433–445.

O'Hagan, 1992. Clin. Pharmokinet. 22:1.

Ulmer et al., 1993. Curr. Opinion Invest. Drugs 2: 983–989.

Lockhoff, O., 1991. Glycolipds as immunomoclutators: Synthesis and properits. Chem. Int. Ed. Engl. 30: 1611–1620.

Nixon–George, 1990. J. Immunol. 14: 4798–4802.

Wallace, R.J. Jr., Nash, D.R., and Steingrube, V.A. 1990. Antibiotic susceptibilites and drug resistance in *Moraxella* (*Branhaemella*) *catarrhalis*. Am. J. Med. 88 (5A): 465–50S.

F.M. Ausubel et al., Short protocols in Molecular Biology, Greene Publishing Associates and John Wiley and Sons.

Schryvers, A.B., Lee, B.C. 1989. Comparative analysis of the transferrin and lactoferrin binding proteins in the family Neisseriaceae. Can. J. Microbiol. 35: 409–415.

Legrain, M., V. Mazarin, S.W. Irwin, B. Bouchon, M–J. Quentin–Millet, E. Jacobs, and A.B. Schryvers. 1993. Cloning and characterization of Neisseria meningitidis genes encoding the transferrin–binding proteins Tbp1 and Tbp2. Gene 130: 73–80.

Ogunnariwo, J.W., Woo, T.K.W., Lo, R.Y.C., Gonzalez, G.C., and Schryvers, A.B. Characterization of the Pasteurella haemolytica transferrin receptor genes and the recombinant receptor proteins. Microb. Pathog. 23:273–284 (1997).

Yang, Y.P., Myers, L.E., McGuinness, U., Chong, P., Kwok, Y., Klein, M.H. and Harkness, R.E. The major outer membrane protein, C.D, extracted from Moraxella (Branhamella) catarrhalis is a potential vaccine antigen that induces bactericidal antibodies. FEMS Immun. Med. Microbiol. 17:187–199 (1997).

Needleman, S.B., and Wunsch, C.D. 1970, J. Mol Biol. 48:443–453.

Sellers, P.J. 1974 On the theory and computation of evolutionary distances. J. Appl. Math (Siam) 26:787–793.

Waterman, M.S., Smith, T.F., and Beyer, W.A. 1976. Advan. Math. 20:367–387.

Gerlach et al (1992) Infection and Immunity 60: 3253–3261.

Anderson et al (1994) J. Bacteriology 176: 3162–3170.

Gray–Owen et al (1995) Infection and Immunity 63: 1201–1210.

Bowie et al (1990) Science 247: 1306–1310.

Regenmortel (1986) TIBS 11: 36–39.

George et al (1988) Macromolecular Sequencing and Synthesis (Ed. By D. H. Schlesinger) Alan R. Liss, Inc., New York, pp. 127–129.

Smith, T.F., and Waterman, M.S. 1981 Identification of common molecular subsequences. J. Mol. Biol. 147:195–197.

Jimenez–Montano, M. and Zamora–Cortina, L. 1981 Evolutionary model for the generation of amino acid sequences and its application to the study of mammal alpha–hemoglobin chains. Proc. VII Int. Biophysics Congress, Mexico City.

Sobel, E. And Martinez, H.M. 1985 A Multiple Sequence Alignment Program. Nucleic Acid Res. 14:363–374.

Rong–Hua Yu et al; Microbial Pathogenesis, vol. 15, 1993, pp. 433–445 XP000612196.

AMINO ACID SEQUENCES OF A CONSERVED PORTION OF Tbp1 PROTEIN FOR CONSTRUCTION OF DEGENERATE PRIMERS USED IN PCR AMPLIFICATION OF A PORTION OF THE *M. cattarhalis* 4223 *tbpA* GENE.

| | |
|---|---|
| N E V T G L G | SEQ ID NO: 13 |
| G A I N E I E | SEQ ID NO: 14 |

Sequence of M. catarrhalis 4223 tbpA gene

```
TATTTGACAAGCTATACACTAAAATCAAAATTAATCACTTTGGTTGGTGTTTAGCAAGCAAATGGT

TATTTGGTAAACAATTAAGTTCTTAAAAACGATACACGCTCATAAACAGATGGTTTTGGCATCTGCAAT

TTGATGCCTGCCCTTGTGATTGGTTGGGGTGTGTATCGGTGTATCAAAGTGCAAAAGCCAACAGGTGGTCATTG
                                                                    54
ATG AAT CAA TCA AAA CAA AAC AAC AAA TCC AAA AAA CAA GTA TTA AAA
MET Asn Gln Ser Lys Gln Asn Asn Lys Ser Lys Lys Gln Val Leu Lys
                 27                        81                      108
CTT AGT GCC TTG TCT TTG GGT CTG CTT AAC ATC ACG CAG GTG GCA CTG GCA AAC
Leu Ser Ala Leu Ser Leu Gly Leu Leu Asn Ile Thr Gln Val Ala Leu Ala Asn
                                        135                         162
ACA ACG GCC GAT AAG GCG GAG GCA ACA GAT AAG ACA AAC CTT GTT GTC TTG
Thr Thr Ala Asp Lys Ala Glu Ala Thr Asp Lys Thr Asn Leu Val Val Leu
                                189                                 216
GAT GAA ACT GTT GTA ACA GCG AAG AAA AAC GCC CGT AAA GCC AAC GAA GTT ACA
Asp Glu Thr Val Val Thr Ala Lys Lys Asn Ala Arg Lys Ala Asn Glu Val Thr
```

FIG.5B

```
                                                                          243
GGG CTT GGT AAG GTG GTC AAA ACT GCC GAG ACC ATC AAT AAA GAA CAA GTG CTA
Gly Leu Gly Lys Val Val Lys Thr Ala Glu Thr Ile Asn Lys Glu Gln Val Leu
                                                                          270

297
AAC ATT CGA GAC TTA ACA CGC TAT GAC CCT GGC ATT GCT GTG GTT GAG CAA GGT
Asn Ile Arg Asp Leu Thr Arg Tyr Asp Pro Gly Ile Ala Val Val Glu Gln Gly
                                                                          324

351
CGT GGG GCA AGC TCA GGC TAT TCT ATT CGT GGT ATG GAT AAA AAT CGT GTG GCG
Arg Gly Ala Ser Ser Gly Tyr Ser Ile Arg Gly MET Asp Lys Asn Arg Val Ala
                                                                          378

405
GTA TTG GTT GAT GGC ATC AAT CAA GCC CAG CAC TAT GCC CTA CAA GGC CCT GTG
Val Leu Val Asp Gly Ile Asn Gln Ala Gln His Tyr Ala Leu Gln Gly Pro Val
                                                                          432

459
GCA GGC AAA AAT TAT GCC GCA GGT GGG GCA ATC AAC GAA ATA GAA TAC GAA AAT
Ala Gly Lys Asn Tyr Ala Ala Gly Gly Ala Ile Asn Glu Ile Glu Tyr Glu Asn
                                                                          486

513
GTC CGC TCC GTT GAG ATT AGT AAA GGT GCA AAT TCA AGT GAA TAC GGC TCT GGG
Val Arg Ser Val Glu Ile Ser Lys Gly Ala Asn Ser Ser Glu Tyr Gly Ser Gly
                                                                          540
```

FIG.5C

```
GCA TTA TCT GGC TCT GTG GCA TTT ACC AAA ACC GCC GAT GAC ATC ATC AAA    594
Ala Leu Ser Gly Ser Val Ala Phe Thr Lys Thr Ala Asp Asp Ile Ile Lys
                                567

GAT GGT AAA GAT TGG GGC GTG CAG ACC AAA ACC GCC TAT GCC AGT AAA AAT AAC    648
Asp Gly Lys Asp Trp Gly Val Gln Thr Lys Thr Ala Tyr Ala Ser Lys Asn Asn
                        621

GCA TGG GTT AAT TCT GTG GCA GCA GCA GGA AAG GCA GGT TCT TTT AGC GGT CTT    702
Ala Trp Val Asn Ser Val Ala Ala Ala Gly Lys Ala Gly Ser Phe Ser Gly Leu
                                675

ATC ATC TAC ACC GAC CGC CGT GGT CAA GAA TAC AAG GCA CAT GAT GAT GCC TAT    756
Ile Ile Tyr Thr Asp Arg Arg Gly Gln Glu Tyr Lys Ala His Asp Asp Ala Tyr
                                729

CAG GGT AGC CAA AGT TTT GAT AGA GCG GTG GCA ACT GAC ACC AAT AAC CGA    810
Gln Gly Ser Gln Ser Phe Asp Arg Ala Val Ala Thr Asp Thr Asn Asn Arg
                        783

ACA TTT TTA ATA GCA AAT GAA TGT GCC AAT GGT AAT TAT GAG TAT GCT GCT    864
Thr Phe Leu Ile Ala Asn Glu Cys Ala Asn Gly Asn Tyr Glu Tyr Ala Ala
                                837

GGC GGT CAA ACC AAA CTT CAA GCC AAG CCA ACC AAT GTG CGT GAT AAG GTC AAT    918
Gly Gly Gln Thr Lys Leu Gln Ala Lys Pro Thr Asn Val Arg Asp Lys Val Asn
                        891
```

FIG.5D

```
GTC AAA GAT TAT ACA GGT CCT AAC CGC CTT ATC CCA AAC CTC ACC CAA GAC
Val Lys Asp Tyr Thr Gly Pro Asn Arg Leu Ile Pro Asn Leu Thr Gln Asp
                        945                                      972

AGC AAA TCC TTA CTG CTT CGC CCA GGT TAT CAG CTA AAC GAT AAG CAC TAT GTC
Ser Lys Ser Leu Leu Leu Arg Pro Gly Tyr Gln Leu Asn Asp Lys His Tyr Val
                        999                                     1026

GGT GGT GTG TAT GAA ATC ACC AAA CAA TAC GCC ATG CAA GAT AAA ACC GTG
Gly Gly Val Tyr Glu Ile Thr Lys Gln Asn Tyr Ala MET Gln Asp Lys Thr Val
                       1053                                     1080

CCT GCT TAT CTG ACG GTT CAT GAC ATT GAA AAA TCA AGG CTC AGC AAC CAT GCC
Pro Ala Tyr Leu Thr Val His Asp Ile Glu Lys Ser Arg Leu Ser Asn His Ala
                       1107                                     1134

CAA GCC AAT GGC TAT TAT CAA AAT AAT CTT GGT GAA CGC ATT CGT GAT ACC
Gln Ala Asn Gly Tyr Tyr Gln Asn Asn Leu Gly Glu Arg Ile Arg Asp Thr
                       1161                                     1188

ATT GGG CCA GAT TCA GGT TAT GGC ATC AAC TAT GCT CAT GGC GTA TTT TAT GAT
Ile Gly Pro Asp Ser Gly Tyr Gly Ile Asn Tyr Ala His Gly Val Phe Tyr Asp
                       1215                                     1242
```

FIG.5E

```
GAA AAA CAC CAA AAA GAC CGC CTA GGG CTT GAA TAT GTT TAT GAC AGC AAA GGT
Glu Lys His Gln Lys Asp Arg Leu Gly Leu Glu Tyr Val Tyr Asp Ser Lys Gly
                1269                                                1296

GAA AAT AAA TGG TTT GAT GAT GTG CGT GTG TCT TAT GAT AAG CAA GAC ATT ACG
Glu Asn Lys Trp Phe Asp Asp Val Arg Val Ser Tyr Asp Lys Gln Asp Ile Thr
                1323                                                1350

CTA CGC AGC CAG CTG ACC AAC ACG CAC TGT TCA ACC TAT CCG CAC ATT GAC AAA
Leu Arg Ser Gln Leu Thr Asn Thr His Cys Ser Thr Tyr Pro His Ile Asp Lys
                1377                                                1404

AAT TGT ACG CCT GAT GTC AAT CCT TTT TCG GTA AAA GAG GTG GAT AAC AAT
Asn Cys Thr Pro Asp Val Asn Lys Pro Phe Ser Val Lys Glu Val Asp Asn Asn
                1431                                                1458

GCC TAC AAA GAA CAG CAC CAT AAT TTA ATC AAA GCC GTC TTT AAC AAA ATG GCG
Ala Tyr Lys Glu Gln His His Asn Leu Ile Lys Ala Val Phe Asn Lys MET Ala
                1485                                                1512

TTG GGC AGT ACG CAT CAC ATC AAC CTG CAA GTT GGC TAT GAT AAA TTC AAT
Leu Gly Ser Thr His His Ile Asn Leu Gln Val Gly Tyr Asp Lys Phe Asn
                1539                                                1566

TCA AGC CTG AGC CGT GAA GAT TAT CGT TTG GCA ACC CAT CAG TCT TAT CAA AAA
Ser Ser Leu Ser Arg Glu Asp Tyr Arg Leu Ala Thr His Gln Ser Tyr Gln Lys
                1593                                                1620
```

FIG.5F

```
CTT GAT TAC ACC CCA CCA AGT AAC CCT TTG CCA GAT AAG TTT AAG CCC ATT TTA
Leu Asp Tyr Thr Pro Pro Ser Asn Pro Leu Pro Asp Lys Phe Lys Pro Ile Leu
                1647                                                1674

GGT TCA AAC AAC AAA CCC ATT TGC CTT GAT GCT TAT GGT TAT CAT GAC CAT
Gly Ser Asn Asn Lys Pro Ile Cys Leu Asp Ala Tyr Gly Tyr His Asp His
            1701                                                1728

CCA CAG GCT TGT AAC GCC AAA AAC ACT TAT CAA AAT TTT GCC ATC AAA AAA
Pro Gln Ala Cys Asn Ala Lys Asn Thr Tyr Gln Asn Phe Ala Ile Lys Lys
        1755                                                    1782

GGC ATA GAG CAA TAC AAC CAA AAA ACC AAT ACC GAT AAG ATT GAT TAT CAA GCC
Gly Ile Glu Gln Tyr Asn Gln Lys Thr Asn Thr Asp Lys Ile Asp Tyr Gln Ala
    1809                                                            1836

ATT GAC CAA TAT GAT AAA CAA AAC CCC AAC AGC ACC CTA AAA CCC TTT GAG
Ile Asp Gln Tyr Asp Lys Gln Asn Pro Asn Ser Thr Leu Lys Pro Phe Glu
1863                                                        1890

AAA ATC AAA CAA AGT TTG GGG CAA GAA AAA TAC AAC AAG ATA GAC GAA CTT GGC
Lys Ile Lys Gln Ser Leu Gly Gln Glu Lys Tyr Asn Lys Ile Asp Glu Leu Gly
        1917                                                        1944
```

FIG.5G

```
                                                                      1971                                                                    1998
TTT AAA GCT TAT AAA GAT TTA CGC AAC GAA TGG GCG GGT TGG ACT AAT GAC AAC
Phe Lys Ala Tyr Lys Asp Leu Arg Asn Glu Trp Ala Gly Trp Thr Asn Asp Asn 2025                                                                    2052
AGC CAA CAA AAT GCC AAT AAA GGC ACG GAT AAT ATC TAT CAG CCA AAT CAA GCA
Ser Gln Gln Asn Ala Asn Lys Gly Thr Asp Asn Ile Tyr Gln Pro Asn Gln Ala 2079                                                                    2106
ACT GTG GTC AAA GAT GAC AAA TGT AAA TAT AGC GAG ACC AAC AGC TAT GCT GAT
Thr Val Val Lys Asp Asp Lys Cys Lys Tyr Ser Glu Thr Asn Ser Tyr Ala Asp 2133                                                                    2160
TGC TCA ACC ACT CGC CAC ATC AGT GGT GAT AAT TAT TTC ATC GCT TTA AAA GAC
Cys Ser Thr Thr Arg His Ile Ser Gly Asp Asn Tyr Phe Ile Ala Leu Lys Asp 2187                                                                    2214
AAC ATG ACC ATC AAT AAA TAT GTT GAT TTG GGG CTG GGT GCT CGC TAT GAC AGA
Asn MET Thr Ile Asn Lys Tyr Val Asp Leu Gly Leu Gly Ala Arg Tyr Asp Arg 2241                                                                    2268
ATC AAA CAC AAA TCT GAT GTG CCT TTG GTA GAC AAC AGT GCC AGC AAC CAG CTG
Ile Lys His Lys Ser Asp Val Pro Leu Val Asp Asn Ser Ala Ser Asn Gln Leu
```

FIG.5H

```
                                                                        2322
TCT TGG AAT TTT GGC GTG GTC GTC AAG CCC ACC AAT TGG CTG GAC ATC GCT TAT
Ser Trp Asn Phe Gly Val Val Val Lys Pro Thr Asn Trp Leu Asp Ile Ala Tyr
            2295
                                                                        2376
AGA AGC TCG CAA GGC TTT CGC ATG CCA AGT TTT TCT GAA ATG TAT GGC GAA CGC
Arg Ser Ser Gln Gly Phe Arg MET Pro Ser Phe Ser Glu MET Tyr Gly Glu Arg
            2349
                                                                        2430
TTT GGC GTA ACC ATC GGT AAA GGC ACG CAA CAT GGC TGT AAG GGT CTT TAT TAC
Phe Gly Val Thr Ile Gly Lys Gly Thr Gln His Gly Cys Lys Gly Leu Tyr Tyr
            2403
                                                                        2484
ATT TGT CAG CAG ACT GTC CAT CAA AAG CTA ACC AAA CCT GAA AAA TCC TTT AAC
Ile Cys Gln Gln Thr Val His Gln Lys Leu Thr Lys Pro Glu Lys Ser Phe Asn
            2457
                                                                        2538
CAA GAA ATC GGA GCG ACT TTA CAT AAC CAC TTA GGC AGT CTT GAG GTT AGT TAT
Gln Glu Ile Gly Ala Thr Leu His Asn His Leu Gly Ser Leu Glu Val Ser Tyr
            2511
                                                                        2592
TTT AAA AAT CGC TAT ACC GAT TTG ATT GTT GGT AAA AGT GAA GAG ATT AGA ACC
Phe Lys Asn Arg Tyr Thr Asp Leu Ile Val Gly Lys Ser Glu Glu Ile Arg Thr
            2565
                                                                        2646
CTA ACC CAA GGT GAT AAT GCA GGC AAA CAG CGT GGT AAA GGT GAT TTG GGC TTT
Leu Thr Gln Gly Asp Asn Ala Gly Lys Gln Arg Gly Lys Gly Asp Leu Gly Phe
            2619
```

FIG.5I

```
CAT AAT GGA CAA GAT GCT GAT TTG ACA GGC ATT AAC ATT CTT GGC AGA CTT GAC
His Asn Gly Gln Asp Ala Asp Leu Thr Gly Ile Asn Ile Leu Gly Arg Leu Asp
                2673                                                    2700

CTA AAC GCT GTC AAT AGT CGC CTT CCC TAT GGA TTA TAC TCA ACA CTG GCT TAT
Leu Asn Ala Val Asn Ser Arg Leu Pro Tyr Gly Leu Tyr Ser Thr Leu Ala Tyr
                2727                                                    2754

AAC AAA GTT GAT GTT AAA GGA AAA ACC TTA AAC CCA ACT TTG GCA GGA ACA AAC
Asn Lys Val Asp Val Lys Gly Lys Thr Leu Asn Pro Thr Leu Ala Gly Thr Asn
                2781                                                    2808

ATA CTG TTT GAT GCC ATC CAG CCA TCT CGT TAT GTG GGG CTT GGC TAT GAT
Ile Leu Phe Asp Ala Ile Gln Pro Ser Arg Tyr Val Val Gly Leu Gly Tyr Asp
                2835                                                    2862

GCC CCA AGC CAA AAA TGG GGA GCA AAC GCC ATA TTT ACC CAT TCT GAT GCC AAA
Ala Pro Ser Gln Lys Trp Gly Ala Asn Ala Ile Phe Thr His Ser Asp Ala Lys
                2889                                                    2916

AAT CCA AGC GAG CTT TTG GCA GAT AAG AAC TTA GGT AAT GGC AAC ATT CAA ACA
Asn Pro Ser Glu Leu Leu Ala Asp Lys Asn Leu Gly Asn Gly Asn Ile Gln Thr
                2943                                                    2970
```

FIG.5J

```
AAA CAA GCC ACC AAA GCA AAA TCC ACG CCG TGG CAA ACA CTT GAT TTG TCA GGT
Lys Gln Ala Thr Lys Ala Lys Ser Thr Pro Trp Gln Thr Leu Asp Leu Ser Gly
                      2997                                          3024

TAT GTA AAC ATA AAA GAT AAT TTT ACC TTG CGT GCT GGC GTG TAC AAT GTA TTT
Tyr Val Asn Ile Lys Asp Asn Phe Thr Leu Arg Ala Gly Val Tyr Asn Val Phe
                      3051                                          3078

AAT ACC TAT TAC ACC ACT TGG GAG GCT TTA CGC CAA ACA GCA GAA GGG GCG GTC
Asn Thr Tyr Tyr Thr Thr Trp Glu Ala Leu Arg Gln Thr Ala Glu Gly Ala Val
                      3105                                          3132

AAT CAG CAT ACA GGA CTG AGC CAA GAT AAG CAT TAT GGT CGC TAT GCC GCT CCT
Asn Gln His Thr Gly Leu Ser Gln Asp Lys His Tyr Gly Arg Tyr Ala Ala Pro
                      3159                                          3186

GGA CGC AAT TAC CAA TTG GCA CTT GAA ATG AAG TTT TAA
Gly Arg Asn Tyr Gln Leu Ala Leu Glu MET Lys Phe
                      3213
```

FIG.6A

Sequence of M. catarrhalis 4223 tbpB gene

```
GTAAATTGCCGTATTTGTCTATCATAAATGCATTTATCAAATGCTCAAATAAATACGCCAAATGCACAT

TGTCAGCATGCCAAAATAGGCATCAACAGACTTTTTAGATAATACCATCAACCCATCAGAGATTATTT
```

```
                                                                                       54
ATG AAA CAC ATT CCT TTA ACC ACA CTG TGT GTG GCA ATC TCT GCC GTC TTA TTA
MET Lys His Ile Pro Leu Thr Thr Leu Cys Val Val Ala Ile Ser Ala Val Leu Leu

108
ACC GCT TGT GGT GGC AGT GGT GGT TCA AAT CCA CCT CCT GCT CCT ACG CCC ATT CCA
Thr Ala Cys Gly Gly Ser Gly Gly Ser Asn Pro Pro Pro Ala Pro Thr Pro Ile Pro

162
AAT GCT AGC GGT TCA GGT AAT ACT GGC AAC ACT GGT AAT GCT GGC GGT ACT GAT
Asn Ala Ser Gly Ser Gly Asn Thr Gly Asn Thr Gly Asn Ala Gly Gly Thr Asp

216
AAT ACA GCC AAT GCA GGT AAT ACA GGC GGT ACA AAC TCT GGT ACA GGC AGT GCC
Asn Thr Ala Asn Ala Gly Asn Thr Gly Gly Thr Asn Ser Gly Thr Gly Ser Ala

270
AAC ACA CCA GAG CCA AAA TAT CAA GAT GTA CCA ACT GAG AAA AAT GAA AAA GAT
Asn Thr Pro Glu Pro Lys Tyr Gln Asp Val Pro Thr Glu Lys Asn Glu Lys Asp
```

FIG.6B

```
AAA GTT TCA TCC ATT CAA GAA CCT GCC ATG GGT TAT GGC ATG GCT TTG AGT AAA   324
Lys Val Ser Ser Ile Gln Glu Pro Ala MET Gly Tyr Gly MET Ala Leu Ser Lys

ATT AAT CTA CAC AAC CGA CAA GAC ACG CCA TTA GAT GAA AAA AAT ATC ATT ACC   378
Ile Asn Leu His Asn Arg Gln Asp Thr Pro Leu Asp Glu Lys Asn Ile Ile Thr

TTA GAC GGT AAA AAA CAA GTT GCA GAA GGT AAA TCG CCA TTT TCG               432
Leu Asp Gly Lys Lys Gln Val Ala Glu Gly Lys Lys Ser Pro Leu Pro Phe Ser

TTA GAT GTA GAA AAT AAA TTG CTT GAC AGA ATT GAT GGC TAT ATA GCA AAA GGT AAT ATG AAT GTA GCG   486
Leu Asp Val Glu Asn Lys Leu Leu Asp Arg Ile Asp Gly Tyr Ile Ala Lys MET Asn Val Ala

GAT AAA AAT GCC ATT GGT GAC AGA ATT AAG AAA GGT AAT AAA GAA ATC TCC GAT   540
Asp Lys Asn Ala Ile Gly Asp Arg Ile Lys Lys Gly Asn Lys Glu Ile Ser Asp

GAA GAA CTT GCC AAA CAA ATC AAA GAA GCT GTG CGT AAA AGC CAT GAG TTT CAG   594
Glu Glu Leu Ala Lys Gln Ile Lys Glu Ala Val Arg Lys Ser His Glu Phe Gln
```

FIG.6C

```
CAA GTA TTA TCA TCA CTG GAA AAC AAA ATT TTT CAT TCA AAT GAC GGA ACA ACC
Gln Val Leu Ser Ser Leu Glu Asn Lys Ile Phe His Ser Asn Asp Gly Thr Thr
                        621                                          648

AAA GCA ACC ACA CGA GAT TTA AAA TAT GTT GAT TAT GGT TAC TAC TTG GCG AAT
Lys Ala Thr Thr Arg Asp Leu Lys Tyr Val Asp Tyr Gly Tyr Tyr Leu Ala Asn
                        675                                          702

GAT GGC AAT TAT CTA ACC GTC AAA ACA GAC AAA CTT TGG AAT TTA GGC CCT GTG
Asp Gly Asn Tyr Leu Thr Val Lys Thr Asp Lys Leu Trp Asn Leu Gly Pro Val
                        729                                          756

GGT GGT GTG TTT TAT AAT GGC ACA ACG ACC GCC AAA GAG TTG CCC ACA CAA GAT
Gly Gly Val Phe Tyr Asn Gly Thr Thr Thr Ala Lys Glu Leu Pro Thr Gln Asp
                        783                                          810

GCG GTC AAA TAT AAA GGA CAT TGG TGG GAC TTT ATG ACC GAT GTT GCC AAC AGA AGA
Ala Val Lys Tyr Lys Gly His Trp Trp Asp Phe MET Thr Asp Val Ala Asn Arg Arg
                        837                                              864

AAC CGA TTT AGC GAA GTG AAA TCT CAA GCA GGC TGG TAT TAT GGA GCA
Asn Arg Phe Ser Glu Val Lys Asn Ser Gln Ala Gly Trp Tyr Tyr Gly Ala
                        891                                         918
```

FIG.6D

```
TCT TCA AAA GAT GAA TAC AAC CGC TTA ACT AAA GAA GAC TCT GCC CCT GAT
Ser Ser Lys Asp Glu Tyr Asn Arg Leu Thr Lys Glu Asp Ser Ala Pro Asp
                                                                    972

GGT CAT AGC GGT GAA TAT GGC AGT GAG TTT ACT GTT AAT TTT AAG GAA
Gly His Ser Gly Glu Tyr Gly Ser Glu Phe Thr Val Asn Phe Lys Glu
                                                                1026

AAA AAA TTA ACA GGT AAG CTG TTT AGT AAC CTA CAA GAC CGC CAT AAG GGC AAT
Lys Lys Leu Thr Gly Lys Leu Phe Ser Asn Leu Gln Asp Arg His Lys Gly Asn
                                                                        1080

GTT ACA AAA ACC GAA CGC TAT GAC ATC GAT GCC AAT ATC CAC GGC AAC CGC TTC
Val Thr Lys Thr Glu Arg Tyr Asp Ile Asp Ala Asn Ile His Gly Asn Arg Phe
                                                                        1134

CGT GGC AGT GCC ACC GCA AGC AAT AAA AAT GAC ACA AGC AAA CAC CCC TTT ACC
Arg Gly Ser Ala Thr Ala Ser Asn Lys Asn Asp Thr Ser Lys His Pro Phe Thr
                                                                        1188

AGT GAT GCC AAC AAT AGG CTA GAA GGT GGT TTT TAT GGG CCA AAA GGC GAG GAG
Ser Asp Ala Asn Asn Arg Leu Glu Gly Gly Phe Tyr Gly Pro Lys Gly Glu Glu
                                                                        1242
```

FIG.6E

```
CTG GCA GGT AAA TTC TTA ACC AAT GAC AAC AAA CTC TTT GGC GTC TTT GGT GCT
Leu Ala Gly Lys Phe Leu Thr Asn Asp Asn Lys Leu Phe Gly Val Phe Gly Ala
                         1269                                        1296

AAA CGA GAG AGT AAA GCT GAG GAA AAA ACC GAA GCC ATC TTA GAT GCC TAT GCA
Lys Arg Glu Ser Lys Ala Glu Glu Lys Thr Glu Ala Ile Leu Asp Ala Tyr Ala
                         1323                                        1350

CTT GGG ACA TTT AAT ACA AGT AAC GCA ACC ACA TTC ACC CCA TTT ACC GAA AAA
Leu Gly Thr Phe Asn Thr Ser Asn Ala Thr Thr Phe Thr Pro Phe Thr Glu Lys
                         1377                                        1404

CAA CTG GAT AAC TTT GGC AAT GCC AAA AAA TTG GTC TTA GGT TCT ACC GTC ATT
Gln Leu Asp Asn Phe Gly Asn Ala Lys Lys Leu Val Leu Gly Ser Thr Val Ile
                         1431                                        1458

GAT TTG GTG CCT ACT GAT GCC ACC AAA AAT GAA TTC ACC AAA GAC AAG CCA GAG
Asp Leu Val Pro Thr Asp Ala Thr Lys Asn Glu Phe Thr Lys Asp Lys Pro Glu
                         1485                                        1512

TCT GCC ACA AAC GAA GCG GGC GAG ACT TTG ATG GTG AAT GAT GAA GTT AGC GTC
Ser Ala Thr Asn Glu Ala Gly Glu Thr Leu MET Val Asn Asp Glu Val Ser Val
                         1539                                        1566
```

FIG.6F

```
                                                                1620
AAA ACC TAT GGC AAA AAC TTT GAA TAC CTA AAA TTT GGT GAG CTT AGT ATC GGT
Lys Thr Tyr Gly Lys Asn Phe Glu Tyr Leu Lys Phe Gly Glu Leu Ser Ile Gly

1674
GGT AGC CAT AGC GTC TTT TTA CAA GGC GAA CGC ACC GCT ACC ACA GGC GAG AAA
Gly Ser His Ser Val Phe Leu Gln Gly Glu Arg Thr Ala Thr Thr Gly Glu Lys

1728
GCC GTA CCA ACC ACA GGC ACA GCC AAA TAT TTG GGG AAC TGG GTA GGA TAC ATC
Ala Val Pro Thr Thr Gly Thr Ala Lys Tyr Leu Gly Asn Trp Val Gly Tyr Ile

1782
ACA GGA AAG GAC ACA GGA ACG GGC ACA GGA AAA AGC TTT ACC GAT GCC CAA GAT
Thr Gly Lys Asp Thr Gly Thr Gly Thr Gly Lys Ser Phe Thr Asp Ala Gln Asp

1836
GTT GCT GAT TTT GAC ATT GAT TTT GGA AAT AAA TCA GTC AGC GGT AAA CTT ATC
Val Ala Asp Phe Asp Ile Asp Phe Gly Asn Lys Ser Val Ser Gly Lys Leu Ile

1890
ACC AAA GGC CGC CAA GAC CCT GTA TTT AGC ATC ACA GGT CAA ATC GCA GGC AAT
Thr Lys Gly Arg Gln Asp Pro Val Phe Ser Ile Thr Gly Gln Ile Ala Gly Asn
```

FIG.6G

```
GGC TGG ACA GGC ACA GCC AGC ACC ACC AAA GCG GAC GCA GGA GGC TAC AAG ATA
Gly Trp Thr Gly Thr Ala Ser Thr Thr Lys Ala Asp Ala Gly Gly Tyr Lys Ile
                            1917                                    1944

GAT TCT AGC AGT ACA GGC AAA TCC ATC GTC ATC AAA GAT GCC AAT GTT ACA GGG
Asp Ser Ser Ser Thr Gly Lys Ser Ile Val Ile Lys Asp Ala Asn Val Thr Gly
                            1971                                    1998

GGC TTT TAT GGT CCA AAT GCA AAC GAG ATG GGC TCA TTT ACA CAC AAC GCC
Gly Phe Tyr Gly Pro Asn Ala Asn Glu MET Gly Ser Phe Thr His Asn Ala
                            2025                                    2052

GAT GAC AGC AAA GCC TCT GTG GTC TTT GGC ACA AAA AGA CAA CAA GAA GTT AAG
Asp Asp Ser Lys Ala Ser Val Val Phe Gly Thr Lys Arg Gln Gln Glu Val Lys
                            2079                                    2106
```

FIG.9A

Q8 tbpA gene sequence

```
AATTGATACAAAATGGTTTGTATTATCACTTGTATTTGTATTATAATTTTACTTATTTTT
         10                  20                  30                  40                  50                  60
ACAAACTATACACTAAAAATCAAAATTAATCACTTTGGTTGGGTGGTTTTAGCAAGCAAA
         70                  80                  90                 100                 110                 120
TGGTTATTTTGGTAAACAATTAAGTTCTTAAAAACGATACACGCTCATAAACAGATGGTT
        130                 140                 150                 160                 170                 180
TTTGGCATCTTCAATTTGATGCCTGCCTTGTGATTGGTTGGGGGTGTATTGATGTATCCA
        190                 200                 210                 220                 230                 240
                                                                MET
AGTACAAAAGCCAACAGGTGGTCATTGATG
        250                 260                 270
```

FIG.9B

```
                              ASN GLN SER LYS LYS SER LYS LYS SER LYS
                              A A T C A A T C C A A A A A A T C C A A A A A T C C A A A
                                              280                 290                 300

GLN VAL LEU LYS LEU SER ALA LEU SER LEU                 GLY LEU LEU ASN ILE THR GLN VAL ALA LEU
C A A G T A T T A A A A C T T A G T G C C T T G T C T T T G   G G T C T G C T T A A C A T C A C G C A G G T G G C A C T G
                310                 320         330                     340                 350                 360

ALA ASN THR THR ALA ASP LYS ALA GLU ALA                 THR ASP LYS THR ASN LEU VAL VAL VAL LEU
G C A A A C A C A A C G G C C G A T A A G G C G G A G G C A   A C A G A T A A G A C A A A C C T T G T T G T T G T C T T G
                370                 380         390                     400                 410                 420

ASP GLU THR VAL VAL THR ALA LYS LYS ASN                 ALA ARG LYS ALA ASN GLU VAL THR GLY LEU
G A T G A A A C T G T T G T A A C A G C G A A G A A A A A C   G C C C G T A A A G C C A A C G A A G T T A C A G G G C T T
                430                 440         450                     460                 470                 480
```

FIG.9C

```
GLY LYS VAL VAL LYS THR ALA GLU THR ILE
GGTAAGGTGGTCAAAACTGCCGAGACCATC
        490             500         510
                                        ASN LYS GLU GLN VAL LEU ASN ILE ARG ASP
                                        AATAAAGAACAAGTGCTAAACATTCGAGAC
                                           520             530             540

LEU THR ARG TYR ASP PRO GLY ILE ALA VAL
TTAACACGCTATGACCCTGGCATTGCTGTG
        550             560         570
                                        VAL GLU GLN GLY ARG GLY ALA SER SER GLY
                                        GTTGAGCAAGGTCGTGGGGCAAGCTCAGGC
                                           580             590             600

TYR SER ILE ARG GLY MET ASP LYS ASN ARG
TATTCTATTCGTGGTATGGATAAAAATCGT
        610             620         630
                                        VAL ALA VAL LEU VAL ASP GLY ILE ASN GLN
                                        GTGGCGGTATTGGTTGATGGCATCAATCAA
                                           640             650             660

ALA GLN HIS TYR ALA LEU GLN GLY PRO VAL
GCCCAGCACTATGCCCTACAAGGCCCTGTG
        670             680         690
```

FIG.9D

```
                    ALA GLY LYS ASN TYR ALA ALA GLY GLY ALA
                    GCAGGCAAAAATTATGCCGCAGGTGGGGCA
                              700       710       720

ILE ASN GLU ILE GLU TYR GLU ASN VAL ARG
ATCAACGAAATAGAATACGAAAATGTCCGC
          730       740       750
                              SER VAL GLU ILE SER LYS GLY ALA ASN SER
                              TCCGTTGAGATTAGTAAAGGTGCAAATTCA
                                        760       770       780

SER GLU TYR GLY SER GLY ALA LEU SER GLY
AGTGAATACGGCTCTGGGGCATTATCTGGC
          790       800       810
                              SER VAL ALA PHE VAL THR LYS THR ALA ASP
                              TCTGTGGCATTTGTTACCAAAACCGCCGAT
                                        820       830       840

ASP ILE ILE LYS ASP GLY LYS ASP TRP GLY
GACATCATCAAAGATGGTAAAGATTGGGGC
          850       860       870
                              VAL GLN THR LYS THR ALA TYR ALA SER LYS
                              GTGCAGACCAAAACCGCCTATGCCAGTAAA
                                        880       890       900
```

FIG.9E

```
ASN ASN ALA TRP VAL ASN SER VAL ALA ALA
AATAACGCATGGGTTAATTCTGTGGCAGCA
            910            920            930

ALA GLY LYS ALA GLY SER PHE SER GLY LEU
                    GCAGGCAAGGCAGGTTCTTTTAGCGGGTCTT
                            940            950            960

ILE ILE TYR THR ASP ARG ARG GLY GLN GLU
ATCATCTACACCGACCGCCGTGGTCAAGAA
            970            980            990

TYR LYS ALA HIS ASP ASP ALA TYR GLN GLY
                    TACAAGGCACATGATGATGCCTATCAGGGT
                            1000           1010           1020

SER GLN SER PHE ASP ARG ALA VAL ALA THR
AGCCAAAGTTTTGATAGAGCGGTGGCAACC
            1030           1040           1050

THR ASP PRO ASN ASN PRO LYS PHE LEU ILE
                    ACTGACCCAAATAACCCAAAATTTTTAATA
                            1060           1070           1080

ALA ASN GLU CYS ALA ASN GLY ASN TYR GLU
GCAAATGAATGTGCCAATGGTAATTATGAG
            1090           1100           1110
```

FIG.9F

```
                                    ALA CYS ALA ALA GLY GLY GLN THR LYS LEU
                                    GCG TGT GCT GCT GGC GGT CAA ACC AAA CTC
                                                    1120            1130            1140

GLN ALA LYS PRO THR ASN VAL ARG ASP LYS
CAA GCT AAG CCA ACC AAT GTG CGT GAT AAG
            1150            1160            1170
                                    VAL ASN VAL LYS ASP TYR THR GLY PRO ASN
                                    GTC AAT GTC AAA GAT TAT ACA GGT CCT AAC
                                                    1180            1190            1200

ARG LEU ILE PRO ASN PRO LEU THR GLN ASP
CGC CTT ATC CCA AAC CCA CTC ACC CAA GAC
            1210            1220            1230
                                    SER LYS SER LEU LEU ARG PRO GLY TYR
                                    AGC AAA TCC TTA CTG CTT CGC CCA GGT TAT
                                                    1240            1250            1260

GLN LEU ASN ASP LYS HIS TYR VAL GLY GLY
CAG CTA AAC GAT AAG CAC TAT GTC GGT GGT
            1270            1280            1290
                                    VAL TYR GLU ILE THR LYS GLN ASN TYR ALA
                                    GTG TAT GAA ATC ACC AAA CAA AAC TAC GCC
                                                    1300            1310            1320
```

FIG. 9G

```
MET GLN ASP LYS THR VAL PRO ALA TYR LEU    THR VAL HIS ASP ILE GLU LYS SER ARG LEU
ATG CAA GAT AAA ACC GTG CCT GCT TAT CTG    ACG GTT CAT GAC ATT GAA AAA TCA AGG CTC
            1330              1340                     1360              1380
                                                  1350              1370

SER ASN HIS GLY GLN ALA ASN GLY TYR TYR    GLN GLY ASN ASN LEU GLY GLU ARG ILE ARG
AGC AAC CAT GGC CAA GCC AAT GGC TAT TAT    CAA GGC AAT AAC CTT GGT GAA CGC ATT CGT
            1390              1400                     1420              1440
                                                  1410              1430

ASP ALA ILE GLY ALA ASN SER GLY TYR GLY    ILE ASN TYR ALA HIS GLY VAL PHE TYR ASP
GAT GCC ATT GGG GCA AAT TCA GGT TAT GGC    ATC AAC TAT GCT CAT GGC GTA TTT TAT GAC
            1450              1460                     1480              1500
                                                  1470              1490

GLU LYS HIS GLN LYS ASP ARG LEU GLY LEU
GAA AAA CAC CAA AAA GAC CGC CTA GGG CTT
            1510              1520
                         1530
```

FIG.9H

```
GLU TYR VAL TYR ASP SER LYS GLY GLU ASN
GAA TAT GTT TAT GAC AGC AAA GGT GAA AAT
            1540            1550            1560

LYS TRP PHE ASP ASP VAL ARG VAL SER TYR
AAA TGG TTT GAT GAT GTG CGT GTG TCT TAT
            1570            1580            1590

ASP LYS GLN ASP ILE THR LEU ARG SER GLN
GAC AAG CAA GAC ATT ACG CTA CGT AGC CAG
            1600            1610            1620

LEU THR ASN THR HIS CYS SER THR TYR PRO
CTG ACC AAC ACG CAC TGT TCA ACC TAT CCG
            1630            1640            1650

HIS ILE ASP LYS ASN CYS THR PRO ASP VAL
CAC ATT GAC AAA AAT TGT ACG CCT GAT GTC
            1660            1670            1680

ASN LYS PRO PHE SER VAL LYS GLU VAL ASP
AAT AAA CCT TTT TCG GTA AAA GAG GTG GAT
            1690            1700            1710

ASN ASN ALA TYR LYS GLU GLN HIS ASN LEU
AAC AAT GCC TAC AAA GAA CAG CAC AAT TTA
            1720            1730            1740
```

FIG. 9I

```
ILE LYS ALA VAL PHE ASN LYS MET ALA                    LEU GLY ASN THR HIS HIS ILE ASN LEU
ATCAAAGCCGTCTTTAACAAAAATGGCA                           TTGGGCAATACGCATCATCACATCAATCTG
            1750              1760           1770              1780           1790           1800

GLN VAL GLY TYR ASP LYS PHE ASN SER SER                LEU SER ARG GLU ASP TYR ARG LEU ALA THR
CAAGTTGGCTATGATAAATTCAATTCAAGC                         CTTAGCCGTGAAGATTATCGTTTGGCAACC
            1810              1820           1830              1840           1850           1860

HIS GLN SER TYR GLN LYS LEU ASP TYR THR                PRO PRO SER ASN PRO LEU PRO ASP LYS PHE
CATCAATCTTATCAAAAACTTGATTACACC                         CCACCAAGTAACCCTTTGCCAGATAAGTTT
            1870              1880           1890              1900           1910           1920

LYS PRO ILE LEU GLY SER ASN ASN ARG PRO
AAGCCCATTTTAGGTTCAAACAACAGACCC
            1930              1940           1950
```

FIG. 9J

```
                              ILE CYS LEU ASP ALA TYR GLY TYR GLY HIS
                              A T T T G C C T T G A T G C T T A T G G T T A T G G T C A T
                                                  1960          1970          1980

ASP HIS PRO GLN ALA CYS ASN ALA LYS ASN
G A C C A T C C A C A G G C T T G T A A C G C C A A A A A C
              1990          2000          2010

SER THR TYR GLN ASN PHE ALA ILE LYS LYS
                              A G C A C T T A T C A A A A C T T T G C C A T C A A A A A A
                                                  2020          2030          2040

GLY ILE GLU GLN TYR ASN GLN THR ASN THR
G G C A T A G A G C A A T A C A A C C A A T A C C
              2050          2060          2070

ASP LYS ILE ASP TYR GLN ALA VAL ILE ASP
                              G A T A A G A T T G A T T A T C A A G C C G T C A T T G A C
                                                  2080          2090          2100

GLN TYR ASP LYS GLN ASN PRO ASN SER THR
C A A T A T G A T A A A C A A A A C C C C A A C A G C A C C
              2110          2120          2130

LEU LYS PRO PHE GLU LYS ILE LYS GLN SER
                              C T A A A C C C T T T G A G A A A A T C A A A C A A A G T
                                                  2140          2150          2160
```

FIG.9K

```
LEU GLY GLN GLU LYS TYR ASP GLU ILE ASP
TTGGGGCAAGAAAAATACGACGAGATAGAC
         2170              2180              2190

ARG LEU GLY PHE ASN ALA TYR LYS ASP LEU
              AGACTGGGCTTTAATGCTTATAAAGATTTA
                   2200              2210              2220

ARG ASN GLU TRP ALA GLY TRP THR ASN ASP
CGCAACGAATGGGCGGGGTTGGACTAATGAC
         2230              2240              2250

ASN SER GLN GLN ASN ALA ASN LYS GLY THR
              AACAGCCAACAAAACGCCAATAAAGGCACG
                   2260              2270              2280

ASP ASN ILE TYR GLN PRO ASN GLN ALA THR
GATAATATCTATCAGCCAAATCAAGCAACT
         2290              2300              2310

VAL VAL LYS ASP ASP LYS CYS LYS TYR SER
              GTGGTCAAAGATGACAAATGTAAATATAGC
                   2320              2330              2340

GLU THR ASN SER TYR ALA ASP CYS SER THR
GAGACCAACAGCTATGCTGATTGCTCAACC
         2350              2360              2370
```

FIG.9L

```
             THR ARG HIS ILE SER GLY ASP ASN TYR PHE
             ACTCGCCACATCAGCGGGTGATAATTATTTC
                      2380         2390          2400

ILE ALA LEU LYS ASP ASN MET THR ILE ASN
ATCGCTTTAAAAGACAACATGACCATCAAT
         2410         2420         2430
             LYS TYR VAL ASP LEU GLY LEU GLY ALA ARG
             AAATATGTTGATTTGGGGCTGGGTGCTCGC
                      2440         2450          2460

TYR ASP ARG ILE LYS HIS LYS SER ASP VAL
TATGACAGAATCAAACACAAATCTGATGTG
         2470         2480         2490
             PRO LEU VAL ASP ASN SER ALA SER ASN GLN
             CCTTTGGTAGACAACAGTGCCAGCAACCAG
                      2500         2510          2520

LEU SER TRP ASN PHE GLY VAL VAL LYS
CTGTCTTTGGAATTTGGCGTGGTCGTCAAG
         2530         2540         2550
             PRO THR ASN TRP LEU ASP ILE ALA TYR ARG
             CCCACCAATTGGCTGGACATCGCTTATAGA
                      2560         2570          2580
```

FIG.9M

```
SER SER GLN GLY PHE ARG MET PRO SER PHE
AGCTCGCAAGGCTTTCGCATGCCAAGTTTT
    2590            2600            2610
                                            SER GLU MET TYR GLY GLU ARG PHE GLY VAL
                                            TCTGAAATGTATGGCGAACGCTTTGGCGTA
                                                2620            2630            2640

THR ILE GLY LYS GLY THR GLN HIS GLY CYS
ACCATCGGTAAAGGCACGCAACATGGCTGT
    2650            2660            2670
                                            LYS GLY TYR LEU TYR TYR ILE CYS GLN GLN THR
                                            AAGGGTCTTTATTACATTTGTCAGCAGACT
                                                2680            2690            2700

VAL HIS GLN THR LYS LEU LYS PRO GLU LYS
GTCCATCAAACCAAGCTAAAACCTGAAAAA
    2710            2720            2730
                                            SER PHE ASN GLN GLU ILE GLY ALA THR LEU
                                            TCCTTTAACCAAGAAATCGGAGCCGACTTTA
                                                2740            2750            2760

HIS ASN HIS LEU GLY SER LEU GLU VAL SER
CATAACCACTTAGGCAGTCTTGAGGTTAGT
    2770            2780            2790
```

FIG.9N

```
                                       TYR PHE LYS ASN ARG TYR THR ASP LEU ILE
                                       TAT TTT AAA AAT CGC TAT ACC GAT TTG ATT
                                                       2800              2810              2820

VAL GLY LYS SER GLU GLU ILE ARG THR LEU   THR GLN GLY ASP ASN ALA GLY LYS GLN ARG
GTT GGT AAA AGT GAA GAG ATT AGA ACC CTA   ACC CAA GGT GAT AAT GCA GGC AAA CAG CGT
         2830              2840                     2850              2860              2870              2880

GLY LYS GLY ASP LEU GLY PHE HIS ASN GLY   GLN ASP ALA ASP LEU THR GLY ILE ASN ILE
GGT AAA GGT GAT TTG GGC TTT CAT AAT GGG   CAA GAT GCT GAT TTG ACA GGC ATT AAC ATT
         2890              2900                     2910              2920              2930              2940

LEU GLY ARG LEU ASP LEU ASN ALA VAL ASN   SER ARG LEU PRO TYR GLY LEU TYR SER THR
CTT GGC AGA CTT GAC CTA AAC GCT GTC AAT   AGT CGC CCT TCC CTA TGG ATT ATA CTC AAC A
         2950              2960                     2970              2980              2990              3000
```

FIG. 90

```
LEU ALA TYR ASN LYS VAL ASP VAL LYS GLY
CTGGCTTATAACAAAGTTGATGTTAAAGGA
         3010              3020         3030
                                              LYS THR LEU ASN PRO THR LEU ALA GLY THR
                                              AAAACCTTAAACCCAACTTTGGCAGGAACA
                                                    3040         3050         3060

ASN ILE LEU PHE ASP ALA ILE GLN PRO SER
AACATACTGTTTGATGCCATTCAGCCATCT
         3070              3080         3090
                                              ARG TYR VAL VAL GLY LEU GLY TYR ASP ALA
                                              CGTTATGTGGTGGGGCTTGGCTATGATGCC
                                                    3100         3110         3120

PRO SER GLN LYS TRP GLY ALA ASN ALA ILE
CCAAGCCAAAAATGGGGAGCAAACGCCATA
         3130              3140         3150
                                              PHE THR HIS SER ASP ALA LYS ASN PRO SER
                                              TTTACCCATTCTGATGCCAAAAATCCAAGC
                                                    3160         3170         3180

GLU LEU LEU ALA ASP LYS ASN LEU GLY ASN
GAGCTTTTGGCAGATAAGAACTTAGGTAAT
         3190              3200         3210
```

FIG.9P

```
              GLY ASN ILE GLN THR LYS GLN ALA THR LYS
              GGCAACATTCAAACAAAACAAGCCACCAAA
                      3220        3230        3240

ALA LYS SER THR PRO TRP GLN THR LEU ASP
GCAAAATCCACGCCCGTGGCAAACACTTGAT
        3250        3260        3270

LEU SER GLY TYR VAL ASN ILE LYS ASP ASN
              TTGTCAGGTTATGTAAACATAAAAGATAAT
                      3280        3290        3300

PHE THR LEU ARG ALA GLY VAL TYR ASN VAL
TTTACCCTTGCGTGGCGTGTACAATGTA
        3310        3320        3330

PHE ASN THR TYR TYR THR TRP GLU ALA
              TTTAATACCTATTACACCACTTGGGAGGCT
                      3340        3350        3360

LEU ARG GLN THR ALA GLU GLY ALA VAL ASN
TTACGCCAAACAGCAGAAGGGGCGGTCAAT
        3370        3380        3390

GLN HIS THR GLY LEU SER GLN ASP LYS HIS
              CAGCATACAGGACTGAGCCAAGATAAGCAT
                      3400        3410        3420
```

FIG. 9Q

```
TYR GLY ARG TYR ALA ALA PRO GLY ARG ASN
TATGGTCGCTATGCCGCTCCTGGACGCAAT
          3430                    3440                    3450
                                              TYR GLN LEU ALA LEU GLU MET LYS PHE ***
                                              TACCAATTGGCACTTGAAATGAAGTTTTAA
                                                  S
                                                          3460                    3470
3480

CCAGTGGCTTTGATGTGATCATGCCAAATC             CCAATCAACCAATGAATAAAGCCCCCATCT
          3490                    3500                    3510                    3520                    3530                    3540

ACCATGAGGGCTTTATTTTATCATCGCTGA             GTATGCTCTCTTAGCGGTCATCACTCAGATTA
          3550                    3560                    3570                    3580                    3590                    3600

GTCATTAATTTATTAGCGGATTAATTTATTA            GTAATCACGCTGCTCTTTGATGATTTTAAG
          3610                    3620                    3630                    3640                    3650                    3660
```

FIG.10A

Tbp1 alignment

```
                                                                         4223
                                                                         Q8
                                                                         B16B6
                                                                         M982
                                                                         FA19
                                                                         Eagan 10        20        30        40        50        60
MNQSKQNNKSKKKSKQVLKLSALSLGLLNI--TQVALANTTADKAEFA-TDKINLVVLDETVVT
..Q.QHLFR----------.NILC....--------.MT.PVY-----..NVQAEQAQEKQ..TIQ.K
..Q.QHLFR----------.NILC....--------.MT.PAY-----..NVQAGQAQEKQ..TIQ.K
..Q.QHLFR----------.NILC....--------.MT.PAY-----..NVQAGQAQEKQ..TIQ.K
..Q.QHLFR----------.NILC....--------.MT.PAY-----..NVQAGQAQEKQ..TIQ.K
..TKKPYFR----------LSIISC.LI.CYVKAE..SIKDIKE.ISS.VD.QS.E-DSE.ETIS..

70        80        90        100
AKKNA-RKANEVTGLGKVVKTAETINKEQVLNIRDLTRYDP
...QKT.RD..........L..SSD.LS............
...QKT.RD..........L....D.LS....D.......
...QKT.RD..........L....D.LS....D.......
...QKT.RD..........L....D.LS............
...E.IRD..D........II...S.S.SR..........

110       120       130       140       150       160
GIAVVEQGRGASSGYSIRGMDKNRVAVLVDGINQAQHYALQGPVAGKNYA-AGGAINEIEYEN
..........................SLT...VS.I.S.TA.AALG.TRT.GSS.........
..........................SLT...LA.I.S.TA.AALG.TRT.GSS.........
..........................SLT...LA.I.S.TA.AALG.TRT.GSS.........
..........................SLT...LA.I.S.TA.AALG.TRT.GSS.........
.S................R.....L....LP.T.S.VV.S.LVATSGYSGT.............
```

FIG.10B

```
                    170       180       190       200
          VRSVEISKGANSSEYGSGALSGSVAFVIKTADDIIKDG            4223
          .KA......S.....N..A....Q....A...GE.              Q8
          .KA......S.V.Q...A....Q....A...V.GE.             B16B6
          .KA......S.V.Q...A....Q....A...V.GE.             M982
          .KA.........N..A....T.QS.S.A..LEGD               FA19
          .KA........GS...N..A....T.QS.S.A..LEGD           Eagan 210       220       230       240       250       260
KDMGVQTKTAYASKNNAWNSVAAAGKAGSFSGLIIYTDRRGQEYKAHDDAYQGSQSFDRAVA
..Q..I.S....SG..DH.LTQ.L.L..RS.GAEA.L...K..R.IH..K..GK.V...N.L.L
RQ..I.S....SG..RGLTQ.I.L..RI.GAEA.L.H.G..AG.IR..E..GR.V...N.L.P
RQ..I.S....SG..RGLTQ.I.L..RI.GAEA.L.H.G..HAG.IR..EA.GR.V...N.LAP
.S..I....N..S....KGFTH.L.V...Q.G.E..A....Q.NSI.TQV.K..LK.V..Y.LI.

270       280       290       300
          TTD------PNNRIFLIANECANENYEACAAGGQIKLQAKPTN         4223
          .........PK..                                       Q8
          DE..KKEGGSQY.Y.IVEE..H..-.A..KNKL---.ED.SVKD        B16B6
          VE.-----SSEYAY.IVED..EGK....T.KSKP---.KDVGKD        M982
          VE.-----GSKYAY.IVEE..K..GH.K.K.NP---.KDVVGED        FA19
          .-------KSSGY.V..QG..P..DDK-.....-----PP..TLST      Eagan
```

FIG. 10C

```
     310        320        330        340        350        360
VRDKVNVKDYTGPNRLIPNPLTQDSKSLLLRPGYQLNDK-HYVGGVYEITKQNYAMQDKTVPA
.....E.KT.STQ....S...LA...EYG.Q.W.F...WH.DNR-.......A.L.R.Q.TFDIR.M....
.....E.QT.STR.......FLAD..SYE.R.W.F...FRFENKR..I...IL.H.Q.TFDIR.M....
.....K.QT.STR.......FLAD..SYE.R.W.F...FRFENKR..I...IL.R.Q.TFDIR.M....
QSET.S.S......A..IK...MKYE.Q.WF..G..HFSEQ-...I..IF.F.Q.KFDIR.M.F..
                   370        380        390        400
             YLTVHDIEKSRLSNHAQA--NGYYQGNNLGERIRDTIGPD    4223
             ..............G..-------...............A..AN  Q8
             .F.SE.YVPGS.KGL------.K.S.D.KA..LFVQGEGS      B16B6
             F..KAVFDANSKQAGSLPG-.K.A..HKYGGLFTNGENG       M982
             F..KAVFDANQKQAGSLPG-.K.A..HKYGGLFTSGENN       FA19
             ..SPTERRDDSSRSFYPMQDH.A..HIE------            Eagan 410        420        430        440        450        460
----SGYGINYAHGVFYDEKHQKDELGLEYVYDSKGENKWFDDVRSYDKQDITLRSQLTNTHC
---TLQGI.----T.......R.T.N.Y.V....HNADKDT.A.YA.L....R.G.D.DNR.QQ...
---ALV.AE.GT.......T.T.S.Y......TNADKDT.A.YA.L....R.G.G.DNHFQQ....
---APV.AE.GT.......T.T.S.Y......TNADKDT.A.YA.L....R.G.G.DNHFQQ....
...D.R.VK...S.LYF..H.R.Q.V.I...I.EN.NKAGII.KAVL.ANQ.N.I.D.YMRH...
```

FIG.10D

```
              470       480       490       500
     STYPHIDKNCTPDVNKPFSVKEVDNAYKEQHNLIKAVFN     4223
     .........................................  Q8
     .HDGS-....R..G...Y.FYKS.RMI.E.SR..FQ...K    B16B6
     .ADGS-....Y.R.SAD...YYKS.RVI.G.S.R.LQ.A.K   M982
     .ADGS-....Y.R.SAD...YYKS.RVI.G.S.K.LQ.A.K   FA19
     .L..NPS...R.TLD..Y.YYRS.R.V...K..MLQLNLE    Eagan 510       520       530       540       550       560
KKMALGSTHHHIDNLQVGYDKFNSSLSREDYRLATHQSYQKLDYTPPSNPLPDKF-KPILGSNN
.........N.....................................................-
..AFDTAKIR.NLSINL..R.K.Q..HS...Y.QNAVQAYD.I-...KP.F.NGS-------D
.SFDTAJUR.NKSVNK.F.R.S.B.RHQ..YYQHANRAYSSK-...KTAN.NGD--------S
.SFDTAKIR.NLSVNL...T.G.N.RHQ..YYQSANRAYS.K-...Q.NGKKTS---PN.REK
..IQQMLT.Q.VFNL.F.D.T.A.QHK...-TRRVIATA-.SI.RK----.GETG..RN.LQS
              570       580       590       600
     KPICLDAYGYGHDHPQACVAKNSTYQNFAIKKGIEQYN          4223
     R............................................  Q8
     N.YRVSIGK------------------------------------   B16B6
     ..YWSIG.-------------------------------------   M982
     N.YWSIGR-------------------------------------   FA19
     Q.YLYPKPEP-----------------------------------   Eagan
```

FIG.10E

```
       610       620       630       640       650       660
QKINIDKIDYQAIIDQYDKQNPNSTLKPFEKIKQSLGQEKYNKIDELGFKAYKDLRNEWAGWT      4223
-..V................................................               Q8
----------------------------------------------------------          B16B6
----------------------------------------------------------          M982
----------------------------------------------------------          FA19
................................DE.R..N.....                       Eagan 670       680       690       700
NDNSQQNANKGRDNIYQPNQA-TVVKDDKCKYSETNS-Y                             4223
..............-...............:..-.                                Q8
----------T..NTSPI.RFGN-.T-.                                        B16B6
----------GN..TGQI.LFGN-.T-.                                        M982
----------GN..TRQI.LFGN-.T-.                                        FA19
----------YFAGQDH-.N.QGSS.N.                                        Eagan 710       720       730       740       750       760
ADCSTTRHISGDNYFIALKDNMTINKYVDLGLGARYDRIKHKSDVPLVDNSASNQLSMNFGVV     4223
...................................................              Q8
T..-.P.N.G.NG..YA.VQ..VRLGRWA.V.A.I...YRSTH.EDKS.SIGTHRN....A...    B16B6
T..-.P.S.N.KS.YA.VR..VRLGRWA.V.A.L...YRSTH..DGS.SIGTHRT...A.I.      M982
T..-.P.S.N.KS.YA.VR..VRLGRWA.V.A.L...YRSTH..DGS.SIGTHRT...A.I.      FA19
R.-KV.L.K.K..YF.ARN..ALG........I...VSRT.ANESTISVGKFKNF..T.I.       Eagan
```

FIG.10F

```
                                            770       780       790       800
                                   VKPTMLDIAYRSSQGFRMPSFSEMYGERFGVTIGKG    4223
                                   ................................... Q8
                                   L..FT.M.LT..A.T...L...A....W.A.ESLKTL B16B6
                                   L..AD...LT..T.T...L...A....W.S..OSKAV M982
                                   L..AD...LT..T.T...L...A....W.S.DK.KAV FA19
                                   I...E...LS..L.T...N.........W.Y.GKNDEV Eagan 810       820       830       840       850       860
TQHGCKGLYYICQQTVHQTKLKPEKSFNQEIGATLHNHLGSLEVSYFKNRYTDLIVGKSEEIR
..............................................................
-----------D..........R.A..IVFKGDF.N...A...N.A.R....AFGY-.T.
-----------ID..........K.A..IVFKGDF.N..A.W.N.A.R.....RGY.AQI
-----------ID..........K.A..IVFKGDF.N..A.W.N.A.R.....RGY.AQI
---------YVG.F...T.R...F.LA.KGDF.NI.I.H.S.A.RN..AFA-..LS 870       880       890       900
                                   TLTQGDVAGKQRGKGDLGFHNGQDADLTGINILGRLD   4223
                                   ....................................N............K..  Q8
                                   .------QN.QTSAS..P.YR.A.N.RIA......KI.. B16B6
                                   K------N..EEA...PAYL.A.S.RI........KI.. M982
                                   K------D..EQV..NPAYL.A.S.RI........KI.. FA19
                                   K------NGT..NY.Y..A.N.K.V.V..TAQ..    Eagan
```

FIG. 10G

```
           910       920       930       940       950       960
           ....|....|....|....|....|....|....|....|....|....|....|....|
           LNAVNSRLPYGLYSTLAYNKVDVKGKTLNPTLAG-TNILFDAIQPSRYVVGLGYDAPSQKMGA
           ..WHG..WGG..D......RIK..DADIRADRTFV.SY.....V......L......H.DGI..I        4223
           ..WNG..WDK..E.W..F...R.H.RDIKKRADRTDIQSH..................Q.EG..V        Q8
           ..WNG..WDK..E.W..F...R.H.RDIKKRADRTDIQSH................S..Q.EG..V      B16B6
           ..WNG..WDK..E.W..F...R.H.RDIKKRADRTDIQSH..................Q.EG..V        M982
           ..F.GLMK.I...W.A.F...Q.K..DQKI.AG..SVSSY............II......H..NT..I    FA19
                                                                                    Eagan 970       980       990      1000
           ....|....|....|....|....|....|....|....|
           NAIFTHSDAKNPSELLADKNLGNGNIQ-TKQATKAKSTP
           ......................................        4223
           .TM.Y.K..SVD...GSQA.L...ANAK.A-ASRRTR.          Q8
           .GML.Y.K..EIT...GSRA.L...SRN.A-.ARRTR.         B16B6
           .GML.Y.K..EIT...GSRA.L...SRN.A-.ARRTR.         M982
           .TM..Q.K..SQN...GKRA...-..SRDV.S-.RKLTRA       FA19
                                                          Eagan 1010      1020      1030      1040      1050      1060      1070
           ....|....|....|....|....|....|....|....|....|....|....|....|....|....|
           WQTLDLSGYVNIKDNFTLRAGVYNVFNTYTIWEALRQTAEGAVNQHIGLSQDKHYGRYAAPGRNYQLALEMKF*
           .YVT.V.....Y...KHL..........LL.YR.V....NV.....G........---KNVGV.N........TFS......*    4223
           .YIV.V.....YT..KH...........LL.YR.V....NV.....G........---KNVGV.N........TFS......*    Q8
           .YIV.V.....YTV.KH...........LL.YR.V....NV.....A........---KNVGV.N........TFS......*    B16B6
           .YIV.V.....YTV.KH...........LL.HR.V....NV.....A........---KNVGV.N........TFS......*    M982
           .HI..V.....YMANK.IM.L.I..L..YR.V.......V......Q........---QNVGS.T......S....T.T...*    FA19
                                                                                                  Eagan
```

FIG.11A

Tbp 2 alignment

```
              10         20         30         40         50         60         70         80         90        100
4223    MKHIPLTTLCVAISAVLLTAC-GGSGGSNPPAPTPIPNASGSGNTGNTGNAGGTNTANAGNTGGTNSGTGSANTPEPKYQDVPTEKNEKDK-VSSIQEP
B16B6   .NNPLVNQAAMLPVF..S..L..G.SFDLDSVETVQDMH-----------------------------------SK...E.EKSQ-P.SQQD..ENSGA
M918    .NNPLVNQAAMLPVF..S..L..G.SFDLDSVDT-EAPR-----------------------------------.A.......SS..PQAQ.D-----QG
FA19    .NNPLVNQAAMLPVF..S..L..G.SFDLDSVDT-EAPR-----------------------------------.A.........SK.P.AR.D-----QG
EAGAN   ..SV..ISGGLSF----..S..-S.G.SFDVDNVSNTPSSK---------------------------------------R...DTSNORK.SN-LKKLFI.

110        120        130        140        150        160        170        180        190        200
4223    AMGYGWALSKINLHNRQDTP-LDEKNIITTLDGKKQVAEGKKSPLPFSLDVENKLLDGYIAKMNVADKNAIGDRIKKGNKEI-SDEELAKQIKEAVRKSHE
B16B6   .Y.FAVK.PRR.A.FNPKY-----KEKHKP.GSMDW-------------------------.LQRGEP.SFSE.DELEK.R--GSS..IESKW.DG----
M918    GY.FAMR.KRR.WYPGAE------ESEVK.NESDWEAT.---------.PTKP.--------ELPKRQ.SV.EKVETD.DSDIY.SPY.TPSNHQNGSAGNG
FA19    GY.FAMRFKRR.W.PSANP-----KEDEVK.KNDDWEAT.---------.PT.P.--------.LPLKQQSV.SEVETN..SKMYTSPY.---SQDADSSHANG
EAGAN   SL.G..K.VAQ..RGNKEPSF.N.DDY.S-----------------------.FSSLSTIEKD-----V.DN..NG-AD------

210        220        230        240        250        260        270        280        290        300
4223    FQQVLSSLENKIFHSNDGTTKATTRDLKYVDGYYLANDGNYLTVKTDKLW-NLGPVGGVFYNGTTTAKELPTQDAVKYKGHMDFMTDVANRRNRFSEVK
B16B6   ---Q.RVVG---------YTNFT..RS..VYL..K.NIDI.NNIVL--F..D.YLY.K.KEPSKE..-SEKIT...T..YV..AMEKQRFEGL--
M918    VN.PKNQATG--------HENFQ..YSGWFYKHAASEKDFSNKKI--KS.DD.YI..H.EKPSRQ..ASKG.I...V.HFV..TKKGQDFREIIQ
FA19    AN.PKNEVTD--------YKKF...YSGWFYKHAKSEVKNENGLVSAKR.DD.YI..H.DKPSRQ..ASE.T...V.HFV..TKQGQKFNDTLE
EAGAN   --------IGSIDEPSTTNPPEKHHGQ...YSGL.YTP-SWS.NDSKN.FY--..YY.YA..Y.NK..TN..VNGV....T...I.ATK.GK-.YPLLS
```

FIG.11B

```
              310        320        330        340        350        360        370        380        390        400
4223    ENSQAGWYGASSKDEYNRLLTKEDSAPDGHSGEYGHSSEFTVNFKEKKLTGKLFSNLQDRHKGNVT---KTERYDIDANIHGNRFRGSATASNKNDTSK
B1686   GSAAG.DKS..L.AL.EGV.RNQAEAS--SGHTDF.MT...E.D.SD.TIK.T.YR.NRITQNNSENKQI..T..TIQATL....K.K.L.AD.GA.NG
M918    PSKKQ.DR.SFG.G.GSEEYSN.NE.TLKDDHEG..FT.NLE.D.GN.......IR.NASLNNTNNDKHTTQY.SLDAQ.T..P.N.T...TD.-KENE
FA19    TSKGQ.KD.SDF.G..GETTSNRTD.NLNDKHEG..FT.N.K.D.NN.......IR.NKVINTAASDG-YTT.Y.SLDATLR....S.K.I.TD.PN.GG
EAGAN   NGSHA--.RRSAIPE------DIDLENDSKN.DI.LI...SAD.GT.....Q.SYTKRKTNNQPYE---.KKL.....D.YS.....TVKPTE.-.SEE 410        420        430        440        450        460        470        480        490        500
4223    ---HPFTSDANNRLEGGFYGPKGEELAGKFLTNDNKLFGVFGAKR--ESKAEEKTEAILDAYALGTFNT-----SNATTFTP----------------
B1686   S--..I..SDS-..........S.....VAA....QKDKKDG.NAAGP-----------.A.E-----------TVIDAYRITGEE
M918    TKL...V..SSS-.....F..Q....D.Q.VAV.GS..TKDKLENGAAASG---------S.GAAASGGA.G.SSENDKLTTVLDAVELTLND
FA19    TKL...VF.SSS-.S..F..Q....GFR..SD.G.VAV.GS..TKD---------STANG----.APAASSGPG.A.MPSETRLTTVLDAVELTPDG
EAGAN   -......EGT---.......NA....AT..RV...FS..ETE.T.K.ALSKET.IDGK.I..S.KKTDAKTN...S.AANTTDTTANTITDEKN 510        520        530        540        550        560        570        580        590        600
4223    FTEKQLDNFGNAKKLVLGSTVIDLVPTDATKNEFTKDKPES---------------------ATNEAGETLMNDEVSV
B1686   .KKE.I.S..DV....LVDGVELS.L.SEGN.AA.QHEIEQNGV-------------------------KATVCCSNLDY
M918    KKI.N....S..AQ..VDGIM.P.L.K.SESGNTQA..GKNGGTEFTRKFEHTPESDKKDAQAGTQTNGAQTASNTAGDTNGK--TKTY.VEVCCSNLNY
FA19    KEI.N....S..TR..VDGIM.P.L.--TESGNGQA..GKNGGTDFTYETTYPESDKKDTKAQTGAGGMQTASGTAGVNGGQVGTKTYKVQVCCSNLNY
EAGAN   .KTEDISS..E.DY.LIDKYP.P.L-.KNTND.ISS.HHT-------------------------------VGNKRYKVEACCSNL.Y
```

FIG.11C

```
          610        620        630        640        650        660        670        680        690        700
4223   KTYGKNFEY-LKFGELSIGGSHSV------------------------------------FLQGERTATTGEKAVPTTGTAKYLGMWGYIT-GKDTGTGTGKSFTDAQDV
B16B6  MSF.....SKENK-----------------DDM-------------------------------V..P-VSDV.AR.EAN...R.T.Y...AN.TSWSGEASNQ-EGGNR
M918   LK..M------.TRKNSKSAMQAGGNSSQADAKTEQVEQSM---------------------D-EKEIPT--DQNVV.R.S.Y.H.AN.TSWSGNASDK--EGGNR
FA19   LK..L------.TRENNNSVMQAVKNSSQADAKTKQIEQSM---------------------D-ENKIPQ--EQGIV...F.Y.R.AN.TSWSGKASNA--TDGNR
EAGAN  VKF.MYY.DP..EK.TETETETEKDKEKEKDKDKEKQTAATTNTYYQ..L.H..PKDD---I.K..S....H.S.F....D..TSYSPS..DKKR..KNAV 710        720        730        740        750        760        770        780        790        800
4223   ADFDIDFGNKSVSGKLITKGRQDPVFSITGQI--AGNGWTGTASTTKADAGGYKIDSSSTGKS--IAIKDANVTGGFYGPNANEMGGSFTHNAD---------------
B16B6  .E..V..ST.KI..TLTA.D.TS.A.T..AM.K-D..FS.V.K.GE---N.FAL.PQN..N.HYTH.-E.T.S.....K..I.......SFPGNAP---
M918   ...T.N.AD.KIT....TAEN..AQT.T.E.M.Q---..FE....K.AE---S.FDL.QKN.TRTPKAY.T..K.K......KAE.L...W.AYPG..KQ----
FA19   .K.TVN.DR.ETT.T.TAEN.SEAT.T.DAM.E----.FK....K.GN---D.FAP.QNNSTVTHKVH.AN.E.Q........E.L...W.AYPGNEQ-----
EAGAN  .E.NV..AE.KLT.E.KRHDTGN.....EANFNNSS.AF....TA.NFVID.KNSQNKN.PIN---TTK---N.A....KAS.L..Y..YNGNSTATNS 810        820        830
4223   ---------DSKASVVFGTKRQQEV--K*
B16B6  EGKQE-------K......A.....L.--Q*
M918   TEKATATSSDGNSA.S.T....A....P.--Q*
FA19   TKNATVESGNGNSA.S.T....A...KL.--*
EAGAN  ESSSTVSSSSNSKNAR.A....ARQ.V.TT-.*
```

Expression of rTbp1 in *E. coli*

1. Prestained molecular weight markers 2. pLEM29B-1 lysate, non-induced 3. pLEM29B-1 lysate, 1 hr post-induction 4. pLEM29B-1 lysate, 3 hr post-induction

Purification of rTbp1 from *E. coli*

1. *E. coli* Whole cells

2. Soluble proteins after 50 mM Tris/ NaCl extraction

3. Soluble proteins after Tris/ Triton X-100/ EDTA extraction

4. Soluble proteins after Tris/ urea/ DTT extraction

5. Left-over pellet (rTbp1 inclusion bodies)

6.7. Purified rTbp1

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
        (A) LENGTH: 3438 base pairs
        (B) TYPE: nucleic acid
        (C) STRANDEDNESS: single
        (D) TOPOLOGY: linear (xi) SEQUENCE DESCRIPTION: SEQ ID NO:1:

```
TATTTTGACA AGCTATACAC TAAAATCAAA AATTAATCAC TTTGGTTGGG TGGTTTTAGC      60

AAGCAAATGG TTATTTTGGT AAACAATTAA GTTCTTAAAA ACGATACACG CTCATAAACA     120

GATGGTTTTT GGCATCTGCA ATTTGATGCC TGCCTTGTGA TTGGTTGGGG TGTATCGGTG     180

TATCAAAGTG CAAAAGCCAA CAGGTGGTCA TTGATGAATC AATCAAAACA AAACAACAAA     240

TCCAAAAAAT CCAAACAAGT ATTAAAACTT AGTGCCTTGT CTTTGGGTCT GCTTAACATC     300

ACGCAGGTGG CACTGGCAAA CACAACGGCC GATAAGGCGG AGGCAACAGA TAAGACAAAC     360

CTTGTTGTTG TCTTGGATGA AACTGTTGTA ACAGCGAAGA AAAACGCCCG TAAAGCCAAC     420

GAAGTTACAG GGCTTGGTAA GGTGGTCAAA ACTGCCGAGA CCATCAATAA AGAACAAGTG     480

CTAAACATTC GAGACTTAAC ACGCTATGAC CCTGGCATTG CTGTGGTTGA GCAAGGTCGT     540

GGGGCAAGCT CAGGCTATTC TATTCGTGGT ATGGATAAAA ATCGTGTGGC GGTATTGGTT     600

GATGGCATCA ATCAAGCCCA GCACTATGCC CTACAAGGCC CTGTGGCAGG CAAAAATTAT     660

GCCGCAGGTG GGGCAATCAA CGAAATAGAA TACGAAAATG TCCGCTCCGT TGAGATTAGT     720

AAAGGTGCAA ATTCAAGTGA ATACGGCTCT GGGGCATTAT CTGGCTCTGT GGCATTTGTT     780

ACCAAAACCG CCGATGACAT CATCAAAGAT GGTAAAGATT GGGGCGTGCA GACCAAAACC     840

GCCTATGCCA GTAAAAATAA CGCATGGGTT AATTCTGTGG CAGCAGCAGG CAAGGCAGGT     900

TCTTTTAGCG GTCTTATCAT CTACACCGAC CGCCGTGGTC AAGAATACAA GGCACATGAT     960

GATGCCTATC AGGGTAGCCA AAGTTTTGAT AGAGCGGTGG CAACCACTGA CCCAAATAAC    1020
```

-continued

```
CGAACATTTT TAATAGCAAA TGAATGTGCC AATGGTAATT ATGAGGCGTG TGCTGCTGGC    1080

GGTCAAACCA AACTTCAAGC CAAGCCAACC AATGTGCGTG ATAAGGTCAA TGTCAAAGAT    1140

TATACAGGTC CTAACCGCCT TATCCCAAAC CCACTCACCC AAGACAGCAA ATCCTTACTG    1200

CTTCGCCCAG GTTATCAGCT AAACGATAAG CACTATGTCG GTGGTGTGTA TGAAATCACC    1260

AAACAAAACT ACGCCATGCA AGATAAAACC GTGCCTGCTT ATCTGACGGT TCATGACATT    1320

GAAAAATCAA GGCTCAGCAA CCATGCCCAA GCCAATGGCT ATTATCAAGG CAATAATCTT    1380

GGTGAACGCA TTCGTGATAC CATTGGGCCA GATTCAGGTT ATGGCATCAA CTATGCTCAT    1440

GGCGTATTTT ATGATGAAAA ACACCAAAAA GACCGCCTAG GGCTTGAATA TGTTTATGAC    1500

AGCAAAGGTG AAAATAAATG GTTTGATGAT GTGCGTGTGT CTTATGATAA GCAAGACATT    1560

ACGCTACGCA GCCAGCTGAC CAACACGCAC TGTTCAACCT ATCCGCACAT TGACAAAAAT    1620

TGTACGCCTG ATGTCAATAA ACCTTTTTCG GTAAAAGAGG TGGATAACAA TGCCTACAAA    1680

GAACAGCACA ATTTAATCAA AGCCGTCTTT AACAAAAAAA TGGCGTTGGG CAGTACGCAT    1740

CATCACATCA ACCTGCAAGT TGGCTATGAT AAATTCAATT CAAGCCTGAG CCGTGAAGAT    1800

TATCGTTTGG CAACCCATCA GTCTTATGAA AAACTTGATT ACACCCCACC AAGTAACCCT    1860

TTGCCAGATA AGTTTAAGCC CATTTTAGGT TCAAACAACA AACCCATTTG CCTTGATGCT    1920

TATGGTTATG GTCATGACCA TCCACAGGCT TGTAACGCCA AAAACAGCAC TTATCAAAAT    1980

TTTGCCATCA AAAAAGGCAT AGAGCAATAC AACCAAAAAA CCAATACCGA TAAGATTGAT    2040

TATCAAGCCA TCATTGACCA ATATGATAAA CAAAACCCCA ACAGCACCCT AAAACCCTTT    2100

GAGAAAATCA AACAAAGTTT GGGGCAAGAA AAATACAACA AGATAGACGA ACTTGGCTTT    2160

AAAGCTTATA AAGATTTACG CAACGAATGG GCGGGTTGGA CTAATGACAA CAGCCAACAA    2220

AATGCCAATA AAGGCACGGA TAATATCTAT CAGCCAAATC AAGCAACTGT GGTCAAAGAT    2280

GACAAATGTA AATATAGCGA GACCAACAGC TATGCTGATT GCTCAACCAC TGCGCACATC    2340

AGTGGTGATA ATTATTTCAT CGCTTTAAAA GACAACATGA CCATCAATAA ATATGTTGAT    2400

TTGGGGCTGG GTGCTCGCTA TGACAGAATC AAACACAAAT CTGATGTGCC TTTGGTAGAC    2460

AACAGTGCCA GCAACCAGCT GTCTTGGAAT TTTGGCGTGG TCGTCAAGCC CACCAATTGG    2520

CTGGACATCG CTTATAGAAG CTCGCAAGGC TTTCGCATGC AAGTTTTTC TGAAATGTAT    2580

GGCGAACGCT TTGGCGTAAC CATCGGTAAA GGCACGCAAC ATGGCTGTAA GGGTCTTTAT    2640

TACATTTGTC AGCAGACTGT CCATCAAACC AAGCTAAAAC CTGAAAAATC CTTTAACCAA    2700

GAAATCGGAG CGACTTTACA TAACCACTTA GGCAGTCTTG AGGTTAGTTA TTTTAAAAAT    2760

CGCTATACCG ATTTGATTGT TGGTAAAAGT GAAGAGATTA GAACCCTAAC CAAGGTGAT    2820

AATGCAGGCA ACAGCGTGG TAAAGGTGAT TTGGGCTTTC ATAATGGACA AGATGCTGAT    2880

TTGACAGGCA TTAACATTCT TGGCAGACTT GACCTAAACG CTGTCAATAG TCGCCTTCCC    2940

TATGGATTAT ACTCAACACT GGCTTATAAC AAAGTTGATG TTAAAGGAAA AACCTTAAAC    3000

CCAACTTTGG CAGGAACAAA CATACTGTTT GATGCCATCC AGCCATCTCG TTATGTGGTG    3060

GGGCTTGGCT ATGATGCCCC AAGCCAAAAA TGGGGAGCAA ACGCCATATT TACCCATTCT    3120

GATGCCAAAA ATCCAAGCGA GCTTTTGGCA GATAAGAACT TAGGTAATGG CAACATTCAA    3180

ACAAAACAAG CCACCAAAGC AAAATCCACG CCGTGGCAAA CACTTGATTT GTCAGGTTAT    3240

GTAAACATAA AAGATAATTT TACCTTGCGT GCTGGCGTGT ACAATGTATT TAATACCTAT    3300

TACACCACTT GGGAGGCTTT ACGCCAAACA GCAGAAGGGG CGGTCAATCA GCATACAGGA    3360

CTGAGCCAAG ATAAGCATTA TGGTCGCTAT GCCGCTCCTG GACGCAATTA CCAATTGGCA    3420
```

-continued

```
CTTGAAATGA AGTTTTAA                                                    3438
```

(2) INFORMATION FOR SEQ ID NO:2:

(i) SEQUENCE CHARACTERISTICS:
        (A) LENGTH: 3222 base pairs
        (B) TYPE: nucleic acid
        (C) STRANDEDNESS: single
        (D) TOPOLOGY: linear (xi) SEQUENCE DESCRIPTION: SEQ ID NO:2:

```
ATGAATCAAT CAAAACAAAA CAACAAATCC AAAAAATCCA AACAAGTATT AAAACTTAGT      60

GCCTTGTCTT TGGGTCTGCT TAACATCACG CAGGTGGCAC TGGCAAACAC AACGGCCGAT     120

AAGGCGGAGG CAACAGATAA GACAAACCTT GTTGTTGTCT TGGATGAAAC TGTTGTAACA     180

GCGAAGAAAA ACGCCCGTAA AGCCAACGAA GTTACAGGGC TTGGTAAGGT GGTCAAAACT     240

GCCGAGACCA TCAATAAAGA ACAAGTGCTA AACATTCGAG ACTTAACACG CTATGACCCT     300

GGCATTGCTG TGGTTGAGCA AGGTCGTGGG GCAAGCTCAG GCTATTCTAT TCGTGGTATG     360

GATAAAAATC GTGTGGCGGT ATTGGTTGAT GGCATCAATC AAGCCCAGCA CTATGCCCTA     420

CAAGGCCCTG TGGCAGGCAA AAATTATGCC GCAGGTGGGG CAATCAACGA AATAGAATAC     480

GAAAATGTCC GCTCCGTTGA GATTAGTAAA GGTGCAAATT CAAGTGAATA CGGCTCTGGG     540

GCATTATCTG GCTCTGTGGC ATTTGTTACC AAAACCGCCG ATGACATCAT CAAAGATGGT     600

AAAGATTGGG GCGTGCAGAC CAAAACCGCC TATGCCAGTA AAAATAACGC ATGGGTTAAT     660

TCTGTGGCAG CAGCAGGCAA GGCAGGTTCT TTTAGCGGTC TTATCATCTA CACCGACCGC     720

CGTGGTCAAG AATACAAGGC ACATGATGAT GCCTATCAGG GTAGCCAAAG TTTTGATAGA     780

GCGGTGGCAA CCACTGACCC AAATAACCGA ACATTTTTAA TAGCAAATGA ATGTGCCAAT     840

GGTAATTATG AGGCGTGTGC TGCTGGCGGT CAAACCAAAC TTCAAGCCAA GCCAACCAAT     900

GTGCGTGATA AGGTCAATGT CAAAGATTAT ACAGGTCCTA ACCGCCTTAT CCCAAACCCA     960

CTCACCCAAG ACAGCAAATC CTTACTGCTT CGCCCAGGTT ATCAGCTAAA CGATAAGCAC    1020

TATGTCGGTG GTGTGTATGA AATCACCAAA CAAAACTACG CCATGCAAGA TAAAACCGTG    1080

CCTGCTTATC TGACGGTTCA TGACATTGAA AAATCAAGGC TCAGCAACCA TGCCCAAGCC    1140

AATGGCTATT ATCAAGGCAA TAATCTTGGT GAACGCATTC GTGATACCAT TGGGCCAGAT    1200

TCAGGTTATG GCATCAACTA TGCTCATGGC GTATTTTATG ATGAAAAACA CCAAAAAGAC    1260

CGCCTAGGGC TTGAATATGT TTATGACAGC AAAGGTGAAA ATAAATGGTT TGATGATGTG    1320

CGTGTGTCTT ATGATAAGCA AGACATTACG CTACGCAGCC AGCTGACCAA CACGCACTGT    1380

TCAACCTATC CGCACATTGA CAAAAATTGT ACGCCTGATG TCAATAAACC TTTTTCGGTA    1440

AAAGAGGTGG ATAACAATGC CTACAAAGAA CAGCACAATT TAATCAAAGC CGTCTTTAAC    1500

AAAAAAATGG CGTTGGGCAG TACGCATCAT CACATCAACC TGCAAGTTGG CTATGATAAA    1560

TTCAATTCAA GCCTGAGCCG TGAAGATTAT CGTTTGGCAA CCCATCAGTC TTATGAAAAA    1620

CTTGATTACA CCCCACCAAG TAACCCTTTG CCAGATAAGT TTAAGCCCAT TTTAGGTTCA    1680

AACAACAAAC CCATTTGCCT TGATGCTTAT GGTTATGGTC ATGACCATCC ACAGGCTTGT    1740

AACGCCAAAA ACAGCACTTA TCAAAATTTT GCCATCAAAA AAGGCATAGA GCAATACAAC    1800

CAAAAAACCA ATACCGATAA GATTGATTAT CAAGCCATCA TTGACCAATA TGATAAACAA    1860

AACCCCAACA GCACCCTAAA ACCCTTTGAG AAAATCAAAC AAAGTTTGGG GCAAGAAAAA    1920

TACAACAAGA TAGACGAACT TGGCTTTAAA GCTTATAAAG ATTTACGCAA CGAATGGGCG    1980
```

-continued

```
GGTTGGACTA ATGACAACAG CCAACAAAAT GCCAATAAAG GCACGGATAA TATCTATCAG    2040

CCAAATCAAG CAACTGTGGT CAAAGATGAC AAATGTAAAT ATAGCGAGAC CAACAGCTAT    2100

GCTGATTGCT CAACCACTGC GCACATCAGT GGTGATAATT ATTTCATCGC TTTAAAAGAC    2160

AACATGACCA TCAATAAATA TGTTGATTTG GGGCTGGGTG CTCGCTATGA CAGAATCAAA    2220

CACAAATCTG ATGTGCCTTT GGTAGACAAC AGTGCCAGCA ACCAGCTGTC TTGGAATTTT    2280

GGCGTGGTCG TCAAGCCCAC CAATTGGCTG GACATCGCTT ATAGAAGCTC GCAAGGCTTT    2340

CGCATGCCAA GTTTTTCTGA AATGTATGGC GAACGCTTTG GCGTAACCAT CGGTAAAGGC    2400

ACGCAACATG GCTGTAAGGG TCTTTATTAC ATTTGTCAGC AGACTGTCCA TCAAACCAAG    2460

CTAAAACCTG AAAAATCCTT TAACCAAGAA ATCGGAGCGA CTTTACATAA CCACTTAGGC    2520

AGTCTTGAGG TTAGTTATTT TAAAAATCGC TATACCGATT TGATTGTTGG TAAAAGTGAA    2580

GAGATTAGAA CCCTAACCCA AGGTGATAAT GCAGGCAAAC AGCGTGGTAA AGGTGATTTG    2640

GGCTTTCATA ATGGACAAGA TGCTGATTTG ACAGGCATTA ACATTCTTGG CAGACTTGAC    2700

CTAAACGCTG TCAATAGTCG CCTTCCCTAT GGATTATACT CAACACTGGC TTATAACAAA    2760

GTTGATGTTA AAGGAAAAAC CTTAAACCCA ACTTTGGCAG GAACAAACAT ACTGTTTGAT    2820

GCCATCCAGC CATCTCGTTA TGTGGTGGGG CTTGGCTATG ATGCCCCAAG CCAAAAATGG    2880

GGAGCAAACG CCATATTTAC CCATTCTGAT GCCAAAAATC CAAGCGAGCT TTTGGCAGAT    2940

AAGAACTTAG GTAATGGCAA CATTCAAACA AAACAAGCCA CCAAAGCAAA ATCCACGCCG    3000

TGGCAAACAC TTGATTTGTC AGGTTATGTA AACATAAAAG ATAATTTTAC CTTGCGTGCT    3060

GGCGTGTACA ATGTATTTAA TACCTATTAC ACCACTTGGG AGGCTTTACG CCAAACAGCA    3120

GAAGGGCGG TCAATCAGCA TACAGGACTG AGCCAAGATA AGCATTATGG TCGCTATGCC    3180

GCTCCTGGAC GCAATTACCA ATTGGCACTT GAAATGAAGT TT    3222
```

(2) INFORMATION FOR SEQ ID NO:3:

(i) SEQUENCE CHARACTERISTICS:
        (A) LENGTH: 2247 base pairs
        (B) TYPE: nucleic acid
        (C) STRANDEDNESS: single
        (D) TOPOLOGY: linear (xi) SEQUENCE DESCRIPTION: SEQ ID NO:3:

```
GTAAATTTGC CGTATTTTGT CTATCATAAA TGCATTTATC AAATGCTCAA ATAAATACGC     60

AAATGCACAT TGTCAGCATG CCAAAATAGG CATCAACAGA CTTTTTTAGA TAATACCATC    120

AACCCATCAG AGGATTATTT TATGAAACAC ATTCCTTTAA CCACACTGTG TGTGGCAATC    180

TCTGCCGTCT TATTAACCGC TTGTGGTGGC AGTGGTGGTT CAAATCCACC TGCTCCTACG    240

CCCATTCCAA ATGCTAGCGG TTCAGGTAAT ACTGGCAACA CTGGTAATGC TGGCGGTACT    300

GATAATACAG CCAATGCAGG TAATACAGGC GGTACAAACT CTGGTACAGG CAGTGCCAAC    360

ACACCAGAGC CAAAATATCA AGATGTACCA ACTGAGAAAA ATGAAAAAGA TAAAGTTTCA    420

TCCATTCAAG AACCTGCCAT GGGTTATGGC ATGGCTTTGA GTAAAATTAA TCTACACAAC    480

CGACAAGACA CGCCATTAGA TGAAAAAAAT ATCATTACCT TAGACGGTAA AAAACAAGTT    540

GCAGAAGGTA AAAAATCGCC ATTGCCATTT TCGTTAGATG TAGAAAATAA ATTGCTTGAT    600

GGCTATATAG CAAAAATGAA TGTAGCGGAT AAAAATGCCA TTGGTGACAG AATTAAGAAA    660

GGTAATAAAG AAATCTCCGA TGAAGAACTT GCCAACAAA TCAAAGAAGC TGTGCGTAAA    720

AGCCATGAGT TTCAGCAAGT ATTATCATCA CTGGAAAACA AAATTTTTCA TTCAAATGAC    780
```

```
GGAACAACCA AAGCAACCAC ACGAGATTTA AAATATGTTG ATTATGGTTA CTACTTGGCG      840

AATGATGGCA ATTATCTAAC CGTCAAAACA GACAAACTTT GGAATTTAGG CCCTGTGGGT      900

GGTGTGTTTT ATAATGGCAC AACGACCGCC AAAGAGTTGC CCACACAAGA TGCGGTCAAA      960

TATAAAGGAC ATTGGGACTT TATGACCGAT GTTGCCAACA GAAGAAACCG ATTTAGCGAA     1020

GTGAAAGAAA ACTCTCAAGC AGGCTGGTAT TATGGAGCAT CTTCAAAAGA TGAATACAAC     1080

CGCTTATTAA CTAAAGAAGA CTCTGCCCCT GATGGTCATA GCGGTGAATA TGGCCATAGC     1140

AGTGAGTTTA CTGTTAATTT TAAGGAAAAA AAATTAACAG GTAAGCTGTT TAGTAACCTA     1200

CAAGACCGCC ATAAGGGCAA TGTTACAAAA ACCGAACGCT ATGACATCGA TGCCAATATC     1260

CACGGCAACC GCTTCCGTGG CAGTGCCACC GCAAGCAATA AAAATGACAC AAGCAAACAC     1320

CCCTTTACCA GTGATGCCAA CAATAGGCTA GAAGGTGGTT TTTATGGGCC AAAAGGCGAG     1380

GAGCTGGCAG GTAAATTCTT AACCAATGAC AACAAACTCT TTGGCGTCTT TGGTGCTAAA     1440

CGAGAGAGTA AAGCTGAGGA AAAAACCGAA GCCATCTTAG ATGCCTATGC ACTTGGGACA     1500

TTTAATACAA GTAACGCAAC CACATTCACC CCATTTACCG AAAAACAACT GGATAACTTT     1560

GGCAATGCCA AAAAATTGGT CTTAGGTTCT ACCGTCATTG ATTTGGTGCC TACTGATGCC     1620

ACCAAAAATG AATTCACCAA AGACAAGCCA GAGTCTGCCA CAAACGAAGC GGGCGAGACT     1680

TTGATGGTGA ATGATGAAGT TAGCGTCAAA ACCTATGGCA AAAACTTTGA ATACCTAAAA     1740

TTTGGTGAGC TTAGTATCGG TGGTAGCCAT AGCGTCTTTT TACAAGGCGA ACGCACCGCT     1800

ACCACAGGCG AGAAAGCCGT ACCAACCACA GGCACAGCCA ATATTTGGG GAACTGGGTA      1860

GGATACATCA CAGGAAAGGA CACAGGAACG GGCACAGGAA AAAGCTTTAC CGATGCCCAA     1920

GATGTTGCTG ATTTTGACAT TGATTTTGGA AATAAATCAG TCAGCGGTAA ACTTATCACC     1980

AAAGGCCGCC AAGACCCTGT ATTTAGCATC ACAGGTCAAA TCGCAGGCAA TGGCTGGACA     2040

GGCACAGCCA GCACCACCAA AGCGGACGCA GGAGGCTACA AGATAGATTC TAGCAGTACA     2100

GGCAAATCCA TCGTCATCAA AGATGCCAAT GTTACAGGGG GCTTTTATGG TCCAAATGCA     2160

AACGAGATGG GCGGGTCATT TACACACAAC GCCGATGACA GCAAAGCCTC TGTGGTCTTT     2220

GGCACAAAAA GACAACAAGA AGTTAAG                                         2247

(2) INFORMATION FOR SEQ ID NO:4:

(i) SEQUENCE CHARACTERISTICS:
         (A) LENGTH: 2106 base pairs
         (B) TYPE: nucleic acid
         (C) STRANDEDNESS: single
         (D) TOPOLOGY: linear (xi) SEQUENCE DESCRIPTION: SEQ ID NO:4:

ATGAAACACA TTCCTTTAAC CACACTGTGT GTGGCAATCT CTGCCGTCTT ATTAACCGCT       60

TGTGGTGGCA GTGGTGGTTC AAATCCACCT GCTCCTACGC CCATTCCAAA TGCTAGCGGT      120

TCAGGTAATA CTGGCAACAC TGGTAATGCT GGCGGTACTG ATAATACAGC CAATGCAGGT      180

AATACAGGCG GTACAAACTC TGGTACAGGC AGTGCCAACA CACCAGAGCC AAAATATCAA      240

GATGTACCAA CTGAGAAAAA TGAAAAAGAT AAAGTTTCAT CCATTCAAGA ACCTGCCATG      300

GGTTATGGCA TGGCTTTGAG TAAAATTAAT CTACACAACC GACAAGACAC GCCATTAGAT      360

GAAAAAAATA TCATTACCTT AGACGGTAAA AACAAGTTG CAGAAGGTAA AAAATCGCCA       420

TTGCCATTTT CGTTAGATGT AGAAAATAAA TTGCTTGATG GCTATATAGC AAAAATGAAT      480

GTAGCGGATA AAAATGCCAT TGGTGACAGA ATTAAGAAAG GTAATAAAGA AATCTCCGAT      540
```

```
GAAGAACTTG CCAAACAAAT CAAAGAAGCT GTGCGTAAAA GCCATGAGTT TCAGCAAGTA      600

TTATCATCAC TGGAAAACAA AATTTTTCAT TCAAATGACG GAACAACCAA AGCAACCACA      660

CGAGATTTAA AATATGTTGA TTATGGTTAC TACTTGGCGA ATGATGGCAA TTATCTAACC      720

GTCAAAACAG ACAAACTTTG GAATTTAGGC CCTGTGGGTG GTGTGTTTTA TAATGGCACA      780

ACGACCGCCA AAGAGTTGCC CACACAAGAT GCGGTCAAAT ATAAAGGACA TTGGGACTTT      840

ATGACCGATG TTGCCAACAG AAGAAACCGA TTTAGCGAAG TGAAAGAAAA CTCTCAAGCA      900

GGCTGGTATT ATGGAGCATC TTCAAAAGAT GAATACAACC GCTTATTAAC TAAAGAAGAC      960

TCTGCCCCTG ATGGTCATAG CGGTGAATAT GGCCATAGCA GTGAGTTTAC TGTTAATTTT     1020

AAGGAAAAAA AATTAACAGG TAAGCTGTTT AGTAACCTAC AAGACCGCCA TAAGGGCAAT     1080

GTTACAAAAA CCGAACGCTA TGACATCGAT GCCAATATCC ACGGCAACCG CTTCCGTGGC     1140

AGTGCCACCG CAAGCAATAA AAATGACACA AGCAAACACC CCTTTACCAG TGATGCCAAC     1200

AATAGGCTAG AAGGTGGTTT TTATGGGCCA AAAGGCGAGG AGCTGGCAGG TAAATTCTTA     1260

ACCAATGACA ACAAACTCTT TGGCGTCTTT GGTGCTAAAC GAGAGAGTAA AGCTGAGGAA     1320

AAAACCGAAG CCATCTTAGA TGCCTATGCA CTTGGGACAT TTAATACAAG TAACGCAACC     1380

ACATTCACCC CATTTACCGA AAAACAACTG GATAACTTTG GCAATGCCAA AAAATTGGTC     1440

TTAGGTTCTA CCGTCATTGA TTTGGTGCCT ACTGATGCCA CCAAAAATGA ATTCACCAAA     1500

GACAAGCCAG AGTCTGCCAC AAACGAAGCG GGCGAGACTT TGATGGTGAA TGATGAAGTT     1560

AGCGTCAAAA CCTATGGCAA AAACTTTGAA TACCTAAAAT TTGGTGAGCT TAGTATCGGT     1620

GGTAGCCATA GCGTCTTTTT ACAAGGCGAA CGCACCGCTA CCACAGGCGA GAAAGCCGTA     1680

CCAACCACAG GCACAGCCAA ATATTTGGGG AACTGGGTAG GATACATCAC AGGAAAGGAC     1740

ACAGGAACGG GCACAGGAAA AAGCTTTACC GATGCCCAAG ATGTTGCTGA TTTTGACATT     1800

GATTTTGGAA ATAAATCAGT CAGCGGTAAA CTTATCACCA AAGGCCGCCA AGACCCTGTA     1860

TTTAGCATCA CAGGTCAAAT CGCAGGCAAT GGCTGGACAG GCACAGCCAG CACCACCAAA     1920

GCGGACGCAG GAGGCTACAA GATAGATTCT AGCAGTACAG GCAAATCCAT CGTCATCAAA     1980

GATGCCAATG TTACAGGGGG CTTTTATGGT CCAAATGCAA ACGAGATGGG CGGGTCATTT     2040

ACACACAACG CCGATGACAG CAAAGCCTCT GTGGTCTTTG GCACAAAAAG ACAACAAGAA     2100

GTTAAG                                                               2106
```

(2) INFORMATION FOR SEQ ID NO:5:

(i) SEQUENCE CHARACTERISTICS:
        (A) LENGTH: 3660 base pairs
        (B) TYPE: nucleic acid
        (C) STRANDEDNESS: single
        (D) TOPOLOGY: linear (xi) SEQUENCE DESCRIPTION: SEQ ID NO:5:

```
AATTGATACA AAATGGTTTG TATTATCACT TGTATTTGTA TTATAATTTT ACTTATTTTT       60

ACAAACTATA CACTAAAATC AAAAATTAAT CACTTTGGTT GGGTGGTTTT AGCAAGCAAA      120

TGGTTATTTT GGTAAACAAT TAAGTTCTTA AAAACGATAC ACGCTCATAA ACAGATGGTT      180

TTTGGCATCT TCAATTTGAT GCCTGCCTTG TGATTGGTTG GGGGTGTATT GATGTATCCA      240

AGTACAAAAG CCAACAGGTG GTCATTGATG AATCAATCCA AAAAATCCAA AAATCCAAA      300

CAAGTATTAA AACTTAGTGC CTTGTCTTTG GGTCTGCTTA ACATCACGCA GGTGGCACTG      360

GCAAACACAA CGGCCGATAA GGCGGAGGCA ACAGATAAGA CAAACCTTGT TGTTGTCTTG      420
```

```
GATGAAACTG TTGTAACAGC GAAGAAAAAC GCCCGTAAAG CCAACGAAGT TACAGGGCTT    480

GGTAAGGTGG TCAAAACTGC CGAGACCATC AATAAAGAAC AAGTGCTAAA CATTCGAGAC    540

TTAACACGCT ATGACCCTGG CATTGCTGTG GTTGAGCAAG GTCGTGGGGC AAGCTCAGGC    600

TATTCTATTC GTGGTATGGA TAAAAATCGT GTGGCGGTAT TGGTTGATGG CATCAATCAA    660

GCCCAGCACT ATGCCCTACA AGGCCCTGTG GCAGGCAAAA ATTATGCCGC AGGTGGGGCA    720

ATCAACGAAA TAGAATACGA AAATGTCCGC TCCGTTGAGA TTAGTAAAGG TGCAAATTCA    780

AGTGAATACG GCTCTGGGGC ATTATCTGGC TCTGTGGCAT TTGTTACCAA AACCGCCGAT    840

GACATCATCA AAGATGGTAA AGATTGGGGC GTGCAGACCA AAACCGCCTA TGCCAGTAAA    900

AATAACGCAT GGGTTAATTC TGTGGCAGCA GCAGGCAAGG CAGGTTCTTT TAGCGGTCTT    960

ATCATCTACA CCGACCGCCG TGGTCAAGAA TACAAGGCAC ATGATGATGC CTATCAGGGT   1020

AGCCAAAGTT TTGATAGAGC GGTGGCAACC ACTGACCCAA ATAACCCAAA ATTTTTAATA   1080

GCAAATGAAT GTGCCAATGG TAATTATGAG GCGTGTGCTG CTGGCGGTCA AACCAAACTC   1140

CAAGCTAAGC CAACCAATGT GCGTGATAAG GTCAATGTCA AAGATTATAC AGGTCCTAAC   1200

CGCCTTATCC CAAACCCACT CACCCAAGAC AGCAAATCCT TACTGCTTCG CCCAGGTTAT   1260

CAGCTAAACG ATAAGCACTA TGTCGGTGGT GTGTATGAAA TCACCAAACA AAACTACGCC   1320

ATGCAAGATA AAACCGTGCC TGCTTATCTG ACGGTTCATG ACATTGAAAA ATCAAGGCTC   1380

AGCAACCATG GCCAAGCCAA TGGCTATTAT CAAGGCAATA ACCTTGGTGA ACGCATTCGT   1440

GATGCCATTG GGCAAATTC AGGTTATGGC ATCAACTATG CTCATGGCGT ATTTTATGAC   1500

GAAAACACC AAAAAGACCG CCTAGGGCTT GAATATGTTT ATGACAGCAA AGGTGAAAAT   1560

AAATGGTTTG ATGATGTGCG TGTGTCTTAT GACAAGCAAG ACATTACGCT ACGTAGCCAG   1620

CTGACCAACA CGCACTGTTC AACCTATCCG CACATTGACA AAAATTGTAC GCCTGATGTC   1680

AATAAACCTT TTTCGGTAAA AGAGGTGGAT AACAATGCCT ACAAAGAACA GCACAATTTA   1740

ATCAAAGCCG TCTTTAACAA AAAAATGGCA TTGGGCAATA CGCATCATCA CATCAATCTG   1800

CAAGTTGGCT ATGATAAATT CAATTCAAGC CTTAGCCGTG AAGATTATCG TTTGGCAACC   1860

CATCAATCTT ATCAAAAACT TGATTACACC CCACCAAGTA ACCCTTTGCC AGATAAGTTT   1920

AAGCCCATTT TAGGTTCAAA CAACAGACCC ATTTGCCTTG ATGCTTATGG TTATGGTCAT   1980

GACCATCCAC AGGCTTGTAA CGCCAAAAAC AGCACTTATC AAAACTTTGC CATCAAAAAA   2040

GGCATAGAGC AATACAACCA AACCAATACC GATAAGATTG ATTATCAAGC CGTCATTGAC   2100

CAATATGATA AACAAAACCC CAACAGCACC CTAAAACCCT TGAGAAAAAT CAAACAAAGT   2160

TTGGGGCAAG AAAAATACGA CGAGATAGAC AGACTGGGCT TTAATGCTTA TAAAGATTTA   2220

CGCAACGAAT GGGCGGGTTG GACTAATGAC AACAGCCAAC AAAACGCCAA TAAAGGCACG   2280

GATAATATCT ATCAGCCAAA TCAAGCAACT GTGGTCAAAG ATGACAAATG TAAATATAGC   2340

GAGACCAACA GCTATGCTGA TTGCTCAACC ACTCGCCACA TCAGCGGTGA TAATTATTTC   2400

ATCGCTTTAA AAGACAACAT GACCATCAAT AAATATGTTG ATTTGGGGCT GGGTGCTCGC   2460

TATGACAGAA TCAAACACAA ATCTGATGTG CCTTTGGTAG ACAACAGTGC CAGCAACCAG   2520

CTGTCTTGGA ATTTTGGCGT GGTCGTCAAG CCCACCAATT GGCTGGACAT CGCTTATAGA   2580

AGCTCGCAAG GCTTTCGCAT GCCAAGTTTT TCTGAAATGT ATGGCGAACG CTTTGGCGTA   2640

ACCATCGGTA AAGGCACGCA ACATGGCTGT AAGGGTCTTT ATTACATTTG TCAGCAGACT   2700

GTCCATCAAA CCAAGCTAAA ACCTGAAAAA TCCTTTAACC AAGAAATCGG AGCGACTTTA   2760
```

-continued

| | |
|---|---|
| CATAACCACT TAGGCAGTCT TGAGGTTAGT TATTTTAAAA ATCGCTATAC CGATTTGATT | 2820 |
| GTTGGTAAAA GTGAAGAGAT TAGAACCCTA ACCCAAGGTG ATAATGCAGG CAAACAGCGT | 2880 |
| GGTAAAGGTG ATTTGGGCTT TCATAATGGG CAAGATGCTG ATTTGACAGG CATTAACATT | 2940 |
| CTTGGCAGAC TTGACCTAAA CGCTGTCAAT AGTCGCCTTC CCTATGGATT ATACTCAACA | 3000 |
| CTGGCTTATA ACAAAGTTGA TGTTAAAGGA AAAACCTTAA ACCCAACTTT GGCAGGAACA | 3060 |
| AACATACTGT TTGATGCCAT TCAGCCATCT CGTTATGTGG TGGGGCTTGG CTATGATGCC | 3120 |
| CCAAGCCAAA AATGGGGAGC AAACGCCATA TTTACCCATT CTGATGCCAA AAATCCAAGC | 3180 |
| GAGCTTTTGG CAGATAAGAA CTTAGGTAAT GGCAACAATC AAACAAAACA AGCCACCAAA | 3240 |
| GCAAAATCCA CGCCGTGGCA AACACTTGAT TTGTCAGGTT ATGTAAACAT AAAAGATAAT | 3300 |
| TTTACCTTGC GTGCTGGCGT GTACAATGTA TTTAATACCT ATTACACCAC TTGGGAGGCT | 3360 |
| TTACGCCAAA CAGCAGAAGG GGCGGTCAAT CAGCATACAG GACTGAGCCA AGATAAGCAT | 3420 |
| TATGGTCGCT ATGCCGCTCC TGGACGCAAT TACCAATTGG CACTTGAAAT GAAGTTTTAA | 3480 |
| CCAGTGGCTT TGATGTGATC ATGCCAAATC CCAATCAACC AATGAATAAA GCCCCCATCT | 3540 |
| ACCATGAGGG CTTTATTTTA TCATCGCTGA GTATGCTCTT AGCGGTCATC ACTCAGATTA | 3600 |
| GTCATTAATT TATTAGCGAT TAATTTATTA GTAATCACGC TGCTCTTTGA TGATTTTAAG | 3660 |

(2) INFORMATION FOR SEQ ID NO:6:

(i) SEQUENCE CHARACTERISTICS:
        (A) LENGTH: 3210 base pairs
        (B) TYPE: nucleic acid
        (C) STRANDEDNESS: single
        (D) TOPOLOGY: linear (xi) SEQUENCE DESCRIPTION: SEQ ID NO:6:

| | |
|---|---|
| ATGAATCAAT CCAAAAAATC CAAAAAATCC AAACAAGTAT TAAAACTTAG TGCCTTGTCT | 60 |
| TTGGGTCTGC TTAACATCAC GCAGGTGGCA CTGGCAAACA CAACGGCCGA TAAGGCGGAG | 120 |
| GCAACAGATA AGACAAACCT TGTTGTTGTC TTGGATGAAA CTGTTGTAAC AGCGAAGAAA | 180 |
| AACGCCCGTA AAGCCAACGA AGTTACAGGG CTTGGTAAGG TGGTCAAAAC TGCCGAGACC | 240 |
| ATCAATAAAG AACAAGTGCT AAACATTCGA GACTTAACAC GCTATGACCC TGGCATTGCT | 300 |
| GTGGTTGAGC AAGGTCGTGG GGCAAGCTCA GGCTATTCTA TTCGTGGTAT GGATAAAAAT | 360 |
| CGTGTGGCGG TATTGGTTGA TGGCATCAAT CAAGCCCAGC ACTATGCCCT ACAAGGCCCT | 420 |
| GTGGCAGGCA AAAATTATGC CGCAGGTGGG GCAATCAACG AAATAGAATA CGAAAATGTC | 480 |
| CGCTCCGTTG AGATTAGTAA AGGTGCAAAT TCAAGTGAAT ACGGCTCTGG GGCATTATCT | 540 |
| GGCTCTGTGG CATTTGTTAC CAAAACCGCC GATGACATCA TCAAAGATGG TAAAGATTGG | 600 |
| GGCGTGCAGA CCAAAACCGC CTATGCCAGT AAAAATAACG CATGGGTTAA TTCTGTGGCA | 660 |
| GCAGCAGGCA AGGCAGGTTC TTTTAGCGGT CTTATCATCT ACACCGACCG CCGTGGTCAA | 720 |
| GAATACAAGG CACATGATGA TGCCTATCAG GGTAGCCAAA GTTTTGATAG AGCGGTGGCA | 780 |
| ACCACTGACC CAAATAACCC AAAATTTTTA ATAGCAAATG AATGTGCCAA TGGTAATTAT | 840 |
| GAGGCGTGTG CTGCTGGCGG TCAAACCAAA CTCCAAGCTA AGCCAACCAA TGTGCGTGAT | 900 |
| AAGGTCAATG TCAAAGATTA TACAGGTCCT AACCGCCTTA TCCCAAACCC ACTCACCCAA | 960 |
| GACAGCAAAT CCTTACTGCT TCGCCCAGGT TATCAGCTAA ACGATAAGCA CTATGTCGGT | 1020 |
| GGTGTGTATG AAATCACCAA ACAAAACTAC GCCATGCAAG ATAAAACCGT GCCTGCTTAT | 1080 |
| CTGACGGTTC ATGACATTGA AAAATCAAGG CTCAGCAACC ATGCCAAGC CAATGGCTAT | 1140 |

```
TATCAAGGCA ATAACCTTGG TGAACGCATT CGTGATGCCA TTGGGGCAAA TTCAGGTTAT    1200

GGCATCAACT ATGCTCATGG CGTATTTTAT GACGAAAAAC ACCAAAAAGA CCGCCTAGGG    1260

CTTGAATATG TTTATGACAG CAAAGGTGAA AATAAATGGT TTGATGATGT GCGTGTGTCT    1320

TATGACAAGC AAGACATTAC GCTACGTAGC CAGCTGACCA ACACGCACTG TTCAACCTAT    1380

CCGCACATTG ACAAAAATTG TACGCCTGAT GTCAATAAAC CTTTTTCGGT AAAAGAGGTG    1440

GATAACAATG CCTACAAAGA ACAGCACAAT TTAATCAAAG CCGTCTTTAA CAAAAAAATG    1500

GCATTGGGCA ATACGCATCA TCACATCAAT CTGCAAGTTG CTATGATAAA ATTCAATTCA    1560

AGCCTTAGCC GTGAAGATTA TCGTTTGGCA ACCCATCAAT CTTATCAAAA ACTTGATTAC    1620

ACCCCACCAA GTAACCCTTT GCCAGATAAG TTTAAGCCCA TTTTAGGTTC AAACAACAGA    1680

CCCATTTGCC TTGATGCTTA TGGTTATGGT CATGACCATC CACAGGCTTG TAACGCCAAA    1740

AACAGCACTT ATCAAAACTT TGCCATCAAA AAAGGCATAG AGCAATACAA CCAAACCAAT    1800

ACCGATAAGA TTGATTATCA AGCCGTCATT GACCAATATG ATAAACAAAA CCCCAACAGC    1860

ACCCTAAAAC CCTTTGAGAA AATCAAACAA AGTTTGGGGC AAGAAAAATA CGACGAGATA    1920

GACAGACTGG GCTTTAATGC TTATAAAGAT TTACGCAACG AATGGGCGGG TTGGACTAAT    1980

GACAACAGCC AACAAAACGC CAATAAAGGC ACGGATAATA TCTATCAGCC AAATCAAGCA    2040

ACTGTGGTCA AGATGACAA ATGTAAATAT AGCGAGACCA ACAGCTATGC TGATTGCTCA    2100

ACCACTCGCC ACATCAGCGG TGATAATTAT TTCATCGCTT TAAAAGACAA CATGACCATC    2160

AATAAATATG TTGATTTGGG GCTGGGTGCT CGCTATGACA GAATCAAACA CAAATCTGAT    2220

GTGCCTTTGG TAGACAACAG TGCCAGCAAC CAGCTGTCTT GGAATTTTGG CGTGGTCGTC    2280

AAGCCCACCA ATTGGCTGGA CATCGCTTAT AGAAGCTCGC AAGGCTTTCG CATGCCAAGT    2340

TTTTCTGAAA TGTATGGCGA ACGCTTTGGC GTAACCATCG GTAAAGGCAC GCAACATGGC    2400

TGTAAGGGTC TTTATTACAT TTGTCAGCAG ACTGTCCATC AAACCAAGCT AAAACCTGAA    2460

AAATCCTTTA ACCAAGAAAT CGGAGCGACT TTACATAACC ACTTAGGCAG TCTTGAGGTT    2520

AGTTATTTTA AAAATCGCTA TACCGATTTG ATTGTTGGTA AAAGTGAAGA GATTAGAACC    2580

CTAACCCAAG GTGATAATGC AGGCAAACAG CGTGGTAAAG GTGATTTGGG CTTTCATAAT    2640

GGGCAAGATG CTGATTTGAC AGGCATTAAC ATTCTTGGCA GACTTGACCT AAACGCTGTC    2700

AATAGTCGCC TTCCCTATGG ATTATACTCA ACACTGGCTT ATAACAAAGT TGATGTTAAA    2760

GGAAAAACCT TAAACCCAAC TTTGGCAGGA ACAAACATAC TGTTTGATGC CATTCAGCCA    2820

TCTCGTTATG TGGTGGGGCT TGGCTATGAT GCCCCAAGCC AAAAATGGGG AGCAAACGCC    2880

ATATTTACCC ATTCTGATGC CAAAAATCCA AGCGAGCTTT TGGCAGATAA GAACTTAGGT    2940

AATGGCAACA ATCAAACAAA ACAAGCCACC AAAGCAAAAT CCACGCCGTG GCAAACACTT    3000

GATTTGTCAG GTTATGTAAA CATAAAAGAT AATTTTACCT TGCGTGCTGG CGTGTACAAT    3060

GTATTTAATA CCTATTACAC CACTTGGGAG GCTTTACGCC AAACAGCAGA AGGGGCGGTC    3120

AATCAGCATA CAGGACTGAG CCAAGATAAG CATTATGGTC GCTATGCCGC TCCTGGACGC    3180

AATTACCAAT TGGCACTTGA AATGAAGTTT                                    3210

(2) INFORMATION FOR SEQ ID NO:7:

(i) SEQUENCE CHARACTERISTICS:
         (A) LENGTH: 1074 amino acids
         (B) TYPE: amino acid
         (C) STRANDEDNESS: single
         (D) TOPOLOGY: linear
```

(xi) SEQUENCE DESCRIPTION: SEQ ID NO:7:

```
Met Asn Gln Ser Lys Gln Asn Asn Lys Ser Lys Lys Ser Lys Gln Val
 1               5                   10                  15

Leu Lys Leu Ser Ala Leu Ser Leu Gly Leu Leu Asn Ile Thr Gln Val
                20                  25                  30

Ala Leu Ala Asn Thr Thr Ala Asp Lys Ala Glu Ala Thr Asp Lys Thr
            35                  40                  45

Asn Leu Val Val Val Leu Asp Glu Thr Val Val Thr Ala Lys Lys Asn
 50                  55                  60

Ala Arg Lys Ala Asn Glu Val Thr Gly Leu Gly Lys Val Val Lys Thr
 65                  70                  75                  80

Ala Glu Thr Ile Asn Lys Glu Gln Val Leu Asn Ile Arg Asp Leu Thr
                85                  90                  95

Arg Tyr Asp Pro Gly Ile Ala Val Val Glu Gln Gly Arg Gly Ala Ser
                100                 105                 110

Ser Gly Tyr Ser Ile Arg Gly Met Asp Lys Asn Arg Val Ala Val Leu
            115                 120                 125

Val Asp Gly Ile Asn Gln Ala Gln His Tyr Ala Leu Gln Gly Pro Val
130                 135                 140

Ala Gly Lys Asn Tyr Ala Ala Gly Ala Ile Asn Glu Ile Glu Tyr
145                 150                 155                 160

Glu Asn Val Arg Ser Val Glu Ile Ser Lys Gly Ala Asn Ser Ser Glu
                165                 170                 175

Tyr Gly Ser Gly Ala Leu Ser Gly Ser Val Ala Phe Val Thr Lys Thr
            180                 185                 190

Ala Asp Asp Ile Ile Lys Asp Gly Lys Asp Trp Gly Val Gln Thr Lys
            195                 200                 205

Thr Ala Tyr Ala Ser Lys Asn Asn Ala Trp Val Asn Ser Val Ala Ala
210                 215                 220

Ala Gly Lys Ala Gly Ser Phe Ser Gly Leu Ile Ile Tyr Thr Asp Arg
225                 230                 235                 240

Arg Gly Gln Glu Tyr Lys Ala His Asp Asp Ala Tyr Gln Gly Ser Gln
                245                 250                 255

Ser Phe Asp Arg Ala Val Ala Thr Thr Asp Pro Asn Asn Arg Thr Phe
            260                 265                 270

Leu Ile Ala Asn Glu Cys Ala Asn Gly Asn Tyr Glu Ala Cys Ala Ala
            275                 280                 285

Gly Gly Gln Thr Lys Leu Gln Ala Lys Pro Thr Asn Val Arg Asp Lys
290                 295                 300

Val Asn Val Lys Asp Tyr Thr Gly Pro Asn Arg Leu Ile Pro Asn Pro
305                 310                 315                 320

Leu Thr Gln Asp Ser Lys Ser Leu Leu Leu Arg Pro Gly Tyr Gln Leu
                325                 330                 335

Asn Asp Lys His Tyr Val Gly Val Tyr Glu Ile Thr Lys Gln Asn
            340                 345                 350

Tyr Ala Met Gln Asp Lys Thr Val Pro Ala Tyr Leu Thr Val His Asp
            355                 360                 365

Ile Glu Lys Ser Arg Leu Ser Asn His Ala Gln Ala Asn Gly Tyr Tyr
            370                 375                 380

Gln Gly Asn Asn Leu Gly Glu Arg Ile Arg Asp Thr Ile Gly Pro Asp
385                 390                 395                 400

Ser Gly Tyr Gly Ile Asn Tyr Ala His Gly Val Phe Tyr Asp Glu Lys
                405                 410                 415
```

-continued

His Gln Lys Asp Arg Leu Gly Leu Glu Tyr Val Tyr Asp Ser Lys Gly
             420                 425                 430

Glu Asn Lys Trp Phe Asp Asp Val Arg Val Ser Tyr Asp Lys Gln Asp
             435                 440                 445

Ile Thr Leu Arg Ser Gln Leu Thr Asn Thr His Cys Ser Thr Tyr Pro
             450                 455                 460

His Ile Asp Lys Asn Cys Thr Pro Asp Val Asn Lys Pro Phe Ser Val
465                 470                 475                 480

Lys Glu Val Asp Asn Asn Ala Tyr Lys Glu Gln His Asn Leu Ile Lys
                 485                 490                 495

Ala Val Phe Asn Lys Lys Met Ala Leu Gly Ser Thr His His Ile
             500                 505                 510

Asn Leu Gln Val Gly Tyr Asp Lys Phe Asn Ser Ser Leu Ser Arg Glu
             515                 520                 525

Asp Tyr Arg Leu Ala Thr His Gln Ser Tyr Glu Lys Leu Asp Tyr Thr
             530                 535                 540

Pro Pro Ser Asn Pro Leu Pro Asp Lys Phe Lys Pro Ile Leu Gly Ser
545                 550                 555                 560

Asn Asn Lys Pro Ile Cys Leu Asp Ala Tyr Gly Tyr Gly His Asp His
             565                 570                 575

Pro Gln Ala Cys Asn Ala Lys Asn Ser Thr Tyr Gln Asn Phe Ala Ile
             580                 585                 590

Lys Lys Gly Ile Glu Gln Tyr Asn Gln Lys Thr Asn Thr Asp Lys Ile
             595                 600                 605

Asp Tyr Gln Ala Ile Ile Asp Gln Tyr Asp Lys Gln Asn Pro Asn Ser
             610                 615                 620

Thr Leu Lys Pro Phe Glu Lys Ile Lys Gln Ser Leu Gly Gln Glu Lys
625                 630                 635                 640

Tyr Asn Lys Ile Asp Glu Leu Gly Phe Lys Ala Tyr Lys Asp Leu Arg
             645                 650                 655

Asn Glu Trp Ala Gly Trp Thr Asn Asp Asn Ser Gln Gln Asn Ala Asn
             660                 665                 670

Lys Gly Thr Asp Asn Ile Tyr Gln Pro Asn Gln Ala Thr Val Val Lys
             675                 680                 685

Asp Asp Lys Cys Lys Tyr Ser Glu Thr Asn Ser Tyr Ala Asp Cys Ser
             690                 695                 700

Thr Thr Ala His Ile Ser Gly Asp Asn Tyr Phe Ile Ala Leu Lys Asp
705                 710                 715                 720

Asn Met Thr Ile Asn Lys Tyr Val Asp Leu Gly Leu Gly Ala Arg Tyr
             725                 730                 735

Asp Arg Ile Lys His Lys Ser Asp Val Pro Leu Val Asp Asn Ser Ala
             740                 745                 750

Ser Asn Gln Leu Ser Trp Asn Phe Gly Val Val Lys Pro Thr Asn
             755                 760                 765

Trp Leu Asp Ile Ala Tyr Arg Ser Ser Gln Gly Phe Arg Met Pro Ser
             770                 775                 780

Phe Ser Glu Met Tyr Gly Glu Arg Phe Gly Val Thr Ile Gly Lys Gly
785                 790                 795                 800

Thr Gln His Gly Cys Lys Gly Leu Tyr Tyr Ile Cys Gln Gln Thr Val
             805                 810                 815

His Gln Thr Lys Leu Lys Pro Glu Lys Ser Phe Asn Gln Glu Ile Gly
             820                 825                 830

```
Ala Thr Leu His Asn His Leu Gly Ser Leu Glu Val Ser Tyr Phe Lys
            835                 840                 845

Asn Arg Tyr Thr Asp Leu Ile Val Gly Lys Ser Glu Glu Ile Arg Thr
        850                 855                 860

Leu Thr Gln Gly Asp Asn Ala Gly Lys Gln Arg Gly Lys Gly Asp Leu
865                 870                 875                 880

Gly Phe His Asn Gly Gln Asp Ala Asp Leu Thr Gly Ile Asn Ile Leu
                885                 890                 895

Gly Arg Leu Asp Leu Asn Ala Val Asn Ser Arg Leu Pro Tyr Gly Leu
            900                 905                 910

Tyr Ser Thr Leu Ala Tyr Asn Lys Val Asp Val Lys Gly Lys Thr Leu
        915                 920                 925

Asn Pro Thr Leu Ala Gly Thr Asn Ile Leu Phe Asp Ala Ile Gln Pro
    930                 935                 940

Ser Arg Tyr Val Val Gly Leu Gly Tyr Asp Ala Pro Ser Gln Lys Trp
945                 950                 955                 960

Gly Ala Asn Ala Ile Phe Thr His Ser Asp Ala Lys Asn Pro Ser Glu
                965                 970                 975

Leu Leu Ala Asp Lys Asn Leu Gly Asn Gly Asn Ile Gln Thr Lys Gln
            980                 985                 990

Ala Thr Lys Ala Lys Ser Thr Pro Trp Gln Thr Leu Asp Leu Ser Gly
        995                 1000                1005

Tyr Val Asn Ile Lys Asp Asn Phe Thr Leu Arg Ala Gly Val Tyr Asn
    1010                1015                1020

Val Phe Asn Thr Tyr Tyr Thr Thr Trp Glu Ala Leu Arg Gln Thr Ala
1025                1030                1035                1040

Glu Gly Ala Val Asn Gln His Thr Gly Leu Ser Gln Asp Lys His Tyr
                1045                1050                1055

Gly Arg Tyr Ala Ala Pro Gly Arg Asn Tyr Gln Leu Ala Leu Glu Met
            1060                1065                1070

Lys Phe (2) INFORMATION FOR SEQ ID NO:8:

(i) SEQUENCE CHARACTERISTICS:
        (A) LENGTH: 1053 amino acids
        (B) TYPE: amino acid
        (C) STRANDEDNESS: single
        (D) TOPOLOGY: linear (xi) SEQUENCE DESCRIPTION: SEQ ID NO:8:

Leu Ser Leu Gly Leu Leu Asn Ile Thr Gln Val Ala Leu Ala Asn Thr
1               5                   10                  15

Thr Ala Asp Lys Ala Glu Ala Thr Asp Lys Thr Asn Leu Val Val Val
            20                  25                  30

Leu Asp Glu Thr Val Val Thr Ala Lys Lys Asn Ala Arg Lys Ala Asn
        35                  40                  45

Glu Val Thr Gly Leu Gly Lys Val Lys Thr Ala Glu Thr Ile Asn
    50                  55                  60

Lys Glu Gln Val Leu Asn Ile Arg Asp Leu Thr Arg Tyr Asp Pro Gly
65                  70                  75                  80

Ile Ala Val Val Glu Gln Gly Arg Gly Ala Ser Ser Gly Tyr Ser Ile
                85                  90                  95

Arg Gly Met Asp Lys Asn Arg Val Ala Val Leu Val Asp Gly Ile Asn
            100                 105                 110
```

-continued

```
Gln Ala Gln His Tyr Ala Leu Gln Gly Pro Val Ala Gly Lys Asn Tyr
        115                 120                 125
Ala Ala Gly Gly Ala Ile Asn Glu Ile Glu Tyr Glu Asn Val Arg Ser
    130                 135                 140
Val Glu Ile Ser Lys Gly Ala Asn Ser Ser Glu Tyr Gly Ser Gly Ala
145                 150                 155                 160
Leu Ser Gly Ser Val Ala Phe Val Thr Lys Thr Ala Asp Asp Ile Ile
                165                 170                 175
Lys Asp Gly Lys Asp Trp Gly Val Gln Thr Lys Thr Ala Tyr Ala Ser
            180                 185                 190
Lys Asn Asn Ala Trp Val Asn Ser Val Ala Ala Gly Lys Ala Gly
        195                 200                 205
Ser Phe Ser Gly Leu Ile Ile Tyr Thr Asp Arg Arg Gly Gln Glu Tyr
    210                 215                 220
Lys Ala His Asp Asp Ala Tyr Gln Gly Ser Gln Ser Phe Asp Arg Ala
225                 230                 235                 240
Val Ala Thr Thr Asp Pro Asn Asn Arg Thr Phe Leu Ile Ala Asn Glu
                245                 250                 255
Cys Ala Asn Gly Asn Tyr Glu Ala Cys Ala Ala Gly Gly Gln Thr Lys
                260                 265                 270
Leu Gln Ala Lys Pro Thr Asn Val Arg Asp Lys Val Asn Val Lys Asp
        275                 280                 285
Tyr Thr Gly Pro Asn Arg Leu Ile Pro Asn Pro Leu Thr Gln Asp Ser
290                 295                 300
Lys Ser Leu Leu Leu Arg Pro Gly Tyr Gln Leu Asn Asp Lys His Tyr
305                 310                 315                 320
Val Gly Gly Val Tyr Glu Ile Thr Lys Gln Asn Tyr Ala Met Gln Asp
                325                 330                 335
Lys Thr Val Pro Ala Tyr Leu Thr Val His Asp Ile Glu Lys Ser Arg
            340                 345                 350
Leu Ser Asn His Ala Gln Ala Asn Gly Tyr Tyr Gln Gly Asn Asn Leu
        355                 360                 365
Gly Glu Arg Ile Arg Asp Thr Ile Gly Pro Asp Ser Gly Tyr Gly Ile
    370                 375                 380
Asn Tyr Ala His Gly Val Phe Tyr Asp Glu Lys His Gln Lys Asp Arg
385                 390                 395                 400
Leu Gly Leu Glu Tyr Val Tyr Asp Ser Lys Gly Glu Asn Lys Trp Phe
                405                 410                 415
Asp Asp Val Arg Val Ser Tyr Asp Lys Gln Asp Ile Thr Leu Arg Ser
            420                 425                 430
Gln Leu Thr Asn Thr His Cys Ser Thr Tyr Pro His Ile Asp Lys Asn
        435                 440                 445
Cys Thr Pro Asp Val Asn Lys Pro Phe Ser Val Lys Glu Val Asp Asn
450                 455                 460
Asn Ala Tyr Lys Glu Gln His Asn Leu Ile Lys Ala Val Phe Asn Lys
465                 470                 475                 480
Lys Met Ala Leu Gly Ser Thr His His Ile Asn Leu Gln Val Gly
                485                 490                 495
Tyr Asp Lys Phe Asn Ser Ser Leu Ser Arg Glu Asp Tyr Arg Leu Ala
            500                 505                 510
Thr His Gln Ser Tyr Glu Lys Leu Asp Tyr Thr Pro Pro Ser Asn Pro
        515                 520                 525
Leu Pro Asp Lys Phe Lys Pro Ile Leu Gly Ser Asn Asn Lys Pro Ile
```

```
            530               535               540
    Cys Leu Asp Ala Tyr Gly Tyr Gly His Asp His Pro Gln Ala Cys Asn
    545                 550               555               560

Ala Lys Asn Ser Thr Tyr Gln Asn Phe Ala Ile Lys Lys Gly Ile Glu
                    565               570               575

Gln Tyr Asn Gln Lys Thr Asn Thr Asp Lys Ile Asp Tyr Gln Ala Ile
                580               585               590

Ile Asp Gln Tyr Asp Lys Gln Asn Pro Asn Ser Thr Leu Lys Pro Phe
                595               600               605

Glu Lys Ile Lys Gln Ser Leu Gly Gln Glu Lys Tyr Asn Lys Ile Asp
            610              615               620

Glu Leu Gly Phe Lys Ala Tyr Lys Asp Leu Arg Asn Glu Trp Ala Gly
    625                 630               635               640

Trp Thr Asn Asp Asn Ser Gln Gln Asn Ala Asn Lys Gly Thr Asp Asn
                    645               650               655

Ile Tyr Gln Pro Asn Gln Ala Thr Val Val Lys Asp Asp Lys Cys Lys
                660               665               670

Tyr Ser Glu Thr Asn Ser Tyr Ala Asp Cys Ser Thr Thr Ala His Ile
                675               680               685

Ser Gly Asp Asn Tyr Phe Ile Ala Leu Lys Asp Asn Met Thr Ile Asn
            690               695               700

Lys Tyr Val Asp Leu Gly Leu Gly Ala Arg Tyr Asp Arg Ile Lys His
    705                 710               715               720

Lys Ser Asp Val Pro Leu Val Asp Asn Ser Ala Ser Asn Gln Leu Ser
                    725               730               735

Trp Asn Phe Gly Val Val Lys Pro Thr Asn Trp Leu Asp Ile Ala
                740               745               750

Tyr Arg Ser Ser Gln Gly Phe Arg Met Pro Ser Phe Ser Glu Met Tyr
                755               760               765

Gly Glu Arg Phe Gly Val Thr Ile Gly Lys Gly Thr Gln His Gly Cys
    770                 775               780

Lys Gly Leu Tyr Tyr Ile Cys Gln Gln Thr Val His Gln Thr Lys Leu
    785                 790               795               800

Lys Pro Glu Lys Ser Phe Asn Gln Glu Ile Gly Ala Thr Leu His Asn
                    805               810               815

His Leu Gly Ser Leu Glu Val Ser Tyr Phe Lys Asn Arg Tyr Thr Asp
                820               825               830

Leu Ile Val Gly Lys Ser Glu Glu Ile Arg Thr Leu Thr Gln Gly Asp
                835               840               845

Asn Ala Gly Lys Gln Arg Gly Lys Gly Asp Leu Gly Phe His Asn Gly
    850                 855               860

Gln Asp Ala Asp Leu Thr Gly Ile Asn Ile Leu Gly Arg Leu Asp Leu
    865                 870               875               880

Asn Ala Val Asn Ser Arg Leu Pro Tyr Gly Leu Tyr Ser Thr Leu Ala
                    885               890               895

Tyr Asn Lys Val Asp Val Lys Gly Lys Thr Leu Asn Pro Thr Leu Ala
                900               905               910

Gly Thr Asn Ile Leu Phe Asp Ala Ile Gln Pro Ser Arg Tyr Val Val
                915               920               925

Gly Leu Gly Tyr Asp Ala Pro Ser Gln Lys Trp Gly Ala Asn Ala Ile
                930               935               940

Phe Thr His Ser Asp Ala Lys Asn Pro Ser Glu Leu Leu Ala Asp Lys
    945                 950               955               960
```

```
Asn Leu Gly Asn Gly Asn Ile Gln Thr Lys Gln Ala Thr Lys Ala Lys
                965                 970                 975

Ser Thr Pro Trp Gln Thr Leu Asp Leu Ser Gly Tyr Val Asn Ile Lys
            980                 985                 990

Asp Asn Phe Thr Leu Arg Ala Gly Val Tyr Asn Val Phe Asn Thr Tyr
        995                1000                1005

Tyr Thr Thr Trp Glu Ala Leu Arg Gln Thr Ala Glu Gly Ala Val Asn
    1010                1015                1020

Gln His Thr Gly Leu Ser Gln Asp Lys His Tyr Gly Arg Tyr Ala Ala
1025                1030                1035                1040

Pro Gly Arg Asn Tyr Gln Leu Ala Leu Glu Met Lys Phe
                1045                1050
```

(2) INFORMATION FOR SEQ ID NO:9:

(i) SEQUENCE CHARACTERISTICS:
        (A) LENGTH: 702 amino acids
        (B) TYPE: amino acid
        (C) STRANDEDNESS: single
        (D) TOPOLOGY: linear (xi) SEQUENCE DESCRIPTION: SEQ ID NO:9:

```
Met Lys His Ile Pro Leu Thr Thr Leu Cys Val Ala Ile Ser Ala Val
1               5                  10                  15

Leu Leu Thr Ala Cys Gly Gly Ser Gly Gly Ser Asn Pro Pro Ala Pro
            20                  25                  30

Thr Pro Ile Pro Asn Ala Ser Gly Ser Gly Asn Thr Gly Asn Thr Gly
        35                  40                  45

Asn Ala Gly Gly Thr Asp Asn Thr Ala Asn Ala Gly Asn Thr Gly Gly
    50                  55                  60

Thr Asn Ser Gly Thr Gly Ser Ala Asn Thr Pro Glu Pro Lys Tyr Gln
65                  70                  75                  80

Asp Val Pro Thr Glu Lys Asn Glu Lys Asp Lys Val Ser Ser Ile Gln
                85                  90                  95

Glu Pro Ala Met Gly Tyr Gly Met Ala Leu Ser Lys Ile Asn Leu His
            100                 105                 110

Asn Arg Gln Asp Thr Pro Leu Asp Glu Lys Asn Ile Ile Thr Leu Asp
        115                 120                 125

Gly Lys Lys Gln Val Ala Glu Gly Lys Lys Ser Pro Leu Pro Phe Ser
    130                 135                 140

Leu Asp Val Glu Asn Lys Leu Leu Asp Gly Tyr Ile Ala Lys Met Asn
145                 150                 155                 160

Val Ala Asp Lys Asn Ala Ile Gly Asp Arg Ile Lys Lys Gly Asn Lys
                165                 170                 175

Glu Ile Ser Asp Glu Glu Leu Ala Lys Gln Ile Lys Glu Ala Val Arg
            180                 185                 190

Lys Ser His Glu Phe Gln Gln Val Leu Ser Ser Leu Glu Asn Lys Ile
        195                 200                 205

Phe His Ser Asn Asp Gly Thr Thr Lys Ala Thr Thr Arg Asp Leu Lys
    210                 215                 220

Tyr Val Asp Tyr Gly Tyr Tyr Leu Ala Asn Asp Gly Asn Tyr Leu Thr
225                 230                 235                 240

Val Lys Thr Asp Lys Leu Trp Asn Leu Gly Pro Val Gly Gly Val Phe
                245                 250                 255

Tyr Asn Gly Thr Thr Thr Ala Lys Glu Leu Pro Thr Gln Asp Ala Val
```

-continued

```
                260                 265                 270
Lys Tyr Lys Gly His Trp Asp Phe Met Thr Asp Val Ala Asn Arg Arg
            275                 280                 285
Asn Arg Phe Ser Glu Val Lys Glu Asn Ser Gln Ala Gly Trp Tyr Tyr
            290                 295                 300
Gly Ala Ser Ser Lys Asp Glu Tyr Asn Arg Leu Leu Thr Lys Glu Asp
305                 310                 315                 320
Ser Ala Pro Asp Gly His Ser Gly Tyr Gly His Ser Ser Glu Phe
                325                 330                 335
Thr Val Asn Phe Lys Glu Lys Lys Leu Thr Gly Lys Leu Phe Ser Asn
                340                 345                 350
Leu Gln Asp Arg His Lys Gly Asn Val Thr Lys Thr Glu Arg Tyr Asp
            355                 360                 365
Ile Asp Ala Asn Ile His Gly Asn Arg Phe Arg Gly Ser Ala Thr Ala
            370                 375                 380
Ser Asn Lys Asn Asp Thr Ser Lys His Pro Phe Thr Ser Asp Ala Asn
385                 390                 395                 400
Asn Arg Leu Glu Gly Gly Phe Tyr Gly Pro Lys Gly Glu Glu Leu Ala
                405                 410                 415
Gly Lys Phe Leu Thr Asn Asp Asn Lys Leu Phe Gly Val Phe Gly Ala
                420                 425                 430
Lys Arg Glu Ser Lys Ala Glu Lys Thr Glu Ala Ile Leu Asp Ala
            435                 440                 445
Tyr Ala Leu Gly Thr Phe Asn Thr Ser Asn Ala Thr Thr Phe Thr Pro
            450                 455                 460
Phe Thr Glu Lys Gln Leu Asp Asn Phe Gly Asn Ala Lys Lys Leu Val
465                 470                 475                 480
Leu Gly Ser Thr Val Ile Asp Leu Val Pro Thr Asp Ala Thr Lys Asn
                485                 490                 495
Glu Phe Thr Lys Asp Lys Pro Glu Ser Ala Thr Asn Glu Ala Gly Glu
                500                 505                 510
Thr Leu Met Val Asn Asp Glu Val Ser Val Lys Thr Tyr Gly Lys Asn
            515                 520                 525
Phe Glu Tyr Leu Lys Phe Gly Glu Leu Ser Ile Gly Gly Ser His Ser
            530                 535                 540
Val Phe Leu Gln Gly Glu Arg Thr Ala Thr Gly Glu Lys Ala Val
545                 550                 555                 560
Pro Thr Thr Gly Thr Ala Lys Tyr Leu Gly Asn Trp Val Gly Tyr Ile
                565                 570                 575
Thr Gly Lys Asp Thr Gly Thr Gly Lys Ser Phe Thr Asp Ala
                580                 585                 590
Gln Asp Val Ala Asp Phe Asp Ile Asp Phe Gly Asn Lys Ser Val Ser
            595                 600                 605
Gly Lys Leu Ile Thr Lys Gly Arg Gln Asp Pro Val Phe Ser Ile Thr
            610                 615                 620
Gly Gln Ile Ala Gly Asn Gly Trp Thr Gly Thr Ala Ser Thr Thr Lys
625                 630                 635                 640
Ala Asp Ala Gly Gly Tyr Lys Ile Asp Ser Ser Thr Gly Lys Ser
                645                 650                 655
Ile Val Ile Lys Asp Ala Asn Val Thr Gly Gly Phe Tyr Gly Pro Asn
                660                 665                 670
Ala Asn Glu Met Gly Gly Ser Phe Thr His Asn Ala Asp Asp Ser Lys
            675                 680                 685
```

```
Ala Ser Val Val Phe Gly Thr Lys Arg Gln Gln Glu Val Lys
    690                 695                 700
```

(2) INFORMATION FOR SEQ ID NO:10:

(i) SEQUENCE CHARACTERISTICS:
        (A) LENGTH: 682 amino acids
        (B) TYPE: amino acid
        (C) STRANDEDNESS: single
        (D) TOPOLOGY: linear (xi) SEQUENCE DESCRIPTION: SEQ ID NO:10:

```
Cys Gly Gly Ser Gly Gly Ser Asn Pro Pro Ala Pro Thr Pro Ile Pro
1               5                   10                  15

Asn Ala Ser Gly Ser Gly Asn Thr Gly Asn Thr Gly Asn Ala Gly Gly
                20                  25                  30

Thr Asp Asn Thr Ala Asn Ala Gly Asn Thr Gly Gly Thr Asn Ser Gly
            35                  40                  45

Thr Gly Ser Ala Asn Thr Pro Glu Pro Lys Tyr Gln Asp Val Pro Thr
    50                  55                  60

Glu Lys Asn Glu Lys Asp Lys Val Ser Ser Ile Gln Glu Pro Ala Met
65                  70                  75                  80

Gly Tyr Gly Met Ala Leu Ser Lys Ile Asn Leu His Asn Arg Gln Asp
                85                  90                  95

Thr Pro Leu Asp Glu Lys Asn Ile Ile Thr Leu Asp Gly Lys Lys Gln
            100                 105                 110

Val Ala Glu Gly Lys Lys Ser Pro Leu Pro Phe Ser Leu Asp Val Glu
        115                 120                 125

Asn Lys Leu Leu Asp Gly Tyr Ile Ala Lys Met Asn Val Ala Asp Lys
    130                 135                 140

Asn Ala Ile Gly Asp Arg Ile Lys Lys Gly Asn Lys Glu Ile Ser Asp
145                 150                 155                 160

Glu Glu Leu Ala Lys Gln Ile Lys Glu Ala Val Arg Lys Ser His Glu
                165                 170                 175

Phe Gln Gln Val Leu Ser Ser Leu Glu Asn Lys Ile Phe His Ser Asn
            180                 185                 190

Asp Gly Thr Thr Lys Ala Thr Thr Arg Asp Leu Lys Tyr Val Asp Tyr
        195                 200                 205

Gly Tyr Tyr Leu Ala Asn Asp Gly Asn Tyr Leu Thr Val Lys Thr Asp
    210                 215                 220

Lys Leu Trp Asn Leu Gly Pro Val Gly Gly Val Phe Tyr Asn Gly Thr
225                 230                 235                 240

Thr Thr Ala Lys Glu Leu Pro Thr Gln Asp Ala Val Lys Tyr Lys Gly
                245                 250                 255

His Trp Asp Phe Met Thr Asp Val Ala Asn Arg Arg Asn Arg Phe Ser
            260                 265                 270

Glu Val Lys Glu Asn Ser Gln Ala Gly Trp Tyr Tyr Gly Ala Ser Ser
        275                 280                 285

Lys Asp Glu Tyr Asn Arg Leu Leu Thr Lys Glu Asp Ser Ala Pro Asp
    290                 295                 300

Gly His Ser Gly Glu Tyr Gly His Ser Ser Glu Phe Thr Val Asn Phe
305                 310                 315                 320

Lys Glu Lys Lys Leu Thr Gly Lys Leu Phe Ser Asn Leu Gln Asp Arg
                325                 330                 335

His Lys Gly Asn Val Thr Lys Thr Glu Arg Tyr Asp Ile Asp Ala Asn
```

```
            340                 345                 350
Ile His Gly Asn Arg Phe Arg Gly Ser Ala Thr Ala Ser Asn Lys Asn
            355                 360                 365
Asp Thr Ser Lys His Pro Phe Thr Ser Asp Ala Asn Asn Arg Leu Glu
    370                 375                 380
Gly Gly Phe Tyr Gly Pro Lys Gly Glu Glu Leu Ala Gly Lys Phe Leu
385                 390                 395                 400
Thr Asn Asp Asn Lys Leu Phe Gly Val Phe Gly Ala Lys Arg Glu Ser
                405                 410                 415
Lys Ala Glu Glu Lys Thr Glu Ala Ile Leu Asp Ala Tyr Ala Leu Gly
                420                 425                 430
Thr Phe Asn Thr Ser Asn Ala Thr Thr Phe Thr Pro Phe Thr Glu Lys
            435                 440                 445
Gln Leu Asp Asn Phe Gly Asn Ala Lys Lys Leu Val Leu Gly Ser Thr
    450                 455                 460
Val Ile Asp Leu Val Pro Thr Asp Ala Thr Lys Asn Glu Phe Thr Lys
465                 470                 475                 480
Asp Lys Pro Glu Ser Ala Thr Asn Glu Ala Gly Glu Thr Leu Met Val
                485                 490                 495
Asn Asp Glu Val Ser Val Lys Thr Tyr Gly Lys Asn Phe Glu Tyr Leu
                500                 505                 510
Lys Phe Gly Glu Leu Ser Ile Gly Gly Ser His Ser Val Phe Leu Gln
            515                 520                 525
Gly Glu Arg Thr Ala Thr Thr Gly Glu Lys Ala Val Pro Thr Thr Gly
    530                 535                 540
Thr Ala Lys Tyr Leu Gly Asn Trp Val Gly Tyr Ile Thr Gly Lys Asp
545                 550                 555                 560
Thr Gly Thr Gly Thr Gly Lys Ser Phe Thr Asp Ala Gln Asp Val Ala
                565                 570                 575
Asp Phe Asp Ile Asp Phe Gly Asn Lys Ser Val Ser Gly Lys Leu Ile
                580                 585                 590
Thr Lys Gly Arg Gln Asp Pro Val Phe Ser Ile Thr Gly Gln Ile Ala
            595                 600                 605
Gly Asn Gly Trp Thr Gly Thr Ala Ser Thr Thr Lys Ala Asp Ala Gly
    610                 615                 620
Gly Tyr Lys Ile Asp Ser Ser Thr Gly Lys Ser Ile Val Ile Lys
625                 630                 635                 640
Asp Ala Asn Val Thr Gly Gly Phe Tyr Gly Pro Asn Ala Asn Glu Met
                645                 650                 655
Gly Gly Ser Phe Thr His Asn Ala Asp Asp Ser Lys Ala Ser Val Val
                660                 665                 670
Phe Gly Thr Lys Arg Gln Gln Glu Val Lys
            675                 680

(2) INFORMATION FOR SEQ ID NO:11:

(i) SEQUENCE CHARACTERISTICS:
        (A) LENGTH: 1070 amino acids
        (B) TYPE: amino acid
        (C) STRANDEDNESS: single
        (D) TOPOLOGY: linear (xi) SEQUENCE DESCRIPTION: SEQ ID NO:11:

Met Asn Gln Ser Lys Lys Ser Lys Lys Ser Lys Gln Val Leu Lys Leu
1               5                   10                  15
```

-continued

```
Ser Ala Leu Ser Leu Gly Leu Leu Asn Ile Thr Gln Val Ala Leu Ala
             20                  25                  30

Asn Thr Thr Ala Asp Lys Ala Glu Ala Thr Asp Lys Thr Asn Leu Val
         35                  40                  45

Val Val Leu Asp Glu Thr Val Thr Ala Lys Lys Asn Ala Arg Lys
 50                  55                  60

Ala Asn Glu Val Thr Gly Leu Gly Lys Val Lys Thr Ala Glu Thr
 65                  70                  75                  80

Ile Asn Lys Glu Gln Val Leu Asn Ile Arg Asp Leu Thr Arg Tyr Asp
                 85                  90                  95

Pro Gly Ile Ala Val Val Glu Gln Gly Arg Gly Ala Ser Ser Gly Tyr
                100                 105                 110

Ser Ile Arg Gly Met Asp Lys Asn Arg Val Ala Val Leu Val Asp Gly
             115                 120                 125

Ile Asn Gln Ala Gln His Tyr Ala Leu Gln Gly Pro Val Ala Gly Lys
 130                 135                 140

Asn Tyr Ala Ala Gly Gly Ala Ile Asn Glu Ile Glu Tyr Glu Asn Val
145                 150                 155                 160

Arg Ser Val Glu Ile Ser Lys Gly Ala Asn Ser Ser Glu Tyr Gly Ser
             165                 170                 175

Gly Ala Leu Ser Gly Ser Val Ala Phe Val Thr Lys Thr Ala Asp Asp
             180                 185                 190

Ile Ile Lys Asp Gly Lys Asp Trp Gly Val Gln Thr Lys Thr Ala Tyr
     195                 200                 205

Ala Ser Lys Asn Asn Ala Trp Val Asn Ser Val Ala Ala Gly Lys
 210                 215                 220

Ala Gly Ser Phe Ser Gly Leu Ile Ile Tyr Thr Asp Arg Arg Gly Gln
225                 230                 235                 240

Glu Tyr Lys Ala His Asp Asp Ala Tyr Gln Gly Ser Gln Ser Phe Asp
             245                 250                 255

Arg Ala Val Ala Thr Thr Asp Pro Asn Asn Pro Lys Phe Leu Ile Ala
             260                 265                 270

Asn Glu Cys Ala Asn Gly Asn Tyr Glu Ala Cys Ala Ala Gly Gly Gln
             275                 280                 285

Thr Lys Leu Gln Ala Lys Pro Thr Asn Val Arg Asp Lys Val Asn Val
 290                 295                 300

Lys Asp Tyr Thr Gly Pro Asn Arg Leu Ile Pro Asn Pro Leu Thr Gln
305                 310                 315                 320

Asp Ser Lys Ser Leu Leu Arg Pro Gly Tyr Gln Leu Asn Asp Lys
             325                 330                 335

His Tyr Val Gly Gly Val Tyr Glu Ile Thr Lys Gln Asn Tyr Ala Met
             340                 345                 350

Gln Asp Lys Thr Val Pro Ala Tyr Leu Thr Val His Asp Ile Glu Lys
             355                 360                 365

Ser Arg Leu Ser Asn His Gly Gln Ala Asn Gly Tyr Tyr Gln Gly Asn
 370                 375                 380

Asn Leu Gly Glu Arg Ile Arg Asp Ala Ile Gly Ala Asn Ser Gly Tyr
385                 390                 395                 400

Gly Ile Asn Tyr Ala His Gly Val Phe Tyr Asp Glu Lys His Gln Lys
             405                 410                 415

Asp Arg Leu Gly Leu Glu Tyr Tyr Asp Ser Lys Gly Glu Asn Lys
             420                 425                 430

Trp Phe Asp Asp Val Arg Val Ser Tyr Asp Lys Gln Asp Ile Thr Leu
```

-continued

```
              435                 440                 445
    Arg Ser Gln Leu Thr Asn Thr His Cys Ser Thr Tyr Pro His Ile Asp
        450                 455                 460
    Lys Asn Cys Thr Pro Asp Val Asn Lys Pro Phe Ser Val Lys Glu Val
    465                 470                 475                 480
    Asp Asn Asn Ala Tyr Lys Glu Gln His Asn Leu Ile Lys Ala Val Phe
                    485                 490                 495
    Asn Lys Lys Met Ala Leu Gly Asn Thr His His Ile Asn Leu Gln
                500                 505                 510
    Val Gly Tyr Asp Lys Phe Asn Ser Ser Leu Ser Arg Glu Asp Tyr Arg
                515                 520                 525
    Leu Ala Thr His Gln Ser Tyr Gln Lys Leu Asp Tyr Thr Pro Pro Ser
            530                 535                 540
    Asn Pro Leu Pro Asp Lys Phe Lys Pro Ile Leu Gly Ser Asn Asn Arg
    545                 550                 555                 560
    Pro Ile Cys Leu Asp Ala Tyr Gly Tyr Gly His Asp His Pro Gln Ala
                    565                 570                 575
    Cys Asn Ala Lys Asn Ser Thr Tyr Gln Asn Phe Ala Ile Lys Lys Gly
                580                 585                 590
    Ile Glu Gln Tyr Asn Gln Thr Asn Thr Asp Lys Ile Asp Tyr Gln Ala
                595                 600                 605
    Val Ile Asp Gln Tyr Asp Lys Gln Asn Pro Asn Ser Thr Leu Lys Pro
        610                 615                 620
    Phe Glu Lys Ile Lys Gln Ser Leu Gly Gln Glu Lys Tyr Asp Glu Ile
    625                 630                 635                 640
    Asp Arg Leu Gly Phe Asn Ala Tyr Lys Asp Leu Arg Asn Glu Trp Ala
                    645                 650                 655
    Gly Trp Thr Asn Asp Asn Ser Gln Gln Asn Ala Asn Lys Gly Thr Asp
                660                 665                 670
    Asn Ile Tyr Gln Pro Asn Gln Ala Thr Val Val Lys Asp Asp Lys Cys
                675                 680                 685
    Lys Tyr Ser Glu Thr Asn Ser Tyr Ala Asp Cys Ser Thr Thr Arg His
        690                 695                 700
    Ile Ser Gly Asp Asn Tyr Phe Ile Ala Leu Lys Asp Asn Met Thr Ile
    705                 710                 715                 720
    Asn Lys Tyr Val Asp Leu Gly Leu Gly Ala Arg Tyr Asp Arg Ile Lys
                    725                 730                 735
    His Lys Ser Asp Val Pro Leu Val Asp Asn Ser Ala Ser Asn Gln Leu
                740                 745                 750
    Ser Trp Asn Phe Gly Val Val Lys Pro Thr Asn Trp Leu Asp Ile
                755                 760                 765
    Ala Tyr Arg Ser Ser Gln Gly Phe Arg Met Pro Ser Phe Ser Glu Met
        770                 775                 780
    Tyr Gly Glu Arg Phe Gly Val Thr Ile Gly Lys Gly Thr Gln His Gly
    785                 790                 795                 800
    Cys Lys Gly Leu Tyr Tyr Ile Cys Gln Gln Thr Val His Gln Thr Lys
                    805                 810                 815
    Leu Lys Pro Glu Lys Ser Phe Asn Gln Glu Ile Gly Ala Thr Leu His
                820                 825                 830
    Asn His Leu Gly Ser Leu Glu Val Ser Tyr Phe Lys Asn Arg Tyr Thr
                835                 840                 845
    Asp Leu Ile Val Gly Lys Ser Glu Ile Arg Thr Leu Thr Gln Gly
        850                 855                 860
```

```
Asp Asn Ala Gly Lys Gln Arg Gly Lys Gly Asp Leu Gly Phe His Asn
865                 870                 875                 880

Gly Gln Asp Ala Asp Leu Thr Gly Ile Asn Ile Leu Gly Arg Leu Asp
                885                 890                 895

Leu Asn Ala Val Asn Ser Arg Leu Pro Tyr Gly Leu Tyr Ser Thr Leu
                900                 905                 910

Ala Tyr Asn Lys Val Asp Val Lys Gly Lys Thr Leu Asn Pro Thr Leu
                915                 920                 925

Ala Gly Thr Asn Ile Leu Phe Asp Ala Ile Gln Pro Ser Arg Tyr Val
        930                 935                 940

Val Gly Leu Gly Tyr Asp Ala Pro Ser Gln Lys Trp Gly Ala Asn Ala
945                 950                 955                 960

Ile Phe Thr His Ser Asp Ala Lys Asn Pro Ser Glu Leu Leu Ala Asp
                965                 970                 975

Lys Asn Leu Gly Asn Gly Asn Asn Gln Thr Lys Gln Ala Thr Lys Ala
                980                 985                 990

Lys Ser Thr Pro Trp Gln Thr Leu Asp Leu Ser Gly Tyr Val Asn Ile
                995                 1000                1005

Lys Asp Asn Phe Thr Leu Arg Ala Gly Val Tyr Asn Val Phe Asn Thr
        1010                1015                1020

Tyr Tyr Thr Thr Trp Glu Ala Leu Arg Gln Thr Ala Glu Gly Ala Val
1025                1030                1035                1040

Asn Gln His Thr Gly Leu Ser Gln Asp Lys His Tyr Gly Arg Tyr Ala
                1045                1050                1055

Ala Pro Gly Arg Asn Tyr Gln Leu Ala Leu Glu Met Lys Phe
                1060                1065                1070

(2) INFORMATION FOR SEQ ID NO:12:

(i) SEQUENCE CHARACTERISTICS:
        (A) LENGTH: 17 amino acids
        (B) TYPE: amino acid
        (C) STRANDEDNESS: single
        (D) TOPOLOGY: linear (xi) SEQUENCE DESCRIPTION: SEQ ID NO:12:

Asn Gln Ser Lys Lys Ser Lys Lys Ser Lys Gln Val Leu Lys Leu Ser
1               5                   10                  15

Ala (2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:13:

Asn Glu Val Thr Gly Leu Gly
1               5

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: single
        (D) TOPOLOGY: linear
```

(xi) SEQUENCE DESCRIPTION: SEQ ID NO:14:

Gly Ala Ile Asn Glu Ile Glu
1               5

(2) INFORMATION FOR SEQ ID NO:15:

(i) SEQUENCE CHARACTERISTICS:
            (A) LENGTH: 912 amino acids
            (B) TYPE: amino acid
            (C) STRANDEDNESS: single
            (D) TOPOLOGY: linear (xi) SEQUENCE DESCRIPTION: SEQ ID NO:15:

Met Thr Lys Lys Pro Tyr Phe Arg Leu Ser Ile Ile Ser Cys Leu Leu
1               5                   10                  15

Ile Gly Cys Tyr Val Lys Ala Glu Thr Gln Ser Ile Lys Asp Thr Lys
                20                  25                  30

Glu Ala Ile Ser Ser Glu Val Asp Thr Gln Ser Thr Glu Asp Ser Glu
            35                  40                  45

Leu Glu Thr Ile Ser Val Thr Ala Glu Lys Ile Arg Asp Arg Lys Asp
        50                  55                  60

Asn Glu Val Thr Gly Leu Gly Lys Ile Ile Lys Thr Ser Glu Ser Ile
65                  70                  75                  80

Ser Arg Glu Gln Val Leu Asn Ile Arg Asp Leu Thr Arg Tyr Asp Pro
                85                  90                  95

Gly Ile Ser Val Val Glu Gln Gly Arg Gly Ala Ser Ser Gly Tyr Ser
            100                 105                 110

Ile Arg Gly Met Asp Arg Asn Arg Val Ala Leu Leu Val Asp Gly Leu
        115                 120                 125

Pro Gln Thr Gln Ser Tyr Val Val Gln Ser Pro Leu Val Ala Arg Ser
    130                 135                 140

Gly Tyr Ser Gly Thr Gly Ala Ile Asn Glu Ile Glu Tyr Glu Asn Val
145                 150                 155                 160

Lys Ala Val Glu Ile Ser Lys Gly Gly Ser Ser Glu Tyr Gly Asn
                165                 170                 175

Gly Ala Leu Ala Gly Ser Val Thr Phe Gln Ser Lys Ser Ala Ala Asp
            180                 185                 190

Ile Leu Glu Gly Asp Lys Ser Trp Gly Ile Gln Thr Lys Asn Ala Tyr
        195                 200                 205

Ser Ser Lys Asn Lys Gly Phe Thr His Ser Leu Ala Val Ala Gly Lys
    210                 215                 220

Gln Gly Gly Phe Glu Gly Leu Ala Ile Tyr Thr Gln Arg Asn Ser Ile
225                 230                 235                 240

Glu Thr Gln Val His Lys Asp Ala Leu Lys Gly Val Gln Ser Tyr Asp
                245                 250                 255

Arg Leu Ile Ala Thr Thr Asp Lys Ser Ser Gly Tyr Phe Val Ile Gln
            260                 265                 270

Gly Glu Cys Pro Asn Gly Asp Asp Lys Cys Ala Ala Lys Pro Pro Ala
        275                 280                 285

Thr Leu Ser Thr Gln Ser Glu Thr Val Ser Val Ser Asp Tyr Thr Gly
    290                 295                 300

Ala Asn Arg Ile Lys Pro Asn Pro Met Lys Tyr Glu Ser Gln Ser Trp
305                 310                 315                 320

Phe Leu Arg Gly Gly Tyr His Phe Ser Glu Gln His Tyr Ile Gly Gly
                325                 330                 335

```
Ile Phe Glu Phe Thr Gln Gln Lys Phe Asp Ile Arg Asp Met Thr Phe
            340                 345                 350

Pro Ala Tyr Leu Ser Pro Thr Glu Arg Arg Asp Asp Ser Ser Arg Ser
            355                 360                 365

Phe Tyr Pro Met Gln Asp His Gly Ala Tyr Gln His Ile Glu Asp Gly
            370                 375                 380

Arg Gly Val Lys Tyr Ala Ser Gly Leu Tyr Phe Asp Glu His His Arg
385                 390                 395                 400

Lys Gln Arg Val Gly Ile Glu Tyr Ile Tyr Glu Asn Lys Asn Lys Ala
                    405                 410                 415

Gly Ile Ile Asp Lys Ala Val Leu Ser Ala Asn Gln Gln Asn Ile Ile
                420                 425                 430

Leu Asp Ser Tyr Met Arg His Thr His Cys Ser Leu Tyr Pro Asn Pro
            435                 440                 445

Ser Lys Asn Cys Arg Pro Thr Leu Asp Lys Pro Tyr Ser Tyr Tyr Arg
            450                 455                 460

Ser Asp Arg Asn Val Tyr Lys Glu Lys His Asn Met Leu Gln Leu Asn
465                 470                 475                 480

Leu Glu Lys Lys Ile Gln Gln Asn Trp Leu Thr His Gln Ile Val Phe
                    485                 490                 495

Asn Leu Gly Phe Asp Asp Phe Thr Ser Ala Leu Gln His Lys Asp Tyr
                500                 505                 510

Leu Thr Arg Arg Val Ile Ala Thr Ala Asp Ser Ile Pro Arg Lys Pro
            515                 520                 525

Gly Glu Thr Gly Lys Pro Arg Asn Gly Leu Gln Ser Gln Pro Tyr Leu
            530                 535                 540

Tyr Pro Lys Pro Glu Pro Tyr Phe Ala Gly Gln Asp His Cys Asn Tyr
545                 550                 555                 560

Gln Gly Ser Ser Ser Asn Tyr Arg Asp Cys Lys Val Arg Leu Ile Lys
                    565                 570                 575

Gly Lys Asn Tyr Tyr Phe Ala Ala Arg Asn Asn Met Ala Leu Gly Lys
                580                 585                 590

Tyr Val Asp Leu Gly Leu Gly Ile Arg Tyr Asp Val Ser Arg Thr Lys
            595                 600                 605

Ala Asn Glu Ser Thr Ile Ser Val Gly Lys Phe Lys Asn Phe Ser Trp
            610                 615                 620

Asn Thr Gly Ile Val Ile Lys Pro Thr Glu Trp Leu Asp Leu Ser Tyr
625                 630                 635                 640

Arg Leu Ser Thr Gly Phe Arg Asn Pro Ser Phe Ser Glu Met Tyr Gly
                    645                 650                 655

Trp Arg Tyr Gly Gly Lys Asn Asp Glu Val Tyr Val Gly Lys Phe Lys
                660                 665                 670

Pro Glu Thr Ser Arg Asn Gln Glu Phe Gly Leu Ala Leu Lys Gly Asp
            675                 680                 685

Phe Gly Asn Ile Glu Ile Ser His Phe Ser Asn Ala Tyr Arg Asn Leu
            690                 695                 700

Ile Ala Phe Ala Glu Glu Leu Ser Lys Asn Gly Thr Gly Lys Gly Asn
705                 710                 715                 720

Tyr Gly Tyr His Asn Ala Gln Asn Ala Lys Leu Val Gly Val Asn Ile
                    725                 730                 735

Thr Ala Gln Leu Asp Phe Asn Gly Leu Trp Lys Arg Ile Pro Tyr Gly
                740                 745                 750

Trp Tyr Ala Thr Phe Ala Tyr Asn Gln Val Lys Val Lys Asp Gln Lys
```

-continued

```
                755                 760                 765
Ile Asn Ala Gly Leu Ala Ser Val Ser Ser Tyr Leu Phe Asp Ala Ile
    770                 775                 780
Gln Pro Ser Arg Tyr Ile Ile Gly Leu Gly Tyr Asp His Pro Ser Asn
785                 790                 795                 800
Thr Trp Gly Ile Asn Thr Met Phe Thr Gln Ser Lys Ala Lys Ser Gln
                805                 810                 815
Asn Glu Leu Leu Gly Lys Arg Ala Leu Gly Asn Asn Ser Arg Asp Val
            820                 825                 830
Lys Ser Thr Arg Lys Leu Thr Arg Ala Trp His Ile Leu Asp Val Ser
            835                 840                 845
Gly Tyr Tyr Met Ala Asn Lys Asn Ile Met Leu Arg Leu Gly Ile Tyr
850                 855                 860
Asn Leu Phe Asn Tyr Arg Tyr Val Thr Trp Glu Ala Val Arg Gln Thr
865                 870                 875                 880
Ala Gln Gly Ala Val Asn Gln His Gln Asn Val Gly Ser Tyr Thr Arg
                885                 890                 895
Tyr Ala Ala Ser Gly Arg Asn Tyr Thr Leu Thr Leu Glu Met Lys Phe
            900                 905                 910
```

(2) INFORMATION FOR SEQ ID NO:16:

(i) SEQUENCE CHARACTERISTICS:
        (A) LENGTH: 908 amino acids
        (B) TYPE: amino acid
        (C) STRANDEDNESS: single
        (D) TOPOLOGY: linear (xi) SEQUENCE DESCRIPTION: SEQ ID NO:16:

```
Met Gln Gln Gln His Leu Phe Arg Leu Asn Ile Leu Cys Leu Ser Leu
1               5                   10                  15
Met Thr Ala Leu Pro Val Tyr Ala Glu Asn Val Gln Ala Glu Gln Ala
            20                  25                  30
Gln Glu Lys Gln Leu Asp Thr Ile Gln Val Lys Ala Lys Lys Gln Lys
        35                  40                  45
Thr Arg Arg Asp Asn Glu Val Thr Gly Leu Gly Lys Leu Val Lys Ser
50                  55                  60
Ser Asp Thr Leu Ser Lys Glu Gln Val Leu Asn Ile Arg Asp Leu Thr
65                  70                  75                  80
Arg Tyr Asp Pro Gly Ile Ala Val Val Glu Gln Gly Arg Gly Ala Ser
                85                  90                  95
Ser Gly Tyr Ser Ile Arg Gly Met Asp Lys Asn Arg Val Ser Leu Thr
            100                 105                 110
Val Asp Gly Val Ser Gln Ile Gln Ser Tyr Thr Ala Gln Ala Ala Leu
        115                 120                 125
Gly Gly Thr Arg Thr Ala Gly Ser Ser Gly Ala Ile Asn Glu Ile Glu
    130                 135                 140
Tyr Glu Asn Val Lys Ala Val Glu Ile Ser Lys Gly Ser Asn Ser Ser
145                 150                 155                 160
Glu Tyr Gly Asn Gly Ala Leu Ala Gly Ser Val Ala Phe Gln Thr Lys
                165                 170                 175
Thr Ala Ala Asp Ile Ile Gly Glu Gly Lys Gln Trp Gly Ile Gln Ser
            180                 185                 190
Lys Thr Ala Tyr Ser Gly Lys Asp His Ala Leu Thr Gln Ser Leu Ala
        195                 200                 205
```

-continued

```
Leu Ala Gly Arg Ser Gly Gly Ala Glu Ala Leu Leu Ile Tyr Thr Lys
    210                 215                 220

Arg Arg Gly Arg Glu Ile His Ala His Lys Asp Ala Gly Lys Gly Val
225                 230                 235                 240

Gln Ser Phe Asn Arg Leu Val Leu Asp Glu Asp Lys Lys Glu Gly Gly
                245                 250                 255

Ser Gln Tyr Arg Tyr Phe Ile Val Glu Glu Cys His Asn Gly Tyr
            260                 265                 270

Ala Ala Cys Lys Asn Lys Leu Lys Glu Asp Ala Ser Val Lys Asp Glu
                275                 280                 285

Arg Lys Thr Val Ser Thr Gln Asp Tyr Thr Gly Ser Asn Arg Leu Leu
290                 295                 300

Ala Asn Pro Leu Glu Tyr Gly Ser Gln Ser Trp Leu Phe Arg Pro Gly
305                 310                 315                 320

Trp His Leu Asp Asn Arg His Tyr Val Gly Ala Val Leu Glu Arg Thr
                325                 330                 335

Gln Gln Thr Phe Asp Thr Arg Asp Met Thr Val Pro Ala Tyr Phe Thr
                340                 345                 350

Ser Glu Asp Tyr Val Pro Gly Ser Leu Lys Gly Leu Gly Lys Tyr Ser
            355                 360                 365

Gly Asp Asn Lys Ala Glu Arg Leu Phe Val Gln Gly Glu Gly Ser Thr
    370                 375                 380

Leu Gln Gly Ile Gly Tyr Gly Thr Gly Val Phe Tyr Asp Glu Arg His
385                 390                 395                 400

Thr Lys Asn Arg Tyr Gly Val Glu Tyr Val Tyr His Asn Ala Asp Lys
                405                 410                 415

Asp Thr Trp Ala Asp Tyr Ala Arg Leu Ser Tyr Asp Arg Gln Gly Ile
                420                 425                 430

Asp Leu Asp Asn Arg Leu Gln Gln Thr His Cys Ser His Asp Gly Ser
            435                 440                 445

Asp Lys Asn Cys Arg Pro Asp Gly Asn Lys Pro Tyr Ser Phe Tyr Lys
    450                 455                 460

Ser Asp Arg Met Ile Tyr Glu Glu Ser Arg Asn Leu Phe Gln Ala Val
465                 470                 475                 480

Phe Lys Lys Ala Phe Asp Thr Ala Lys Ile Arg His Asn Leu Ser Ile
                485                 490                 495

Asn Leu Gly Tyr Asp Arg Phe Lys Ser Gln Leu Ser His Ser Asp Tyr
            500                 505                 510

Tyr Leu Gln Asn Ala Val Gln Ala Tyr Asp Leu Ile Thr Pro Pro Lys
    515                 520                 525

Pro Pro Phe Pro Asn Gly Ser Lys Asp Asn Pro Tyr Arg Val Ser Ile
    530                 535                 540

Gly Lys Thr Thr Val Asn Thr Ser Pro Ile Cys Arg Phe Gly Asn Asn
545                 550                 555                 560

Thr Tyr Thr Asp Cys Thr Pro Arg Asn Ile Gly Gly Asn Gly Tyr Tyr
                565                 570                 575

Ala Ala Val Gln Asp Asn Val Arg Leu Gly Arg Trp Ala Asp Val Gly
            580                 585                 590

Ala Gly Ile Arg Tyr Asp Tyr Arg Ser Thr His Ser Glu Asp Lys Ser
    595                 600                 605

Val Ser Thr Gly Thr His Arg Asn Leu Ser Trp Asn Ala Gly Val Val
    610                 615                 620

Leu Lys Pro Phe Thr Trp Met Asp Leu Thr Tyr Arg Ala Ser Thr Gly
```

-continued

```
                625                 630                 635                 640
Phe Arg Leu Pro Ser Phe Ala Glu Met Tyr Gly Trp Arg Ala Gly Glu
                    645                 650                 655
Ser Leu Lys Thr Leu Asp Leu Lys Pro Glu Lys Ser Phe Asn Arg Glu
                660                 665                 670
Ala Gly Ile Val Phe Lys Gly Asp Phe Gly Asn Leu Glu Ala Ser Tyr
            675                 680                 685
Phe Asn Asn Ala Tyr Arg Asp Leu Ile Ala Phe Gly Tyr Glu Thr Arg
        690                 695                 700
Thr Gln Asn Gly Gln Thr Ser Ala Ser Gly Asp Pro Gly Tyr Arg Asn
705                 710                 715                 720
Ala Gln Asn Ala Arg Ile Ala Gly Ile Asn Ile Leu Gly Lys Ile Asp
                725                 730                 735
Trp His Gly Val Trp Gly Gly Leu Pro Asp Gly Leu Tyr Ser Thr Leu
                    740                 745                 750
Ala Tyr Asn Arg Ile Lys Val Lys Asp Ala Asp Ile Arg Ala Asp Arg
                755                 760                 765
Thr Phe Val Thr Ser Tyr Leu Phe Asp Ala Val Gln Pro Ser Arg Tyr
770                 775                 780
Val Leu Gly Leu Gly Tyr Asp His Pro Asp Gly Ile Trp Gly Ile Asn
785                 790                 795                 800
Thr Met Phe Thr Tyr Ser Lys Ala Lys Ser Val Asp Glu Leu Leu Gly
                805                 810                 815
Ser Gln Ala Leu Leu Asn Gly Asn Ala Asn Ala Lys Lys Ala Ala Ser
                820                 825                 830
Arg Arg Thr Arg Pro Trp Tyr Val Thr Asp Val Ser Gly Tyr Tyr Asn
                835                 840                 845
Ile Lys Lys His Leu Thr Leu Arg Ala Gly Val Tyr Asn Leu Leu Asn
850                 855                 860
Tyr Arg Tyr Val Thr Trp Glu Asn Val Arg Gln Thr Ala Gly Gly Ala
865                 870                 875                 880
Val Asn Gln His Lys Asn Val Gly Val Tyr Asn Arg Tyr Ala Ala Pro
                885                 890                 895
Gly Arg Asn Tyr Thr Phe Ser Leu Glu Met Lys Phe
                900                 905
```

(2) INFORMATION FOR SEQ ID NO:17:

(i) SEQUENCE CHARACTERISTICS:
        (A) LENGTH: 911 amino acids
        (B) TYPE: amino acid
        (C) STRANDEDNESS: single
        (D) TOPOLOGY: linear (xi) SEQUENCE DESCRIPTION: SEQ ID NO:17:

```
Met Gln Gln Gln His Leu Phe Arg Leu Asn Ile Leu Cys Leu Ser Leu
1               5                   10                  15
Met Thr Ala Leu Pro Ala Tyr Ala Glu Asn Val Gln Ala Gly Gln Ala
            20                  25                  30
Gln Glu Lys Gln Leu Asp Thr Ile Gln Val Lys Ala Lys Gln Lys
        35                  40                  45
Thr Arg Arg Asp Asn Glu Val Thr Gly Leu Gly Lys Leu Val Lys Thr
    50                  55                  60
Ala Asp Thr Leu Ser Lys Glu Gln Val Leu Asp Ile Arg Asp Leu Thr
65                  70                  75                  80
```

```
Arg Tyr Asp Pro Gly Ile Ala Val Val Glu Gln Gly Arg Gly Ala Ser
                 85                  90                  95

Ser Gly Tyr Ser Ile Arg Gly Met Asp Lys Asn Arg Val Ser Leu Thr
            100                 105                 110

Val Asp Gly Leu Ala Gln Ile Gln Ser Tyr Thr Ala Gln Ala Ala Leu
        115                 120                 125

Gly Gly Thr Arg Thr Ala Gly Ser Ser Gly Ala Ile Asn Glu Ile Glu
130                 135                 140

Tyr Glu Asn Val Lys Ala Val Glu Ile Ser Lys Gly Ser Asn Ser Val
145                 150                 155                 160

Glu Gln Gly Ser Gly Ala Leu Ala Gly Ser Val Ala Phe Gln Thr Lys
                165                 170                 175

Thr Ala Asp Asp Val Ile Gly Glu Gly Arg Gln Trp Gly Ile Gln Ser
            180                 185                 190

Lys Thr Ala Tyr Ser Gly Lys Asn Arg Gly Leu Thr Gln Ser Ile Ala
        195                 200                 205

Leu Ala Gly Arg Ile Gly Gly Ala Glu Ala Leu Leu Ile His Thr Gly
    210                 215                 220

Arg Arg Ala Gly Glu Ile Arg Ala His Glu Asp Ala Gly Arg Gly Val
225                 230                 235                 240

Gln Ser Phe Asn Arg Leu Val Pro Val Glu Asp Ser Ser Glu Tyr Ala
                245                 250                 255

Tyr Phe Ile Val Glu Asp Glu Cys Glu Gly Lys Asn Tyr Glu Thr Cys
            260                 265                 270

Lys Ser Lys Pro Lys Lys Asp Val Val Gly Lys Asp Glu Arg Gln Thr
        275                 280                 285

Val Ser Thr Arg Asp Tyr Thr Gly Pro Asn Arg Phe Leu Ala Asp Pro
    290                 295                 300

Leu Ser Tyr Glu Ser Arg Ser Trp Leu Phe Arg Pro Gly Phe Arg Phe
305                 310                 315                 320

Glu Asn Lys Arg His Tyr Ile Gly Gly Ile Leu Glu His Thr Gln Gln
                325                 330                 335

Thr Phe Asp Thr Arg Asp Met Thr Val Pro Ala Phe Leu Thr Lys Ala
            340                 345                 350

Val Phe Asp Ala Asn Ser Lys Gln Ala Gly Ser Leu Pro Gly Asn Gly
        355                 360                 365

Lys Tyr Ala Gly Asn His Lys Tyr Gly Gly Leu Phe Thr Asn Gly Glu
    370                 375                 380

Asn Gly Ala Leu Val Gly Ala Glu Tyr Gly Thr Gly Val Phe Tyr Asp
385                 390                 395                 400

Glu Thr His Thr Lys Ser Arg Tyr Gly Leu Glu Tyr Val Tyr Thr Asn
                405                 410                 415

Ala Asp Lys Asp Thr Trp Ala Tyr Ala Arg Leu Ser Tyr Asp Arg
            420                 425                 430

Gln Gly Ile Gly Leu Asp Asn His Phe Gln Gln Thr His Cys Ser Ala
        435                 440                 445

Asp Gly Ser Asp Lys Tyr Cys Arg Pro Ser Ala Asp Lys Pro Phe Ser
    450                 455                 460

Tyr Tyr Lys Ser Asp Arg Val Ile Tyr Gly Glu Ser His Arg Leu Leu
465                 470                 475                 480

Gln Ala Ala Phe Lys Lys Ser Phe Asp Thr Ala Lys Ile Arg His Asn
                485                 490                 495

Leu Ser Val Asn Leu Gly Phe Asp Arg Phe Asp Ser Asn Leu Arg His
```

```
                500                 505                 510
    Gln Asp Tyr Tyr Gln His Ala Asn Arg Ala Tyr Ser Ser Lys Thr
                515                 520                 525

Pro Pro Lys Thr Ala Asn Pro Asn Gly Asp Lys Ser Lys Pro Tyr Trp
                530                 535                 540

Val Ser Ile Gly Gly Gly Asn Val Val Thr Gly Gln Ile Cys Leu Phe
    545                 550                 555                 560

Gly Asn Asn Thr Tyr Thr Asp Cys Thr Pro Arg Ser Ile Asn Gly Lys
                    565                 570                 575

Ser Tyr Tyr Ala Ala Val Arg Asp Asn Val Arg Leu Gly Arg Trp Ala
                    580                 585                 590

Asp Val Gly Ala Gly Leu Arg Tyr Asp Tyr Arg Ser Thr His Ser Asp
                    595                 600                 605

Asp Gly Ser Val Ser Thr Gly Thr His Arg Thr Leu Ser Trp Asn Ala
                610                 615                 620

Gly Ile Val Leu Lys Pro Ala Asp Trp Leu Asp Leu Thr Tyr Arg Thr
    625                 630                 635                 640

Ser Thr Gly Phe Arg Leu Pro Ser Phe Ala Glu Met Tyr Gly Trp Arg
                    645                 650                 655

Ser Gly Val Gln Ser Lys Ala Val Lys Ile Asp Pro Glu Lys Ser Phe
                    660                 665                 670

Asn Lys Glu Ala Gly Ile Val Phe Lys Gly Asp Phe Gly Asn Leu Glu
                    675                 680                 685

Ala Ser Trp Phe Asn Asn Ala Tyr Arg Asp Leu Ile Val Arg Gly Tyr
                690                 695                 700

Glu Ala Gln Ile Lys Asn Gly Lys Glu Glu Ala Lys Gly Asp Pro Ala
    705                 710                 715                 720

Tyr Leu Asn Ala Gln Ser Ala Arg Ile Thr Gly Ile Asn Ile Leu Gly
                    725                 730                 735

Lys Ile Asp Trp Asn Gly Val Trp Asp Lys Leu Pro Glu Gly Trp Tyr
                    740                 745                 750

Ser Thr Phe Ala Tyr Asn Arg Val His Val Arg Asp Ile Lys Lys Arg
                    755                 760                 765

Ala Asp Arg Thr Asp Ile Gln Ser His Leu Phe Asp Ala Ile Gln Pro
    770                 775                 780

Ser Arg Tyr Val Val Gly Leu Gly Tyr Asp Gln Pro Glu Gly Lys Trp
    785                 790                 795                 800

Gly Val Asn Gly Met Leu Thr Tyr Ser Lys Ala Lys Glu Ile Thr Glu
                    805                 810                 815

Leu Leu Gly Ser Arg Ala Leu Leu Asn Gly Asn Ser Arg Asn Thr Lys
                    820                 825                 830

Ala Thr Ala Arg Arg Thr Arg Pro Trp Tyr Ile Val Asp Val Ser Gly
                835                 840                 845

Tyr Tyr Thr Ile Lys Lys His Phe Thr Leu Arg Ala Gly Val Tyr Asn
    850                 855                 860

Leu Leu Asn Tyr Arg Tyr Val Thr Trp Glu Asn Val Arg Gln Thr Ala
    865                 870                 875                 880

Gly Gly Ala Val Asn Gln His Lys Asn Val Gly Val Tyr Asn Arg Tyr
                    885                 890                 895

Ala Ala Pro Gly Arg Asn Tyr Thr Phe Ser Leu Glu Met Lys Phe
                    900                 905                 910

(2) INFORMATION FOR SEQ ID NO:18:
```

(i) SEQUENCE CHARACTERISTICS:
    (A) LENGTH: 915 amino acids
    (B) TYPE: amino acid
    (C) STRANDEDNESS: single
    (D) TOPOLOGY: linear (xi) SEQUENCE DESCRIPTION: SEQ ID NO:18:

Met Gln Gln Gln His Leu Phe Arg Leu Asn Ile Leu Cys Leu Ser Leu
1               5                   10                  15

Met Thr Ala Leu Pro Ala Tyr Ala Glu Asn Val Gln Ala Gly Gln Ala
            20                  25                  30

Gln Glu Lys Gln Leu Asp Thr Ile Gln Val Lys Ala Lys Lys Gln Lys
        35                  40                  45

Thr Arg Arg Asp Asn Glu Val Thr Gly Leu Gly Lys Leu Val Lys Thr
50                  55                  60

Ala Asp Thr Leu Ser Lys Glu Gln Val Leu Asp Ile Arg Asp Leu Thr
65                  70                  75                  80

Arg Tyr Asp Pro Gly Ile Ala Val Val Glu Gln Gly Arg Gly Ala Ser
                85                  90                  95

Ser Gly Tyr Ser Ile Arg Gly Met Asp Lys Asn Arg Val Ser Leu Thr
            100                 105                 110

Val Asp Gly Leu Ala Gln Ile Gln Ser Tyr Thr Ala Gln Ala Ala Leu
        115                 120                 125

Gly Gly Thr Arg Thr Ala Gly Ser Ser Gly Ala Ile Asn Glu Ile Glu
130                 135                 140

Tyr Glu Asn Val Lys Ala Val Glu Ile Ser Lys Gly Ser Asn Ser Val
145                 150                 155                 160

Glu Gln Gly Ser Gly Ala Leu Ala Gly Ser Val Ala Phe Gln Thr Lys
                165                 170                 175

Thr Ala Asp Asp Val Ile Gly Glu Gly Arg Gln Trp Gly Ile Gln Ser
            180                 185                 190

Lys Thr Ala Tyr Ser Gly Lys Asn Arg Gly Leu Thr Gln Ser Leu Ala
        195                 200                 205

Leu Ala Gly Arg Ile Gly Gly Ala Glu Ala Leu Leu Ile Arg Thr Gly
210                 215                 220

Arg His Ala Gly Glu Ile Arg Ala His Glu Ala Ala Gly Arg Gly Val
225                 230                 235                 240

Gln Ser Phe Asn Arg Leu Ala Pro Val Asp Asp Gly Ser Lys Tyr Ala
                245                 250                 255

Tyr Phe Ile Val Glu Glu Glu Cys Lys Asn Gly Gly His Glu Lys Cys
            260                 265                 270

Lys Ala Asn Pro Pro Lys Asp Val Val Gly Glu Asp Lys Arg Gln Thr
        275                 280                 285

Val Ser Thr Arg Asp Tyr Thr Gly Pro Asn Arg Phe Leu Ala Asp Pro
290                 295                 300

Leu Ser Tyr Glu Ser Arg Ser Trp Leu Phe Arg Pro Gly Phe Arg Phe
305                 310                 315                 320

Glu Asn Lys Arg His Tyr Ile Gly Gly Ile Leu Glu Arg Thr Gln Gln
                325                 330                 335

Thr Phe Asp Thr Arg Asp Met Thr Val Pro Ala Phe Leu Thr Lys Ala
            340                 345                 350

Val Phe Asp Ala Asn Gln Lys Gln Ala Gly Ser Leu Arg Gly Asn Gly
        355                 360                 365

Lys Tyr Ala Gly Asn His Lys Tyr Gly Gly Leu Phe Thr Ser Gly Glu

```
              370                 375                 380
Asn Asn Ala Pro Val Gly Ala Glu Tyr Gly Thr Gly Val Phe Tyr Asp
385                 390                 395                 400

Glu Thr His Thr Lys Ser Arg Tyr Gly Leu Glu Tyr Val Tyr Thr Asn
                405                 410                 415

Ala Asp Lys Asp Thr Trp Ala Asp Tyr Ala Arg Leu Ser Tyr Asp Arg
                420                 425                 430

Gln Gly Ile Gly Leu Asp Asn His Phe Gln Gln Thr His Cys Ser Ala
                435                 440                 445

Asp Gly Ser Asp Lys Tyr Cys Arg Pro Ser Ala Asp Lys Pro Phe Ser
                450                 455                 460

Tyr Tyr Lys Ser Asp Arg Val Ile Tyr Gly Glu Ser His Lys Leu Leu
465                 470                 475                 480

Gln Ala Ala Phe Lys Lys Ser Phe Asp Thr Ala Lys Ile Arg His Asn
                485                 490                 495

Leu Ser Val Asn Leu Gly Tyr Asp Arg Phe Gly Ser Asn Leu Arg His
                500                 505                 510

Gln Asp Tyr Tyr Tyr Gln Ser Ala Asn Arg Ala Tyr Ser Ser Lys Thr
                515                 520                 525

Pro Pro Gln Asn Asn Gly Lys Lys Thr Ser Pro Asn Gly Arg Glu Lys
                530                 535                 540

Asn Pro Tyr Trp Val Ser Ile Gly Arg Gly Asn Val Val Thr Arg Gln
545                 550                 555                 560

Ile Cys Leu Phe Gly Asn Asn Thr Tyr Thr Asp Cys Thr Pro Arg Ser
                565                 570                 575

Ile Asn Gly Lys Ser Tyr Tyr Ala Ala Val Arg Asp Asn Val Arg Leu
                580                 585                 590

Gly Arg Trp Ala Asp Val Gly Ala Gly Leu Arg Tyr Asp Tyr Arg Ser
                595                 600                 605

Thr His Ser Asp Asp Gly Ser Val Ser Thr Gly Thr His Arg Thr Leu
                610                 615                 620

Ser Trp Asn Ala Gly Ile Val Leu Lys Pro Ala Asp Trp Leu Asp Leu
625                 630                 635                 640

Thr Tyr Arg Thr Ser Thr Gly Phe Arg Leu Pro Ser Phe Ala Glu Met
                645                 650                 655

Tyr Gly Trp Arg Ser Gly Asp Lys Ile Lys Ala Val Lys Ile Asp Pro
                660                 665                 670

Glu Lys Ser Phe Asn Lys Glu Ala Gly Ile Val Phe Lys Gly Asp Phe
                675                 680                 685

Gly Asn Leu Glu Ala Ser Trp Phe Asn Asn Ala Tyr Arg Asp Leu Ile
                690                 695                 700

Val Arg Gly Tyr Glu Ala Gln Ile Lys Asp Gly Lys Glu Gln Val Lys
705                 710                 715                 720

Gly Asn Pro Ala Tyr Leu Asn Ala Gln Ser Ala Arg Ile Thr Gly Ile
                725                 730                 735

Asn Ile Leu Gly Lys Ile Asp Trp Asn Gly Val Trp Asp Lys Leu Pro
                740                 745                 750

Glu Gly Trp Tyr Ser Thr Phe Ala Tyr Asn Arg Val Arg Val Arg Asp
                755                 760                 765

Ile Lys Lys Arg Ala Asp Arg Thr Asp Ile Gln Ser His Leu Phe Asp
                770                 775                 780

Ala Ile Gln Pro Ser Arg Tyr Val Val Gly Ser Gly Tyr Asp Gln Pro
785                 790                 795                 800
```

-continued

```
Glu Gly Lys Trp Gly Val Asn Gly Met Leu Thr Tyr Ser Lys Ala Lys
                805                 810                 815

Glu Ile Thr Glu Leu Leu Gly Ser Arg Ala Leu Leu Asn Gly Asn Ser
            820                 825                 830

Arg Asn Thr Lys Ala Thr Ser Arg Arg Thr Arg Pro Trp Tyr Ile Val
                835                 840                 845

Asp Val Ser Gly Tyr Tyr Thr Val Lys Lys His Phe Thr Leu Arg Ala
            850                 855                 860

Gly Val Tyr Asn Leu Leu Asn His Arg Tyr Val Thr Trp Glu Asn Val
865                 870                 875                 880

Arg Gln Thr Ala Ala Gly Ala Val Asn Gln His Lys Asn Val Gly Val
                885                 890                 895

Tyr Asn Arg Tyr Ala Ala Pro Gly Arg Asn Tyr Thr Phe Ser Leu Glu
                900                 905                 910

Met Lys Phe
        915
```

(2) INFORMATION FOR SEQ ID NO:19:

(i) SEQUENCE CHARACTERISTICS:
        (A) LENGTH: 657 amino acids
        (B) TYPE: amino acid
        (C) STRANDEDNESS: single
        (D) TOPOLOGY: linear (xi) SEQUENCE DESCRIPTION: SEQ ID NO:19:

```
Met Lys Ser Val Pro Leu Ile Ser Gly Gly Leu Ser Phe Leu Leu Ser
1               5                   10                  15

Ala Cys Ser Gly Gly Ser Phe Asp Val Asp Asn Val Ser Asn Thr
            20                  25                  30

Pro Ser Ser Lys Pro Arg Tyr Gln Asp Asp Thr Ser Asn Gln Arg Lys
            35                  40                  45

Lys Ser Asn Leu Lys Lys Leu Phe Ile Ser Leu Gly Tyr Gly Met Lys
        50                  55                  60

Leu Val Ala Gln Asn Leu Arg Gly Asn Lys Glu Pro Ser Phe Leu Asn
65                  70                  75                  80

Glu Asp Asp Tyr Ile Ser Tyr Phe Ser Ser Leu Ser Thr Ile Glu Lys
                85                  90                  95

Asp Val Lys Asp Asn Lys Asn Gly Ala Asp Leu Ile Gly Ser Ile Asp
                100                 105                 110

Glu Pro Ser Thr Thr Asn Pro Pro Glu Lys His His Gly Gln Lys Tyr
            115                 120                 125

Val Tyr Ser Gly Leu Tyr Tyr Thr Pro Ser Trp Ser Leu Asn Asp Ser
        130                 135                 140

Lys Asn Lys Phe Tyr Leu Gly Tyr Tyr Gly Tyr Ala Phe Tyr Tyr Gly
145                 150                 155                 160

Asn Lys Thr Ala Thr Asn Leu Pro Val Asn Gly Val Val Lys Tyr Lys
                165                 170                 175

Gly Thr Trp Asp Phe Ile Thr Ala Thr Lys Asn Gly Lys Arg Tyr Pro
                180                 185                 190

Leu Leu Ser Asn Gly Gly Ser His Ala Tyr Tyr Arg Arg Ser Ala Ile
            195                 200                 205

Pro Glu Asp Ile Asp Leu Glu Asn Asp Ser Lys Asn Gly Asp Ile Gly
        210                 215                 220

Leu Ile Ser Glu Phe Ser Ala Asp Phe Gly Thr Lys Lys Leu Thr Gly
```

```
               225                 230                 235                 240

Gln Leu Ser Tyr Thr Lys Arg Lys Thr Asn Gln Pro Tyr Glu Lys
                         245                 250                 255

Lys Lys Leu Tyr Asp Ile Asp Ala Asp Ile Tyr Ser Asn Arg Phe Arg
                 260                 265                 270

Gly Thr Val Lys Pro Thr Glu Lys Asp Ser Glu Glu His Pro Phe Thr
                 275                 280                 285

Ser Glu Gly Thr Leu Glu Gly Gly Phe Tyr Pro Asn Ala Glu Glu Leu
         290                 295                 300

Gly Gly Lys Phe Leu Ala Thr Asp Asn Arg Val Phe Gly Val Phe Ser
     305                 310                 315                 320

Ala Lys Glu Thr Glu Glu Thr Lys Lys Glu Ala Leu Ser Lys Glu Thr
                     325                 330                 335

Leu Ile Asp Gly Lys Leu Ile Thr Phe Ser Thr Lys Lys Thr Asp Ala
                     340                 345                 350

Lys Thr Asn Ala Thr Thr Ser Thr Ala Ala Asn Thr Thr Thr Asp Thr
                 355                 360                 365

Thr Ala Asn Thr Ile Thr Asp Glu Lys Asn Phe Lys Thr Glu Asp Ile
             370                 375                 380

Ser Ser Phe Gly Glu Ala Asp Tyr Leu Leu Ile Asp Lys Tyr Pro Ile
     385                 390                 395                 400

Pro Leu Leu Pro Asp Lys Asn Thr Asn Asp Phe Ile Ser Ser Lys His
                     405                 410                 415

His Thr Val Gly Asn Lys Arg Tyr Lys Val Glu Ala Cys Cys Ser Asn
                 420                 425                 430

Leu Tyr Val Lys Phe Gly Met Tyr Tyr Glu Asp Pro Leu Lys Glu Lys
                 435                 440                 445

Glu Thr Glu Thr Glu Thr Glu Thr Lys Asp Lys Glu Lys Glu Lys
         450                 455                 460

Glu Lys Asp Lys Asp Lys Glu Lys Gln Thr Ala Ala Thr Thr Asn Thr
     465                 470                 475                 480

Tyr Tyr Gln Phe Leu Leu Gly His Arg Thr Pro Lys Asp Asp Ile Pro
                     485                 490                 495

Lys Thr Gly Ser Ala Lys Tyr His Gly Ser Trp Phe Gly Tyr Ile Thr
                 500                 505                 510

Asp Gly Lys Thr Ser Tyr Ser Pro Ser Gly Asp Lys Lys Arg Asp Lys
             515                 520                 525

Asn Ala Val Ala Glu Phe Asn Val Asp Phe Ala Glu Lys Lys Leu Thr
     530                 535                 540

Gly Glu Leu Lys Arg His Asp Thr Gly Asn Pro Val Phe Ser Ile Glu
     545                 550                 555                 560

Ala Asn Phe Asn Asn Ser Ser Asn Ala Phe Thr Gly Thr Ala Thr Ala
                     565                 570                 575

Thr Asn Phe Val Ile Asp Gly Lys Asn Ser Gln Asn Lys Asn Thr Pro
                 580                 585                 590

Ile Asn Ile Thr Thr Lys Val Asn Gly Ala Phe Tyr Gly Pro Lys Ala
                 595                 600                 605

Ser Glu Leu Gly Gly Tyr Phe Thr Tyr Asn Gly Asn Ser Thr Ala Thr
             610                 615                 620

Asn Ser Glu Ser Ser Ser Thr Val Ser Ser Ser Asn Ser Lys Asn
     625                 630                 635                 640

Ala Arg Ala Ala Val Val Phe Gly Ala Arg Gln Gln Val Glu Thr Thr
                     645                 650                 655
```

Lys (2) INFORMATION FOR SEQ ID NO:20:

(i) SEQUENCE CHARACTERISTICS:
        (A) LENGTH: 601 amino acids
        (B) TYPE: amino acid
        (C) STRANDEDNESS: single
        (D) TOPOLOGY: linear (xi) SEQUENCE DESCRIPTION: SEQ ID NO:20:

```
Met Asn Asn Pro Leu Val Asn Gln Ala Ala Met Val Leu Pro Val Phe
 1               5                  10                  15

Leu Leu Ser Ala Cys Leu Gly Gly Gly Gly Ser Phe Asp Leu Asp Ser
                20                  25                  30

Val Glu Thr Val Gln Asp Met His Ser Lys Pro Lys Tyr Glu Asp Glu
            35                  40                  45

Lys Ser Gln Pro Glu Ser Gln Gln Asp Val Ser Glu Asn Ser Gly Ala
        50                  55                  60

Ala Tyr Gly Phe Ala Val Lys Leu Pro Arg Arg Asn Ala His Phe Asn
65                  70                  75                  80

Pro Lys Tyr Lys Glu Lys His Lys Pro Leu Gly Ser Met Asp Trp Lys
                85                  90                  95

Lys Leu Gln Arg Gly Glu Pro Asn Ser Phe Ser Glu Arg Asp Glu Leu
                100                 105                 110

Glu Lys Lys Arg Gly Ser Ser Glu Leu Ile Glu Ser Lys Trp Glu Asp
            115                 120                 125

Gly Gln Ser Arg Val Val Gly Tyr Thr Asn Phe Thr Tyr Val Arg Ser
130                 135                 140

Gly Tyr Val Tyr Leu Asn Lys Asn Asn Ile Asp Ile Lys Asn Asn Ile
145                 150                 155                 160

Val Leu Phe Gly Pro Asp Gly Tyr Leu Tyr Lys Gly Lys Glu Pro
                165                 170                 175

Ser Lys Glu Leu Pro Ser Glu Lys Ile Thr Tyr Lys Gly Thr Trp Asp
            180                 185                 190

Tyr Val Thr Asp Ala Met Glu Lys Gln Arg Phe Glu Gly Leu Gly Ser
        195                 200                 205

Ala Ala Gly Gly Asp Lys Ser Gly Ala Leu Ser Ala Leu Glu Glu Gly
    210                 215                 220

Val Leu Arg Asn Gln Ala Glu Ala Ser Ser Gly His Thr Asp Phe Gly
225                 230                 235                 240

Met Thr Ser Glu Phe Glu Val Asp Phe Ser Asp Lys Thr Ile Lys Gly
                245                 250                 255

Thr Leu Tyr Arg Asn Asn Arg Ile Thr Gln Asn Asn Ser Glu Asn Lys
                260                 265                 270

Gln Ile Lys Thr Thr Arg Tyr Thr Ile Gln Ala Thr Leu His Gly Asn
            275                 280                 285

Arg Phe Lys Gly Lys Ala Leu Ala Ala Asp Lys Gly Ala Thr Asn Gly
290                 295                 300

Ser His Pro Phe Ile Ser Asp Ser Asp Ser Leu Glu Gly Gly Phe Tyr
305                 310                 315                 320

Gly Pro Lys Gly Glu Glu Leu Ala Gly Lys Phe Leu Ser Asn Asp Asn
                325                 330                 335

Lys Val Ala Ala Val Phe Gly Ala Lys Gln Lys Asp Lys Lys Asp Gly
                340                 345                 350
```

```
Glu Asn Ala Ala Gly Pro Ala Thr Glu Thr Val Ile Asp Ala Tyr Arg
            355                 360                 365
Ile Thr Gly Glu Glu Phe Lys Lys Glu Gln Ile Asp Ser Phe Gly Asp
        370                 375                 380
Val Lys Lys Leu Leu Val Asp Gly Val Glu Leu Ser Leu Leu Pro Ser
385                 390                 395                 400
Glu Gly Asn Lys Ala Ala Phe Gln His Glu Ile Glu Gln Asn Gly Val
                405                 410                 415
Lys Ala Thr Val Cys Cys Ser Asn Leu Asp Tyr Met Ser Phe Gly Lys
            420                 425                 430
Leu Ser Lys Glu Asn Lys Asp Asp Met Phe Leu Gln Gly Val Arg Thr
            435                 440                 445
Pro Val Ser Asp Val Ala Ala Arg Thr Glu Ala Asn Ala Lys Tyr Arg
            450                 455                 460
Gly Thr Trp Tyr Gly Tyr Ile Ala Asn Gly Thr Ser Trp Ser Gly Glu
465                 470                 475                 480
Ala Ser Asn Gln Phe Thr Glu Gly Gly Asn Arg Ala Glu Phe Asp Val
                485                 490                 495
Asp Phe Ser Thr Lys Lys Ile Ser Gly Thr Leu Thr Ala Lys Asp Arg
            500                 505                 510
Thr Ser Pro Ala Phe Thr Ile Thr Ala Met Ile Lys Asp Asn Gly Phe
            515                 520                 525
Ser Gly Val Ala Lys Thr Gly Glu Asn Gly Phe Ala Leu Asp Pro Gln
            530                 535                 540
Asn Thr Gly Asn Ser His Tyr Thr His Ile Glu Ala Thr Val Ser Gly
545                 550                 555                 560
Gly Phe Tyr Gly Lys Asn Ala Ile Glu Met Gly Gly Ser Phe Ser Phe
                565                 570                 575
Pro Gly Asn Ala Pro Glu Gly Lys Glu Lys Ala Ser Val Val Phe
                580                 585                 590
Gly Ala Lys Arg Gln Gln Leu Val Gln
            595                 600

(2) INFORMATION FOR SEQ ID NO:21:

(i) SEQUENCE CHARACTERISTICS:
        (A) LENGTH: 711 amino acids
        (B) TYPE: amino acid
        (C) STRANDEDNESS: single
        (D) TOPOLOGY: linear (xi) SEQUENCE DESCRIPTION: SEQ ID NO:21:

Met Asn Asn Pro Leu Val Asn Gln Ala Ala Met Val Leu Pro Val Phe
1               5                   10                  15
Leu Leu Ser Ala Cys Leu Gly Gly Gly Ser Phe Asp Leu Asp Ser
            20                  25                  30
Val Asp Thr Glu Ala Pro Arg Pro Ala Pro Lys Tyr Gln Asp Val Ser
            35                  40                  45
Ser Glu Lys Pro Gln Ala Gln Gln Asp Gln Gly Gly Tyr Gly Phe Ala
50                  55                  60
Met Arg Leu Lys Arg Arg Asn Trp Tyr Pro Gly Ala Glu Glu Ser Glu
65                  70                  75                  80
Val Lys Leu Asn Glu Ser Asp Trp Glu Ala Thr Gly Leu Pro Thr Lys
                85                  90                  95
Pro Lys Glu Leu Pro Lys Arg Gln Lys Ser Val Ile Glu Lys Val Glu
```

-continued

```
                100                 105                 110
Thr Asp Gly Asp Ser Asp Ile Tyr Ser Ser Pro Tyr Leu Thr Pro Ser
            115                 120                 125

Asn His Gln Asn Gly Ser Ala Gly Asn Gly Val Asn Gln Pro Lys Asn
130                 135                 140

Gln Ala Thr Gly His Glu Asn Phe Gln Tyr Val Tyr Ser Gly Trp Phe
145                 150                 155                 160

Tyr His Ala Ala Ser Glu Lys Asp Phe Ser Asn Lys Lys Ile Trp Lys
            165                 170                 175

Ser Gly Asp Asp Gly Tyr Ile Phe Tyr His Gly Glu Lys Pro Ser Arg
            180                 185                 190

Gln Leu Pro Ala Ser Gly Lys Val Ile Tyr Lys Gly Val Trp His Phe
            195                 200                 205

Val Thr Asp Thr Lys Lys Gly Gln Asp Phe Arg Glu Ile Ile Gln Pro
210                 215                 220

Ser Lys Lys Gln Gly Asp Arg Tyr Ser Gly Phe Ser Gly Asp Gly Ser
225                 230                 235                 240

Glu Glu Tyr Ser Asn Lys Asn Ser Thr Leu Lys Asp Asp His Glu
            245                 250                 255

Gly Tyr Gly Phe Thr Ser Asn Leu Glu Val Asp Phe Gly Asn Lys Lys
            260                 265                 270

Leu Thr Gly Lys Leu Ile Arg Asn Asn Ala Ser Leu Asn Asn Thr
            275                 280                 285

Asn Asn Asp Lys His Thr Thr Gln Tyr Tyr Ser Leu Asp Ala Gln Ile
290                 295                 300

Thr Gly Gly Asn Pro Phe Asn Gly Thr Ala Thr Ala Thr Asp Lys Lys
305                 310                 315                 320

Glu Asn Glu Thr Lys Leu His Pro Phe Val Ser Asp Ser Ser Ser Leu
            325                 330                 335

Glu Gly Gly Phe Phe Gly Pro Gln Gly Glu Leu Gly Phe Arg Phe
            340                 345                 350

Leu Thr Asp Asp Gln Lys Val Ala Val Val Gly Ser Ala Lys Thr Lys
            355                 360                 365

Asp Lys Leu Glu Asn Gly Ala Ala Ala Ser Gly Ser Ala Ala Ala
370                 375                 380

Ser Gly Gly Ala Ala Gly Thr Ser Ser Glu Asn Ser Lys Leu Thr Thr
385                 390                 395                 400

Val Leu Asp Ala Val Glu Leu Thr Leu Asn Asp Lys Lys Ile Lys Asn
            405                 410                 415

Leu Asp Asn Phe Ser Asn Ala Ala Gln Leu Val Val Asp Gly Ile Met
            420                 425                 430

Ile Pro Leu Leu Pro Lys Asp Ser Glu Ser Gly Asn Thr Gln Ala Asp
            435                 440                 445

Lys Gly Lys Asn Gly Gly Thr Glu Phe Thr Arg Lys Phe Glu His Thr
450                 455                 460

Pro Glu Ser Asp Lys Lys Asp Ala Gln Ala Gly Thr Gln Thr Asn Gly
465                 470                 475                 480

Ala Gln Thr Ala Ser Asn Thr Ala Gly Asp Thr Asn Gly Lys Thr Lys
            485                 490                 495

Thr Tyr Glu Val Glu Val Cys Cys Ser Asn Leu Asn Tyr Leu Lys Tyr
            500                 505                 510

Gly Met Leu Thr Arg Lys Asn Ser Lys Ser Ala Met Gln Ala Gly Gly
            515                 520                 525
```

```
Asn Ser Ser Gln Ala Asp Ala Lys Thr Glu Gln Val Glu Gln Ser Met
        530                 535                 540

Phe Leu Gln Gly Glu Arg Thr Asp Glu Lys Glu Ile Pro Thr Asp Gln
545                 550                 555                 560

Asn Val Val Tyr Arg Gly Ser Trp Tyr Gly His Ile Ala Asn Gly Thr
                565                 570                 575

Ser Trp Ser Gly Asn Ala Ser Asp Lys Glu Gly Gly Asn Arg Ala Asp
                580                 585                 590

Phe Thr Ile Asn Phe Ala Asp Lys Lys Ile Thr Gly Lys Leu Thr Ala
            595                 600                 605

Glu Asn Arg Thr Ala Gln Thr Phe Thr Ile Gly Met Ile Gln Gly
610                 615                 620

Asn Gly Phe Glu Gly Thr Ala Lys Thr Ala Glu Ser Gly Phe Asp Leu
625                 630                 635                 640

Asp Gln Lys Asn Thr Thr Arg Thr Pro Lys Ala Tyr Ile Thr Asp Ala
                645                 650                 655

Lys Val Lys Gly Gly Phe Tyr Gly Pro Lys Ala Glu Glu Leu Gly Gly
                660                 665                 670

Trp Phe Ala Tyr Pro Gly Asp Lys Gln Thr Glu Lys Ala Thr Ala Thr
                675                 680                 685

Ser Ser Asp Gly Asn Ser Ala Ser Ala Thr Val Val Phe Gly Ala
        690                 695                 700

Lys Arg Gln Gln Pro Val Gln
705                 710

(2) INFORMATION FOR SEQ ID NO:22:

(i) SEQUENCE CHARACTERISTICS:
        (A) LENGTH: 708 amino acids
        (B) TYPE: amino acid
        (C) STRANDEDNESS: single
        (D) TOPOLOGY: linear (xi) SEQUENCE DESCRIPTION: SEQ ID NO:22:

Met Asn Asn Pro Leu Val Asn Gln Ala Ala Met Val Leu Pro Val Phe
1               5                   10                  15

Leu Leu Ser Ala Cys Leu Gly Gly Gly Gly Ser Phe Asp Leu Asp Ser
            20                  25                  30

Val Asp Thr Glu Ala Pro Arg Pro Ala Pro Lys Tyr Gln Asp Val Ser
        35                  40                  45

Ser Glu Lys Pro Gln Ala Gln Lys Asp Gln Gly Gly Tyr Gly Phe Ala
50                  55                  60

Met Arg Phe Lys Arg Arg Asn Trp His Pro Ser Ala Asn Pro Lys Glu
65                  70                  75                  80

Asp Glu Val Lys Leu Lys Asn Asp Asp Trp Glu Ala Thr Gly Leu Pro
                85                  90                  95

Thr Glu Pro Lys Lys Leu Pro Leu Lys Gln Gln Ser Val Ile Ser Glu
                100                 105                 110

Val Glu Thr Asn Gly Asn Ser Lys Met Tyr Thr Ser Pro Tyr Leu Ser
            115                 120                 125

Gln Asp Ala Asp Ser Ser His Ala Asn Gly Ala Asn Gln Pro Lys Asn
        130                 135                 140

Glu Val Thr Asp Tyr Lys Lys Phe Lys Tyr Val Tyr Ser Gly Trp Phe
145                 150                 155                 160

Tyr Lys His Ala Lys Ser Glu Val Lys Asn Glu Asn Gly Leu Val Ser
```

-continued

```
                165                 170                 175
Ala Lys Arg Gly Asp Asp Gly Tyr Ile Phe Tyr His Gly Asp Lys Pro
                    180                 185                 190
Ser Arg Gln Leu Pro Ala Ser Glu Ala Val Thr Tyr Lys Gly Val Trp
                195                 200                 205
His Phe Val Thr Asp Thr Lys Gln Gly Gln Lys Phe Asn Asp Ile Leu
            210                 215                 220
Glu Thr Ser Lys Gly Gln Gly Asp Lys Tyr Ser Gly Phe Ser Gly Asp
225                 230                 235                 240
Glu Gly Glu Thr Thr Ser Asn Arg Thr Asp Ser Asn Leu Asn Asp Lys
                    245                 250                 255
His Glu Gly Tyr Gly Phe Thr Ser Asn Phe Lys Val Asp Phe Asn Asn
                260                 265                 270
Lys Lys Leu Thr Gly Lys Leu Ile Arg Asn Asn Lys Val Ile Asn Thr
            275                 280                 285
Ala Ala Ser Asp Gly Tyr Thr Thr Glu Tyr Tyr Ser Leu Asp Ala Thr
        290                 295                 300
Leu Arg Gly Asn Arg Phe Ser Gly Lys Ala Ile Ala Thr Asp Lys Pro
305                 310                 315                 320
Asn Thr Gly Gly Thr Lys Leu His Pro Phe Val Phe Asp Ser Ser Ser
                325                 330                 335
Leu Ser Gly Gly Phe Phe Gly Pro Gln Gly Glu Glu Leu Gly Phe Arg
            340                 345                 350
Phe Leu Ser Asp Asp Gly Lys Val Ala Val Gly Ser Ala Lys Thr
        355                 360                 365
Lys Asp Ser Thr Ala Asn Gly Asn Ala Pro Ala Ser Ser Gly Pro
370                 375                 380
Gly Ala Ala Thr Met Pro Ser Glu Thr Arg Leu Thr Thr Val Leu Asp
385                 390                 395                 400
Ala Val Glu Leu Thr Pro Asp Gly Lys Glu Ile Lys Asn Leu Asp Asn
                405                 410                 415
Phe Ser Asn Ala Thr Arg Leu Val Val Asp Gly Ile Met Ile Pro Leu
            420                 425                 430
Leu Pro Thr Glu Ser Gly Asn Gly Gln Ala Asp Lys Gly Lys Asn Gly
        435                 440                 445
Gly Thr Asp Phe Thr Tyr Glu Thr Thr Tyr Thr Pro Glu Ser Asp Lys
450                 455                 460
Lys Asp Thr Lys Ala Gln Thr Gly Ala Gly Met Gln Thr Ala Ser
465                 470                 475                 480
Gly Thr Ala Thr Val Asn Gly Gly Gln Val Gly Thr Lys Thr Tyr Lys
                485                 490                 495
Val Gln Val Cys Cys Ser Asn Leu Asn Tyr Leu Lys Tyr Gly Leu Leu
                500                 505                 510
Thr Arg Glu Asn Asn Asn Ser Val Met Gln Ala Val Lys Asn Ser Ser
            515                 520                 525
Gln Ala Asp Ala Lys Thr Lys Gln Ile Glu Gln Ser Met Phe Leu Gln
        530                 535                 540
Gly Glu Arg Thr Asp Glu Asn Lys Ile Pro Gln Glu Gln Gly Ile Val
545                 550                 555                 560
Tyr Arg Gly Phe Trp Tyr Gly Arg Ile Ala Asn Gly Thr Ser Trp Ser
                565                 570                 575
Gly Lys Ala Ser Asn Ala Thr Asp Gly Asn Arg Ala Lys Phe Thr Val
            580                 585                 590
```

```
Asn Gly Asp Arg Lys Glu Ile Thr Gly Thr Leu Thr Ala Glu Asn Arg
        595                 600                 605

Ser Glu Ala Thr Phe Thr Ile Asp Ala Met Ile Glu Gly Asn Gly Phe
    610                 615                 620

Lys Gly Thr Ala Lys Thr Gly Asn Asp Gly Phe Ala Pro Asp Gln Asn
625                 630                 635                 640

Asn Ser Thr Val Thr His Lys Val His Ile Ala Asn Ala Glu Val Gln
                645                 650                 655

Gly Gly Phe Tyr Gly Pro Asn Ala Glu Glu Leu Gly Gly Trp Phe Ala
            660                 665                 670

Tyr Pro Gly Asn Glu Gln Thr Lys Asn Ala Thr Val Glu Ser Gly Asn
        675                 680                 685

Gly Asn Ser Ala Ser Ser Ala Thr Val Val Phe Gly Ala Lys Arg Gln
    690                 695                 700

Lys Leu Val Lys
705
```

(2) INFORMATION FOR SEQ ID NO:23:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:23:

Glu Gly Gly Phe Tyr Gly Pro
1               5

(2) INFORMATION FOR SEQ ID NO:24:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (xi) SEQUENCE DESCRIPTION: SEQ ID NO:24:

AGCCAACGAA GTTACAGGGC TTGGTAAGGT GGTCAAAACT GCCGAGACCA TCAATAAAGA     60

ACAAGTGCTA ACATTCGAG ACTTAACACG CTATGACCCT GGCATTGCTG TGGTTGAGCA    120

AGGTCGTGGG GCAAGCTCAG GCTATTCTAT TCGTGGTATG GATAAAAATC GTGTGGCGGT   180

ATTGGTTGAT GGCATCAATC AAGCCCAGCA CTATGCCCTA CAAGGCCCTG TGGCAGGCAA   240

AAATTATGCC GCAGGTGGGG CAATCAACGA AATAGAATAC                         280

(2) INFORMATION FOR SEQ ID NO:25:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:25:

AATCAATCAA ACAAAACAA CAAATCCAAA AAATCCAAAC AAGTATTAAA ACTTAGTGCC      60

(2) INFORMATION FOR SEQ ID NO:26:

(i) SEQUENCE CHARACTERISTICS:
        (A) LENGTH: 57 base pairs
        (B) TYPE: nucleic acid -continued

```
            (C) STRANDEDNESS: single
            (D) TOPOLOGY: linear (xi) SEQUENCE DESCRIPTION: SEQ ID NO:26:

AAACACATTC CTTTAACCAC ACTGTGTGTG GCAATCTCTG CCGTCTTATT AACCGCT          57

(2) INFORMATION FOR SEQ ID NO:27:

(i) SEQUENCE CHARACTERISTICS:
            (A) LENGTH: 10 amino acids
            (B) TYPE: amino acid
            (C) STRANDEDNESS: single
            (D) TOPOLOGY: linear (xi) SEQUENCE DESCRIPTION: SEQ ID NO:27:

Ile Arg Asp Leu Thr Arg Tyr Asp Pro Gly
1               5                   10

(2) INFORMATION FOR SEQ ID NO:28:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:28:

ATTCGAGACT TAACACGCTA TGACCCTGGC                                        30

(2) INFORMATION FOR SEQ ID NO:29:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:29:

ATTCGTGATT TAACTCGCTA TGACCCTGGT                                        30

(2) INFORMATION FOR SEQ ID NO:30:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (xi) SEQUENCE DESCRIPTION: SEQ ID NO:30:

TCGACGGTAT CGATGGCCTT AGGGGCCTAG GA                                     32

(2) INFORMATION FOR SEQ ID NO:31:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (xi) SEQUENCE DESCRIPTION: SEQ ID NO:31:

GCCATAGCTA CCGGAATCCC CGGATCCTTC GA                                     32
```

DNA ENCODING A TRANSFERRIN RECEPTOR OF MORAXELLA

FIELD OF INVENTION

The present invention relates to the molecular cloning of genes encoding transferrin receptor and in particular to the cloning of transferring receptor genes from Moraxella (Branhamella) *M. catarrhalis*.

BACKGROUND OF THE INVENTION

*Moraxella* (Branhamella) *catarrhalis* bacteria are Gram-negative diplococcal pathogens which are carried asymptomatically in the healthy human respiratory tract. In recent years, *M. caterrhalis* has been recognized as an important causative agent of otitis media. In addition, *M. catarrhalis* has been associated with sinusitis, conjunctivitis, and urogenital infections, as well as with a number of inflammatory diseases of the lower respiratory tract in children and adults, including pneumonia, chronic bronchitis, tracheitis, and emphysema (refs. 1 to 8). (Throughout this application, various references are cited in parentheses to describe more fully the state of the art to which this invention pertains. Full bibliographic information for each citation is found at the end of the specification, immediately preceding the claims. The disclosures of these references are hereby incorporated by reference into the present disclosure). Occasionally, *M. catarrhalis* invades to cause septicaemia, arthritis, endocarditis, and meningitis (refs. 9 to 13).

Otitis media is one of the most common illnesses of early childhood; approximately 80% of all children suffer at least one middle ear infection before the age of three (ref. 14). Chronic otitis media has been associated with auditory and speech impairment in children, and in some cases, has been associated with learning disabilities. Conventional treatments for otitis media include antibiotic administration and surgical procedures, including tonsillectomies, adenoidectomies, and tympanocentesis. In the United States, treatment costs for otitis media are estimated to be between one to two billion dollars per year.

In otitis media cases, *M. catarrhalis* commonly is co-isolated from middle ear fluid along with *Streptococcus pneumoniae* and non-typable *Haemophilus influenzae*, which are believed to be responsible for 50% and 30% of otitis media infections, respectively. *M. catarrhalis* is believed to be responsible for approximately 20% of otitis media infections (ref. 15). Epidemiological reports indicate that the number of cases of otitis media attributable to *M. catarrhalis* is increasing, along with the number of antibiotic-resistant isolates of *M. catarrhalis*. Thus, prior to 1970, no β-lactamase-producing *M. catarrhalis* isolates had been reported, but since the mid-seventies, an increasing number of β-lactamase-expressing isolates have been detected. Recent surveys suggest that 75% of clinical isolates produce β-lactamase (ref. 16, 26).

Iron is an essential nutrient for the growth of many bacteria. Several bacterial species, including *M. catarrhalis*, obtain iron from the host by using transferrin receptor proteins to capture transferring. A number of bacteria including *Neisseria meningitidis* (ref. 17), *N. gonorrhoeae* (ref. 18), *Haemophilus influenzae* (ref. 19), as well as *M. catarrhalis* (ref. 20), produce outer membrane proteins which specifically bind human transferrin. The expression of these proteins is regulated by the amount of iron in the environment.

The two transferring receptor proteins of *M. catarrhalis*, designated transferrin binding protein 1 (Tbp1) and transferrin binding protein 2 (Tbp2), have molecular weights of 115 kDa (Tbp1) and approximately 80 to 90 kDa (Tbp2). Unlike the transferrin receptor proteins of other bacteria which have an affinity for apotransferrin, the *M. catarrhalis* Tbp2 receptors have a preferred affinity for iron-saturated (i.e., ferri-) transferrin (ref. 21).

*M. catarrhalis* infection may lead to serious disease. It would be advantageous to provide a recombinant source of transferrin binding proteins as antigens in immunogenic preparations including vaccines, carriers for other antigens and immunogens and the generation of diagnostic reagents. The genes encoding transferrin binding proteins and fragments thereof are particularly desirable and useful in the specific identification and diagnosis of Moraxella and for immunization against disease caused by *M. catarrhalis* and for the generation of diagnostic reagents.

SUMMARY OF THE INVENTION

The present invention is directed towards the provision of purified and isolated nucleic acid molecules encoding a transferrin receptor of a strain of Moraxella or a fragment or an analog of the transferring receptor protein. The nucleic acid molecules provided herein are useful for the specific detection of strains of Moraxella and for diagnosis of infection by Moraxella. The purified and isolated nucleic acid molecules provided herein, such as DNA, are also useful for expressing the tbp genes by recombinant DNA means for providing, in an economical manner, purified and isolated transferrin receptor proteins as well as subunits, fragments or analogs thereof. The transferrin receptor, subunits or fragments thereof or analogs thereof, as well as nucleic acid molecules encoding the same and vectors containing such nucleic acid molecules, are useful in immunogenic compositions for vaccinating against diseases caused by Moraxella, the diagnosis of infection by Moraxella and as tools for the generation of immunological reagents. Monoclonal antibodies or mono-specific antisera (antibodies) raised against the transferrin receptor protein produced in accordance with aspects of the present invention are useful for the diagnosis of infection by Moraxella, the specific detection of Moraxella (in, for example, in vitro and in vivo assays) and for the treatment of diseases caused by Moraxella.

In accordance with one aspect of the present invention, there is provided a purified and isolated nucleic acid molecule encoding a transferrin receptor protein of a strain of Moraxella, more particularly, a strain of *M. catarrhalis*, specifically *M. catarrhalis* strain 4223 or Q8, or a fragment or an analog of the transferring receptor protein.

In one preferred embodiment of the invention, the nucleic acid molecule may encode only the Tbp1 protein of the Moraxella strain or only the Tbp2 protein of the Moraxella strain. In another preferred embodiment of the invention, the nucleic acid may encode a fragment of the transferrin receptor protein of a strain of Moraxella having a conserved amino acid sequence which is conserved.

In another aspect of the present invention, there is provided a purified and isolated nucleic acid molecule having a DNA sequence selected from the group consisting of (a) a DNA sequence as set out in FIGS. 5, 6 or 9 (SEQ ID Nos: 1, 2, 3, 4, 5 or 6) or the complementary DNA sequence of any one of said sequences; (b) a DNA sequence encoding an amino acid sequence as set out in FIG. 5, 6 or 9 (SEQ ID Nos: 7, 8, 9, 10, 11 or 12) or the complementary DNA sequence thereto; and (c) a DNA sequence which hybridizes under stringent conditions to any one of the DNA sequences defined in (a) or (b). The DNA sequence defined in (c) preferably has at least about 90% sequence identity with any one of the DNA sequences defined in (a) and (b). The DNA sequence defined in (c) may be that encoding the equivalent transferrin receptor protein from another strain of Moraxella.

In an additional aspect, the present invention includes a vector adapted for transformation of a host, comprising a nucleic acid molecule as provided herein and may have the characteristics of a nucleotide sequence contained within vectors LEM3-24, pLEM25, pLEM23, SLRD-A, DS-1698-1-1, DS-1754-1, pSLRD1, pSLRD2, SLRD3 and pSLRD4.

The vector may be adapted for expression of the encoded transferrin receptor, fragments or analogs thereof, in a heterologous or homologous host, in either a lipidated or non-lipidated form. Accordingly, a further aspect of the present invention provides an expression vector adapted for transformation of a host comprising a nucleic acid molecule as provided herein and expression means operatively coupled to the nucleic acid molecule for expression by the host of the transferrin receptor protein or the fragment or analog of the transferrin receptor protein. In specific embodiments of this aspect of the invention, the nucleic acid molecule may encode substantially all the transferrin receptor protein, only the Tbp1 protein, only the Tbp2 protein of the Moraxella strain or fragments of the Tbp1 or Tbp2 proteins. The expression means may include a promoter and a nucleic acid portion encoding a leader sequence for secretion from the host of the transferrin receptor protein or the fragment or the analog of the transferrin receptor protein. The expression means also may include a nucleic acid portion encoding a lipidation signal for expression from the host of a lipidated form of the transferrin receptor protein or the fragment or the analog of the transferrin receptor protein. The host may be selected from, for example, *Escherichia coli,* Bordetella, Bacillus, Haemophilus, Moraxella, fungi, yeast or baculovirus and Semliki Forest virus expression systems may be used. In a particular embodiment the plasmid adapted for expression of Tbp1 is pLEM29 and that for expression of Tbp2 is pLEM33.

In an additional aspect of the invention, there is provided a transformed host containing an expression vector as provided herein. The invention further includes a recombinant transferrin receptor protein or fragment of analog thereof of a strain of Moraxella producible by the transformed host.

Such recombinant transferrin receptor protein may be required in substantially pure form according to a further aspect of the invention, which comprises a method of forming a substantially pure recombinant transferrin receptor protein, which comprises growing the transformed host provided herein to express a transferrin receptor protein as inclusion antibodies, purifying the inclusion bodies free from cellular material and soluble proteins, solubilizing transferrin receptor protein from the purified inclusion bodies, and purifying the transferrin receptor protein free from other solubilized materials. The substantially pure recombinant transferrin receptor protein may comprise Tbp1 alone, Tbp2 alone or a mixture thereof. The recombinant protein is generally at least about 70% pure, preferably at least about 90% pure.

Further aspects of the present invention, therefore, provide recombinantly-produced Tbp1 protein of a strain of Moraxella devoid of the Tbp2 protein of the Moraxella strain and any other protein of the Moraxella strain and recombinantly-produced Tbp2 protein of a strain of Moraxella devoid of the Tbp1 protein of the Moraxella strain and any other protein of the Moraxella strain. The Moraxella strain may be *M. catarrhalis* 4223 strain or *M. catarrhalis* Q8.

In accordance with another aspect of the invention, an immunogenic composition is provided which comprises at least one active component selected from at least one nucleic acid molecule as provided herein and at least one recombinant protein as provided herein, and a pharmaceutically acceptable carrier therefor or vector therefor. The at least one active component produces an immune response when administered to a host.

The immunogenic compositions provided herein may be formulated as vaccines for in vivo administration to a host. For such purpose, the compositions may be formulated as a microparticle, capsule, ISCOM or liposome preparation. The immunogenic composition may be provided in combination with a targeting molecule for delivery to specific cells of the immune system or to mucosal surfaces. The immunogenic compositions of the invention (including vaccines) may further comprise at least one other immunogenic or immunostimulating material and the immunostimulating material may be at least one adjuvant or at least one cytokine. Suitable adjuvants for use in the present invention include (but are not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of an amino acid, a muramyl dipeptide polyphosphazene, ISCOPREP, DC-chol, DDBA and a lipoprotein. Advantageous combinations of adjuvants are described in copending U.S. patent application Ser. Nos. 08/261,194 filed Jun. 16, 1994 and 08/483,856, filed Jun. 7, 1995, assigned to the assignee hereof and the disclosure of which is incorporated herein by reference thereto.

In accordance with another aspect of the invention, there is provided a method for generating an immune response in a host, comprising the step of administering to a susceptible host, such as a human, an effective amount of the immunogenic composition as recited above. The immune response may be a humoral or a cell-mediated immune response and may provide protection against disease caused by Moraxella. Hosts in which protection against disease may be conferred include primates, including humans.

In a further aspect, there is provided a live vector for delivery of transferrin receptor to a host, comprising a vector containing the nucleic acid molecule as described above. The vector may be selected from Salmonella, BCG, adenovirus, poxvirus, vaccinia and poliovirus.

The nucleic acid molecules provided herein are useful in diagnostic applications. Accordingly, in a further aspect of the invention, there is provided a method of determining the present, in a sample, of nucleic acid encoding a transferrin receptor protein of a strain of Moraxella, comprising the steps of:

(a) contacting the sample with a nucleic acid molecule as provided herein to produce duplexes comprising the nucleic acid molecule encoding the transferrin receptor protein of a strain of Moraxella present in the sample and specifically hybridizable therewith; and (b) determining the production of the duplexes.

In addition, the present invention provides a diagnostic kit for determining the presence, in a sample, of nucleic acid encoding a transferrin receptor protein of a strain of Moraxella, comprising:

(a) a nucleic acid molecule as provided herein;

(b) means for contacting the nucleic acid molecule with the sample to produce duplexes comprising the nucleic acid molecule and any such nucleic acid present in the sample and hybridizable with the nucleic acid molecule; and (c) means for determining production of the duplexes.

The invention further includes the use of the nucleic acid molecules and proteins provided herein as medicines. The invention additionally includes the use of the nucleic acid molecules and proteins provided herein in the manufacture of medicaments for protection against infection by strains of Moraxella.

Advantages of the present invention include:

an isolated and purified nucleic acid molecule encoding a transferrin receptor protein of a strain of Moraxella or a fragment or an analog of the transferrin receptor protein;

recombinantly-produced transferrin receptor proteins, including Tbp1 and Tbp2, free from each other and other Moraxella protesin; and diagnostic kits and immunological reagents for specific identification of Moraxella.

BRIEF DESCRIPTION OF DRAWINGS

The present invention will be further understood from the following description with reference to the drawings, in which:

FIG. 1 shows the amino acid sequences (SEQ ID Nos: 13 and 14) used for synthesis of degenerate primers used for PCR amplification of a portion of the M. catarrhalis 4223 tbpA gene;

FIGS. 5A to 5J show the nucleotide sequence of the tbpA gene (SEQ ID No: 1—entire sequence and SEQ ID No: 2—coding sequence) and the deduced amino acid sequence of the Tbp1 protein from M. catarrhalis 4223 (SEQ ID No: 7—full length and SEQ ID No: 8—mature protein). The leader sequence (SEQ ID No: 25) is shown by underlining;

FIGS. 6A to 6G show the nucleotide sequence of the tbpB gene (SEQ ID No: 3—entire sequence and SEQ ID No: 4—coding sequence) and the deduced amino acid sequence of the Tbp2 protein from M. catarrhalis 4223 (SEQ ID Nos: 9—full length and SEQ ID No: 10—mature protein). The leader sequence (SEQ ID No: 26) is shown by underlining;

FIGS. 9A to 9Q show the nucleotide sequence of the tbpA gene (SEQ. ID No: 5—entire sequence and SEQ ID No: 6—coding sequence) and the deduced amino acid sequence of the Tbp1 protein from M. catarrhalis Q8 (SEQ ID No: 11—full length and SEQ ID No: 12—mature protein);

FIGS. 10A to 10G show a comparison of the amino acid sequences of Tbp1 from M. catarrhalis strain 4223 (SEQ ID No: 7) and Q8 (SEQ ID No: 11), H. influenzae strain Eagan (SEQ ID No: 15), N. meningitidis strains B16B6 (SEQ ID No: 16) and M982 (SEQ ID No: 17), and N. gonorrhoeae strain FA19 (SEQ ID No: 18);

FIGS. 11A to 11C show a comparison of the amino acid sequences of Tbp2 from M. catarrhalis isolate 4223 (SEQ ID No: 9), H. influenzae strain Eagan (SEQ ID No: 19), N. meningitidis strains B16B6 (SEQ ID No: 20) and M918 (SEQ ID No: 21), and N. gonorrhoeae strain FA19 (SEQ ID No: 22);

GENERAL DESCRIPTION OF THE INVENTION

Any Moraxella strain may be conveniently used to provide the purified and isolated nucleic acid, which may be in the form of DNA molecules, comprising at least a portion of the nucleic acid coding for a transferrin receptor sa typified by embodiments of the present invention. Such strains are generally available from clinical sources and from bacterial culture collections, such sa the American Type Culture Collection.

In this application, the terms "transferrin receptor" (TfR) and "transferrin binding proteins" (Tbp) are used to define a family of Tbp1 and/or Tbp2 proteins which includes those having variations in their amino acid sequences including those naturally occurring in various strains of, for example, Moraxella. The purified and isolated DNA molecules comprising at least a portion coding for transferrin receptor of the present invention also include those encoding functional analogs of transferrin receptor proteins Tbp1 and Tbp2 of Moraxella. In this application, a first protein is a "functional analog" of a second protein if the first protein is immunologically related to and/or has the same function as the second protein. The functional analog may be, for example, a fragment of the protein, or a substitution, addition or deletion mutant thereof.

Chromosomal DNA from M. catarrhalis 4223 was digested with Sau3A in order to generate fragments within a 15 to 23 kb size range, and cloned into the BamHI site of the lambda vector EMBL3. The library was screened with anti-Tbp1 guinea pig antisera, and a positive clone LEM3-24, containing an insert approximately 13.2 kb in size was selected for further analysis. Lysate from E. coli Le392 infected with LEM3-24 was found to contain a protein approximately 115 kDa in size, which reacted on Western blots with anti-Tbp1 antisera. A second protein, approximately 80 kDa in size, reacted with the anti-Tbp2 guinea pig antisera on Western blots.

In order to localize the tbpA gene on the 13.2 kb insert of LEM3-24, degenerate PCR primers were used to amplify a small region of the putative tbpA gene of M. catarrhalis 4223. The sequences of the degenerate oligonucleotide primers were based upon conserved amino acid sequences within the Tbp1 proteins of several Neisseria and Haemophilus species FIG. 1 (SEQ ID Nos: 13 and 14). A 300 base-pair amplified product was generated and its location within the 4223 tbpA gene is indicated by bold letters in FIG. 5 (SEQ ID No: 24). The amplified product was subcloned into the vector pCRII, labelled, and used to probe a Southern blot containing restriction-endonuclease digested clone LEM3-24 DNA. The probe hybridized to a 3.8 kb HindIII—

Figure 2:
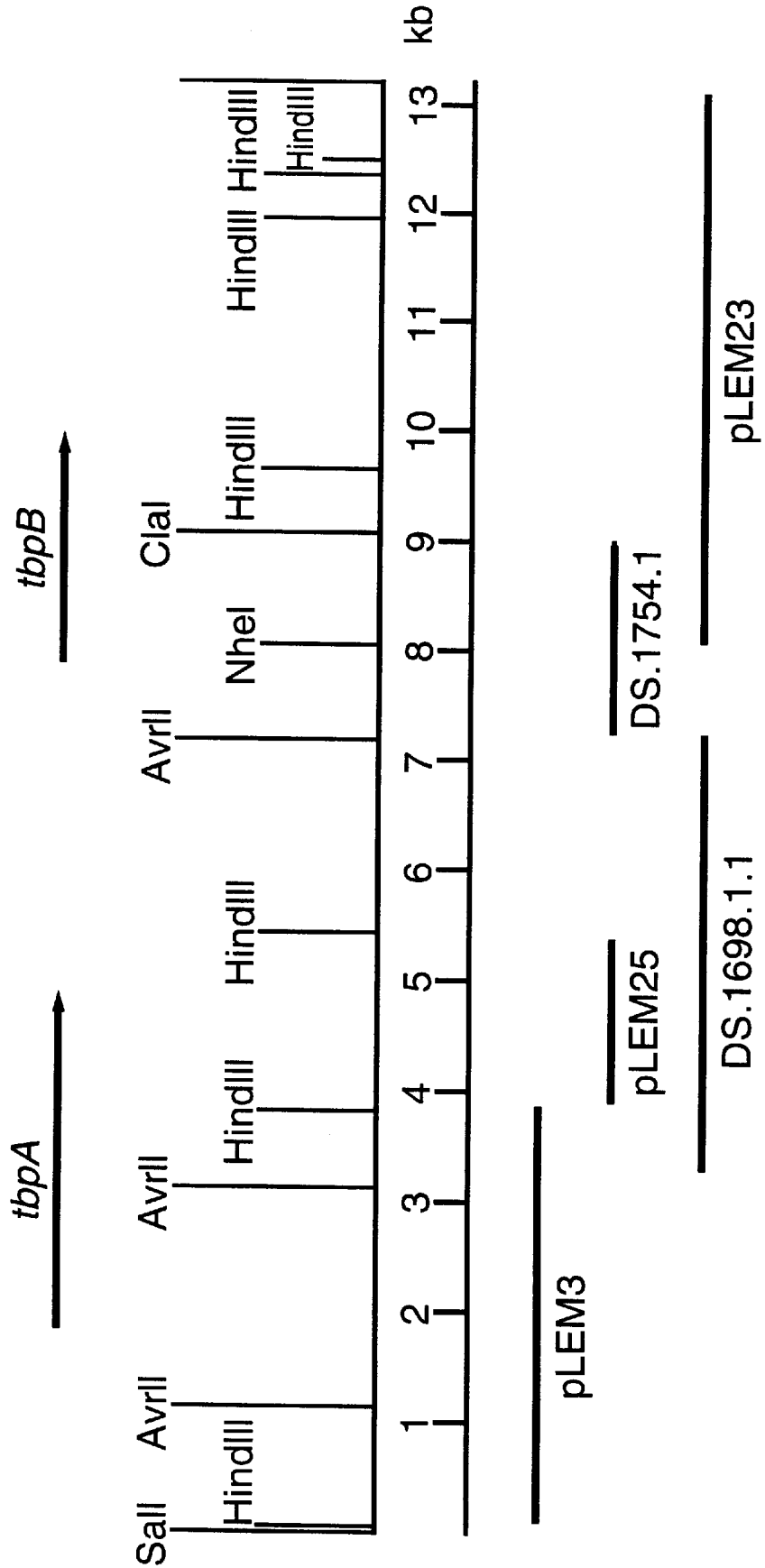
FIG. 2 shows a restriction map of clone LEM3-24 containing the tbpA and tbpB genes from M. catarrhalis isolate 4223.
Figure 3:
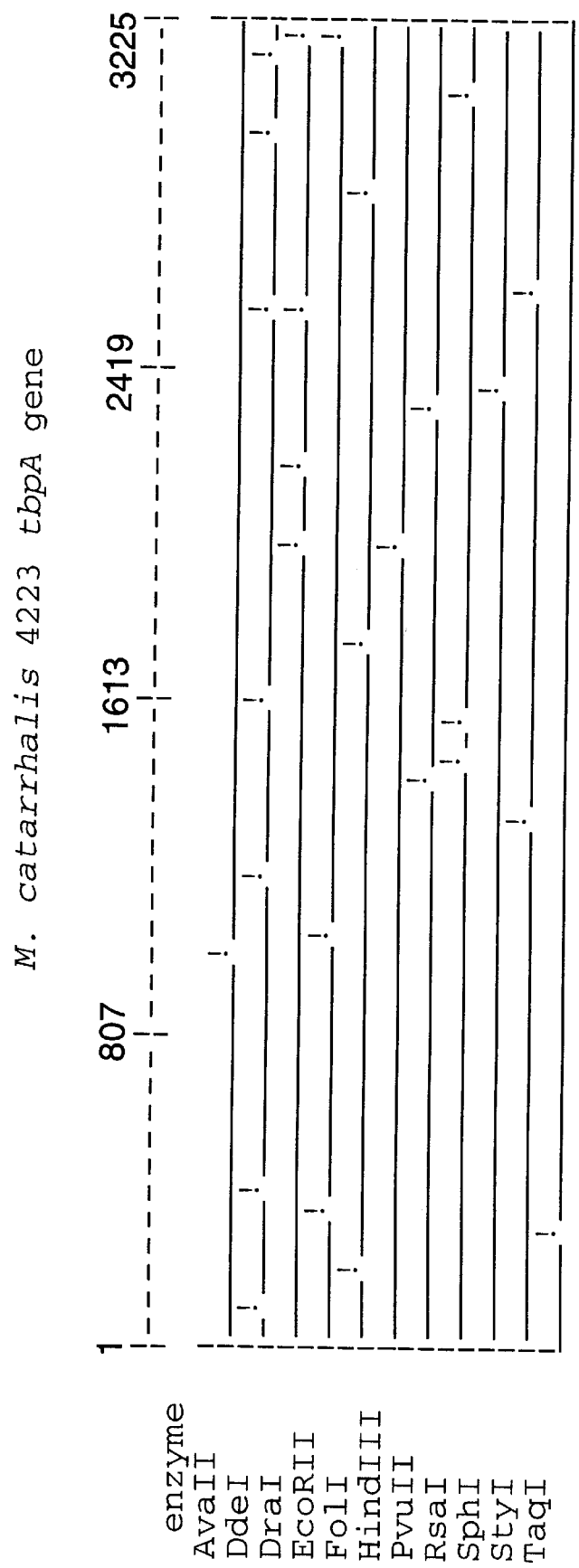
FIG. 3 shows a restriction map of the tbpA gene for M. catarrhalis 4223.

HindIII, a 2.0 kb AvrII—AvrII, and 4.2 kb SalI-SphI fragments (FIG. 2).

The 3.8 kb HindIII—HindIII fragment was subcloned into pACYC177, and sequenced. A large open reading frame was identified, and subsequently found to contain approximately 2 kb of the putative tbpA gene. The remaining 1 kb of the tbpA gene was obtained by subcloning an adjacent downstream HindIII—HindIII fragment into vector pACYC177. The nucleotide sequence of the tbpA gene from *M. catarrhalis* 4223 (SEQ ID No: 1), and the deduced amino acid sequence (SEQ ID No: 9) are shown in FIG. 5.

Chromosomal DNA from *M. catarrhalis* strain Q8 was digested with Sau3A I and 15–23 kb fragments were ligated with BamH I arms of EMBL3. A high titre library was generated in *E. coli* LE392 cells and was screened using oligonucleotide probes based on the 4223 tbpA sequence. Phage DNA was prepared and restriction enzyme analysis revealed that inserts of about 13–15 kb had been cloned. Phage clone SLRD-A was used to subclone fragments for sequence analysis. A cloning vector (pSKMA) was generated to facilitate cloning of the fragments and plasmids pSLRD1, psLRD2, pSLRD3, and pSLRD4 were generated which contain all of tbpA and most of tbpB. The nucleotide (SEQ ID No: 5 and 6) and deduced amino acid sequence (SEQ ID No: 11—full length, SEQ ID No: 12—mature protein) of the tbpA gene from strain Q8 are shown in FIG. 9.

The deduced amino acid sequence for the Tbp1 protein encoded by the tbpA gene was found to share some homology with the amino acid sequences encoded by genes from a number of Neissaria and Haemophilus species (FIG. 10; SEQ ID Nos: 15, 16, 17 and 18).

Prior to the present discovery, tbpA genes identified in species of Neisseria, Haemophilus, and Actinobacillus have been found to be preceded by a tbpB gene with several conserved regions. The two genes typically are separated by a short intergenic sequence. However, a tbpB gene was not found upstream of the tbpA gene in *M. catarrhalis* 4223. In order to localize the tbpB gene within the 13.2 kb insert of clone LEM3-24, a denerate oligonucleotide probe was synthesized based upon an amino acid sequence EGGFYGP (SEQ ID No: 23), conserved among Tbp2 proteins of several species. The oligonucleotide was labelled and used to probe a Southern blot containing different restriction endonuclease fragments of clone LEM3-24. The probe hybridized to a 5.5 kb NheI-SalI fragment, which subsequently was subcloned into pBR328, and sequenced. The fragment contained most of the putative tbpB gene, with the exception of the promoter region. The clone LEM3-24 was sequenced to obtain the remaining upstream sequence. The tbpB gene was located approximately 3 kb downstream from the end of the tbpA gene, in contrast to the genetic organization of the tbpA and tbpB genes in Haemophilus and Neisseria. The nucleotide sequence (SEQ ID No: 3) of the tbpB gene from *M. catarrhalis* 4223 and the deduced amino acid sequence (SEQ ID No: 9) are shown in FIG. 6. Regions of homology are evident between the *M. catarrhalis* Tbp2 amino acid sequence and the Tbp2 sequences of a number of Neisseria and Haemophilus species, as shown in the comparative alignment in FIG. 11 (SEQ ID Nos: 19 to 22).

Amino acid sequencing of the N-termini and cyanogen bromide fragments of transferrin receptor from *M. catarrhalis* 4223 was undertaken. Both N-termini of Tbp1 and Tbp2 were blocked. The putative signal sequences of Tbp1 and Tbp2 are indicated by underlining in FIGS. 5 and 6 (SEQ ID Nos: 25 and 26) respectively. The deduced amino acid sequences for the N-terminal region of Tbp2 suggests a lipoprotein structure.

Results shown in Table 1 below illustrate the ability of anti-Tbp1 and anti-Tbp2 guinea pig antisera, produced by the immunization with Tbp1 or Tbp2 to lyze *M. catarrhalis*. The results show that the antisera produced by immunization with Tbp1 or Tbp2 protein isolated from *M. catarrhalis* isolate 4223 were bactericidal against a homologous non-clumping *M. catarrhalis* strain RH408 (a strain previously deposited in connection with U.S. patent application Ser. No. 08/328,589, assigned to the assignee hereof, with the American Type Culture Collection, located at 1301 Parklawn Drive, Rockville, Md. 20852, USA under the terms of the Budapest Treaty on Dec. 13, 1994 under ATCC Deposit No. 55,637) derived from isolate 4223. In addition, antisera produced by immunization with Tbp1 protein isolated from *M. catarrhalis* 4223 were bactericidal against the heterologous non-clumping strain Q8 (a gift from Dr. M. G. Bergeron, Centre Hospitalier de l'Université Laval, St. Foy, Quebec).

The ability of isolated and purified transferrin binding protein to generate bactericidal antibodies is in vivo evidence of utility of those proteins as vaccines to protect against disease caused by Moraxella.

Thus, in accordance with another aspect of the present invention, there is provided a vaccine against Moraxella comprising an immunogenically-effective amount of transferrin binding protein and a physiologically-acceptable carrier therefor. The transferrin binding protein provided herein may also be used as a carrier protein for haptens, polysaccharides or peptides to make conjugate vaccines against antigenic determinants unrelated to transferrin binding proteins.

The transferrin binding protein provided herein is useful as a diagnostic reagent, as an antigen or for the generation of anti-transferrin protein binding antibodies, antigen for vaccination against the disease caused by species of Moraxella and for detecting infection by Moraxella and other such bacteria.

In additional embodiments of the present invention, the transferrin binding protein as provided herein may be used as a carrier molecule to prepare chimeric molecules and conjugate vaccines (including glycoconjugates) against pathogenic bacteria, including encapsulated bacteria. Thus, for example, glycoconjugates of the present invention may be used to confer protection against disease and infection caused by any bacteria having polysaccharide antigens including lipooligosaccharides (LOS) and PRP. Such bacterial pathogens may include, for example, *Haemophilus influenzae, Streptococcus pneumoniae, Escherichia coli, Neisseria meningitidis, Salmonella typhi, Streptococcus mutants, Cryptococcus neoformans,* Klebsiella, *Staphylococcus aureus* and *Pseudomonas aeruginosa*. Particular antigens which can be conjugated to transferrin binding protein and methods to achieve such conjugations are described in published PCT application WO94/12641, assigned to the assignee hereof and the disclosure of which is hereby incorporated by reference thereto.

In another embodiment, the carrier function of transferrin binding protein may be used, for example, to induce an immune response against abnormal polysaccharides of tumour cells, or to produce anti-tumour antibodies that can be conjugated to chemotherapeutic or bioactive agents.

The invention extends to transferrin binding proteins from *Moraxella catarrhalis* for use as a pharmaceutical substance as an active ingredient in a vaccine against disease caused by infection with Moraxella. The invention also extends to a pharmaceutical vaccinal composition containing transferrin binding proteins from *Moraxella catarrhalis* and optionally, a pharmaceutically acceptable carrier and/or diluent.

In a further aspect the invention provides the use of transferrin binding proteins for the preparation of a pharmaceutical vaccinal composition for immunization against disease caused by infection with Moraxella.

It is clearly apparent to one skilled in the art, that the various embodiments of the present invention have many applications in the fields of vaccination, diagnosis, treatment of, for example, Moraxella infections and the generation of immunological and other diagnostic reagents. A further non-limiting discussion of such uses is further presented below.

1. Vaccine Preparation and Use

Immunogenic compositions, suitable to be used as vaccines, may be prepared from immunogenic transferrin receptor proteins, analogs and fragments thereof encoded by the nucleic acid molecules as well as the nucleic acid molecules disclosed herein. The vaccine elicits an immune response which produces antibodies, including anti-transferrin receptor antibodies and antibodies that are opsonizing or bactericidal. Should the vaccinated subject be challenged by Moraxella, the antibodies bind to the transferrin receptor and thereby prevent access of the bacteria to an iron source which is required for viability. Furthermore, opsonizing or bactericidal anti-transferrin receptor antibodies may also provide protection by alternative mechanisms.

Immunogenic compositions including vaccines may be prepared as injectables, as liquid solutions or emulsions. The transferrin receptor proteins, analogs and fragments thereof and encoding nucleic acid molecules may be mixed with pharmaceutically acceptable excipients which are compatible with the transferrin receptor proteins, fragments, analogs or nucleic acid molecules. Such excipients may include, water, saline, dextrose, glycerol, ethanol, and combinations thereof. The immunogenic compositions and vaccines may further contain auxiliary substances such as wetting or emulsifying agents, pH buffering agents, or adjuvants to enhance the effectiveness of the vaccines. Immunogenic compositions and vaccines may be administered parenterally, by injection subcutaneously, intradermally or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. The immunogenic composition may be provided in combination with a targeting molecule for delivery to specific cells of the immune system or to mucosal surfaces. Some such targeting molecules include vitamin B12 and fragments of bacterial toxins, as described in WO 92/17167 (Biotech Australia Pty. Ltd.), and monoclonal antibodies, as described in U.S. Pat. No. 5,194,254 (Barber et al). Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions may take the form of solutions, suspensions, tablets, pills, capsules, sustained release formulations or powders and contain 1 to 95% of the transferrin receptor proteins, fragments, analogs and/or nucleic acid molecules.

The vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the transferrin receptor proteins, analogs and fragments thereof and/or nucleic acid molecules. Suitable regimes for initial administration and booster doses are also variable, but may include an initial administration followed by subsequent administrations. The dosage of the vaccine may also depend on the route of administration and will vary according to the size of the host.

The nucleic acid molecules encoding the transferrin receptor of Moraxella may be used directly for immunization by administration of the DNA directly, for example, by injection for genetic immunization or by constructing a live vector such as Salmonella, BCG, adenovirus, poxvirus, vaccinia or poliovirus. A discussion of some live vectors that have been used to carry heterologous antigens to the immune system are discussed in, for example, O'Hagan (ref 22). Processes for the direct injection of DNA into test subjects for genetic immunization are described in, for example, Ulmer et al. (ref. 23).

Immunogenicity can be significantly improved if the antigens are co-administered with adjuvants, commonly used as an 0.05 to 1.0 percent solution in phosphate—buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and an HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria and mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes, if required;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. 1991 (ref. 24) reported that N-glycolipid analogs displaying structural similarities to the naturally-occurring glycolipids, such as glycophospholipids and glycoglycerolipids, are capable of eliciting strong immune responses in both herpes simplex virus vaccine and pseudorabies virus vaccine. Some glycolipids have been sythesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. 1990, (ref. 25) reported that octadecyl esters of aromatic amino acids complexed with a recombinant hepatitis B surface antigen, enhanced the host immune responses against hepatitis B virus.

2. Immunoassays

The transferrin receptor proteins, analogs and/or fragments thereof of the present invention are useful as immunogens, as antigens in immunoassays including enzyme-linked immunosorbent assays (ELISA), RIAs and other non-enzyme linked antibody binding assays or procedures known in the art for the detection of anti-Moraxella, tarnsferrin receptor protein antibodies. In ELISA assays, the transferrin receptor protein, analogs and/or fragments corresponding to portions of TfR protein, are immobilized onto a selected surface, for example, a surface capable of binding proteins or peptides such as the wells of a polystyrene microtiter plate. After washing to remove incompletely adsorbed transferrin receptor, analogs and/or fragments, a non-specific protein such as a solution of bovine serum albumin (BSA) or casein that is known to be antigenically neutral with regard to the test sample may be bound to the selected surface. This allows for blocking of non-specific adsorption sites on the immobilizing surface and thus reduces the background caused by non-specific bindings of antisera onto the surface.

The immobilizing surface is then contacted with a sample, such as clinical or biological materials, to be tested in a manner conducive to immune complex (antigen/antibody) formation. This procedure may include diluting the sample with diluents, such as BSA, bovine gamma globulin (BGG) and/or phosphate buffered saline (PBS)/Tween. The sample is then allowed to incubate for from 2 to 4 hours, at temperatures such as of the order of 25° to 37° C. Following incubation, the sample-contacted surface is washed to remove non-immunocomplexed material. The washing procedure may include washing with a solution such as PBS/Tween or a borate buffer.

Following formation of specific immunocomplexes between the test sample and the bound transferrin receptor protein, analogs and/or fragments and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a color development upon incubating with an appropriate chromogenic substrate. Quantification may then achieved by measuring the degree of color generation using, for example, a spectrophotometer.

3. Use of Sequences as Hybridization Probes

The nucleotide sequences of the present invention, comprising the sequence of the transferrin receptor gene, now allow for the identification and cloning of the transferrin receptor genes for many species of Moraxella.

The nucleotide sequences comprising the sequence of the transferrin receptor genes of the present invention are useful for their ability to selectively form duplex molecules with complementary stretches of other TfR genes. Depending on the application, a variety of hybridization conditions may be employed to achieve varying degrees of selectivity of the probe toward the other TfR genes. For a high degree of selectivity, relatively stringent conditions are used to form the duplexes, such as low salt and/or high temperature conditions, such as provided by 0.02 M to 0.15 M NaCl at temperatures of between about 50° C. to 70° C. For some applications, less stringent hybridization conditions are required such as 0.15 M to 0.9 M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results. In general, convenient hybridization temperature in the presence of 50% formamide are: 42° C. for a probe which is 95 to 100% homologous to the target fragment, 37° C. for 90 to 95% homology and 32° C. for 85 to 90% homology.

In a clinical diagnostic embodiment, the nucleic acid sequences of the TfR genes of the present invention may be used in combination with an appropriate means, such as a label, for determining hybridization. A wide variety of appropriate indicator means are known in the art, including radioactive, enzymatic or other ligands, such as avidin/biotin and digoxigenin-labelling, which are capable of providing a detectable signal. In some diagnostic embodiments, an enzyme tag such as urease, alkaline phosphatase or peroxidase, instead of a radioactive tag may be used. In the case of enzyme tags, colorimetric indicator substrates are known which can be employed to provide a means visible to the human eye or spectrophotometrically, to identify specific hybridization with samples containing TfR gene sequences.

The nucleic acid sequences of TfR genes of the present invention are useful as hybridization probes in solution hybridizations and in embodiments employing solid-phase procedures. In embodiments involving solid-phase procedures, the test DNA (or RNA) from samples, such as clinical samples, including exudates, body fluids (e.g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the TfR genes or fragments thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. It is preferred to select nucleic acid sequence portions which are conserved among species of Moraxella. The selected probe may be at least 18 bp and may be in the range of about 30 to 90 bp.

4. Expression of the Transferrin Receptor Genes

Plasmid vectors containing replicon and control sequences which are derived from species compatible with the host cell may be used for the expression of the transferrin receptor genes in expression systems. The vector ordinarily carries a replication site, as well as marking sequences which are capable of providing phenotypic selection in transformed cells. For example, E. coli may be transformed using pBR322 which contains genes for ampicillin and tetracycline resistance and thus provides easy means for identifying transformed cells. The pBR322 plasmid, or other microbial plasmid or phage, must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as E. coli LE392.

Promoters commonly used in recombinant DNA construction include the β-lactamase (penicillinase) and lactose promoter systems and other microbial promoters, such as the T7 promoter system as described in U.S. Pat. No. 4,952,496. Details concerning the nucleotide sequences of promoters are known, enabling a skilled worker to ligate them functionally with genes. The particular promoter used will generally be a matter of choice depending upon the desired results. Hosts that are appropriate for expression of the transferrin receptor genes, fragments, analogs or variants thereof, may include E. coli, Bacillus species, Haemophilus, fungi, yeast, Moraxella, Bordetella, or the baculovirus expression system may be used.

In accordance with this invention, it is preferred to make the transferring receptor protein, fragment or analog thereof, by recombinant methods, particularly when the naturally occurring TfR protein as purified from a culture of a species of Moraxella may include trace amounts of toxic materials or other contaminants. This problem can be avoided by using recombinantly produced TfR protein in heterologous systems which can be isolated from the host in a manner to minimize contaminants in the purified material. Particularly desirable hosts for expression in this regard include Gram positive bacteria which do not have LPS and are, therefore, endotoxin free. Such hosts include species of Bacillus and may be particularly useful for the production of non-pyrogenic transferring receptor, fragments or analogs thereof. Furthermore, recombinant methods of production permit the manufacture of Tbp1 or Tbp2 or analogs or fragments thereof separate from one another which is distinct from the normal combined proteins present in Moraxella.

Biological Deposits

Certain vectors that contain at least a portion coding for a transferrin receptor protein from strains of *Moraxella catarrhalis* strain 4223 and Q8 and a strain of *M. catarrhalis* RH408 that are described and referred to herein have been deposited with the American Type Culture Collection (ATCC) located at 12301 Parklawn Drive, Rockville, Md., USA, pursuant to the Budapest Treaty and prior to the filing of this application. Samples of the deposited vectors and bacterial strain will become available to the public upon grant of a patent based upon this United States patent application. The invention described and claimed herein is not to be limited in scope by the biological materials deposited, since the deposited embodiment is intended only as an illustration of the invention. Any equivalent or similar vectors or strains that encode similar or equivalent antigens as described in this application are within the scope of the invention.

| Deposit Summary | | |
| --- | --- | --- |
| Deposit | ATCC Designation | Date Deposited |
| Phage LEM3-24 | 97,381 | December 4, 1995 |
| Phage SLRD-A | 97,380 | December 4, 1995 |
| Plasmid pLEM29 | 97,461 | March 8, 1996 |
| Strain RH408 | 55,637 | December 9, 1994 |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry and immunology used but not explicitly described in this disclosure and these Examples are amply reported in the scientific literature and are well within the ability of those skilled in the art.

Example 1

This Example illustrates the preparation and immunization of guinea pigs with Tbp1 and Tbp2 proteins from *M. catarrhalis*.

Tbp1 and Tbp2 proteins were obtained as follows:

Iron-starved crude total membrane preparations were diluted to 4 mg protein/ml in 50 mM Tris.HCl-1M NaCl, pH 8, in a total volume of 384 ml. Membranes were solubilized by the addition of 8 ml each of 0.5M EDTA and 30% sarkosyl; samples were incubated for 2 hours at room temperature, with gentle agitation. Solubilized membranes were centrifuged at 10K rpm for 20 min. 15 ml of apo-hTf-Sepharose 4B were added to the supernatant, and incubated for 2 hours at room temperature, with gentle shaking. The mixture was added into a column. The column was washed with 50 ml of 50 mM Tris.HCl-1 M NaCl-250 mM guanidine hydrochloride, to remove contaminating proteins. Tbp2 was eluted from the column by the addition of 100 ml of 1.5M guanidine hydrochloride; Tbp1 was eluted by the addition of 100 ml of 3M guanidine hydrochloride. The first 20 ml fractions were dialyzed against 3 changes of 50 mM Tris.HCl, pH 8.0. Samples were stored at −20° C., or dialyzed against ammonium bicarbonate and lyophilized.

Guinea pigs (Charles River) were immunized intramuscularly on day +1 with a 10 μg dose of Tbp1 or Tbp2 emulsified in complete Freund's adjuvant. Animals were boosted on day +14 and +29 with the same dose of protein emulsified in incomplete Freund's adjuvant. Blood samples were taken on day +42, and sera were used for analysis of bactericidal antibody activity. In addition, all antisera were assessed by immunoblot analysis for reactivity with *M. catarrhalis* 4223 proteins.

The bactericidal antibody activity of guinea pig anti-*M. catarrhalis* 4223 Tbp1 or Tbp2 antisera was determined as follows. A non-clumping *M. catarrhalis* strain RH408, derived from isolate 4223, was inoculated into 20 ml of BHI, and grown for 18 hr at 37° C., shaking at 170 rpm. One ml of this culture was used to inoculate 20 ml of BHI supplemented with 25 mM ethylenediamine-dihydroxyphenylacetic acid (EDDA; Sigma). The culture was grown to an $OD_{578}$ of 0.5. The cells were diluted 1:200,000 in 140 mM NaCl, 93 mM $NaHCO_3$, 2 mM Na barbiturate, 4 mM barbituric acid, 0.5 mM $MgCl_2.6H_2O$, 0.4 mM $CaCl_2.2H_2O$, pH 7.6 (Veronal buffer), containing 0.1% bovine serum albumin (VBS) and placed on ice. Guinea pig anti-*M. catarrhalis* 4223 Tbp1 or Tbp2 antisera, along with prebleed control antisera, were heated to 56° C. for 30 min. to inactivate endogenous complement. Serial twofold dilutions of each antisera in VBS were added to the wells of a 96-well Nunclon microtitre plate (Nunc, Roskilde, Denmark). Dilutions started at 1:8, and were prepared to a final volume of 25 μL in each well. 25 μL of diluted bacterial cells were added to each of the wells. A guinea pig complement (Biowhittaker, Walkersville, Md.) was diluted 1:10 in VBS, and 25 μL portions were added to each well. The plates were incubated at 37° C. for 60 min, gently shaking at 70 rpm on a rotary platform. 50 μL of each reaction mixture were plated onto Mueller Hinton (Becton-Dickinson, Cockeysville, Md.) agar plates. The plates were incubated at 37° C. for 72 hr and the number of colonies per plate were counted. Bactericidal titres were assessed as the reciprocal of the highest dilution of antiserum capable of killing greater than 50% of bacteria compared with controls containing pre-immune era. Results shown in Table 1 below illustrate the ability of the anti-Tbp1 and anti-Tbp2 guinea pig antisera to lyze *M. catarrhalis*.

Example 2

This Example illustrates the preparation of chromosomal DNA from *M. catarrhalis* strains 4223 and Q8.

*M. catarrhalis* isolate 4223 was inoculated into 100 ml of BHI broth, and incubated for 18 hr at 37° C. with shaking. The cells were harvested by centrifugation at 10,000×g for 20 min. The pellet was used for extraction of *M. catarrhalis* 4223 chromosomal DNA.

The cell pellet was resuspended in 20 ml of 10 mM Tris-HCl (pH 7.5)-1.0 mM EDTA (TE). Pronase and SDS were added to final concentrations of 500 μg/ml and 1.0%, respectively, and the suspension was incubated at 37° C. for 2 hr. After several sequential extractions with phenol, phenol:chloroform (1:1), and chloroform:isoamyl alcohol (24:1), the aqueous extract was dialysed, at 4° C., against 1.0 M NaCl for 4 hr, and against TE (pH 7.5) for a further 48 hr with three buffer changes. Two volumes of ethanol were added to the dialysate, and the DNA was spooled onto a glass rod. The DNA was allowed to air-dry, and was dissolved in 3.0 ml of water. Concentration was estimated, by UV spectrophotometry, to be about 290 μg/ml.

*M. catarrhalis* strain Q8 was grown in BHI broth as described in Example 1. Cells were pelleted from 50 ml of culture by centrifugation at 5000 rpm for 20 minutes, at 4° C. The cell pellet was resuspended in 10 ml of TE (10 mM Tris-HCl, 1 mM EDTA, pH 7.5) and proteinase K and SDS were added to final concentrations of 500 μg/ml and 1%, respectively. The sample was incubated at 37° C. for 4 hours until a clear lysate was obtained. The lysate was extracted twice with Tris-saturated phenol/chloroform (1:1), and twice with chloroform. The final aqueous phase was dialysed for 24 hours against 2×1000 ml of 1 M NaCl at 4° C., changing the buffer once, and for 24 hours against 2×1000 ml of TE at 4° C., changing the buffer once. The final dialysate was precipitated with two volume of 100% ethanol. The DNA was spooled, dried and resuspended in 5 to 10 ml of TE buffer.

Example 3

This Example illustrates the construction of *M. catarrhalis* chromosomal libraries in EMBL3.

A series of Sau3A restriction digest of chromosomal DNA, in final volume of 10 μL each, were carried out in order to optimize the conditions necessary to generate maximal amounts of restriction fragments within a 15 to 23 kb size range. Using the optimized digestion conditions, a large-scale digestion was set up in a 100 μL volume, containing the following: 50 μL of chromosomal DNA (290 μg/ml), 33 μL water, 10 μL 10× Sau3A buffer (New England Biolabs), 1.0 μL BSA (10 mg/ml, New England Biolabs), and 6.3 μL Sau3A (0.04 U/μL). Following a 15 min. incubation at 37° C., the digestion was terminated by the addition of 10 μL of 100 mM Tris-HCl (pH 8.0)-10 mM EDTA-0.1% bromophenol blue-50% glycerol (loading buffer). Digested DNA was electrophoresed through a 0.5% agarose gel in 40 mM Tris acetate-2 mM $Na_2EDTA.2H_2O$ (pH 8.5) (TAE buffer) at 50 V for 6 hr. The region containing restriction fragments within a 15 to 23 kb molecular size range was excised from the gel, and placed into dialysis tubing containing 3.0 ml of TAE buffer. DNA was electroeluted from the gel fragment by applying a field strength of 1.0 V/cm for 18 hr. Electroeluted DNA was extracted once each with phenol and phenol:chloroform (1:1), and precipitated with ethanol. The dried DNA was dissolved in 5.0 μL water.

Size-fractionated chromosomal DNA was ligated with BamHI-digested EMBL3 arms (Promega), using T4 DNA ligase in a final volume of 9 μL. The entire ligation mixture was packaged into lambda phage using a commercial packaging kit (Amersham), following manufacturer's instructions.

The packaged DNA library was amplified on solid media. 0.1 ml aliquots of *Escherichia coli* strain NM539 in 10 mM MgSO$_4$ (OD$_{260}$=0.5) were incubated at 37° C. for 15 min. with 15 to 25 μL of the packaged DNA library. Samples were mixed with 3 ml of 0.6% agarose containing 1.0% BBL trypticase peptone-0.5% NaCl (BBL top agarose), and mixtures were plated onto 1.5% agar plates containing 1.0% BBL trypticase peptone-0.5% NaCl, and incubated at 37° C. for 18 hr. 3 ml quantities of 50 mM Tris-HCl (pH 7.5)-8 mM magnesium sulfate heptahydrate-100 mM NaCl-0.01% (w/v) gelatin (SM buffer) were added to each plate, and plates were left at 4° C. for 7 hr. SM buffer containing phage was collected from the plates, pooled together, and stored in a screwcap tube at 4° C., with chloroform.

Chromosomal DNA from *M. catarrhalis* strain Q8 was digested with Sau3A I (0.1 unit/30 μg DNA) at 37° C. for 30 minutes and size-fractionated on a 0.6% low melting point agarose gel. DNA fragments of 15–23 kb were excised and the DNA was electroeluted for 25 minutes in dialysis tubing containing TAE (40 mM Tris acetate pH 8.5, 2 mM EDTA) at 150 V. The DNA was extracted once with phenol/chloroform (1:1), precipitated, and resuspended in water. The DNA was ligated overnight with EMBL3 BamH I arms (Promega) and the ligation mixture was packaged using the Lambda in vitro packaging kit (Stratagene) and plated onto *E. coli* LE392 cells. The library was titrated and stored at 4° C. in the presence of 0.3% chloroform.

Example 4

This Example illustrates screening of the *M. catarrhalis* libraries.

Ten μL aliquots of phage stock from the EMBL3/4223 sample prepared in Example 3 above were combined each with 100 μL of *E. coli* strain LE392 in 10 mM MgSO$_4$ (OD$_{260}$=0.5) (plating cells), and incubated at 37° C. for 15 min. The samples were mixed with 3 ml each of BBL top agarose, and the mixtures were poured onto 1.5% agarose plates containing 1% bacto tryptone-0.5% bacto yeast extract-0.5% NaCl (LB agarose; Difco) and supplemented with 200 μM EDDA. The plates were incubated at 37° C. for 18 hr. Plaques were lifted onto nitrocellulose filters (Amersham Hybond-C Extra) using a standard protocol, and the filters were immersed into 5% bovine serum albumin (BSA: Boehringer) in 20 mM Tris-HCl (pH 7.5)-150 mM NaCl (TBS) for 30 min at room temperature, or 4° C. overnight. Filters were incubated for at least 1 hr at room temperature, or 18 hr at 4° C., in TBS containing a 1/1000 dilution of guinea pig anti-*M. catarrhalis* 4223 Tbp1 antiserum. Following four sequential 10 min. washes in TBS with 0.05% Tween 20 (TBS-Tween), filters were incubated for 30 min. at room temperature in TBS-Tween containing a 1/4000 dilution of recombinant Protein G labelled with horseradish peroxidase (rProtein G-HRP; Zymed). Filters were washed as above, and submerged into CN/DAB substrate solution (Pierce). Color development was arrested by immersing the filters into water. Positive plaques were cored from the plates, and each placed into 0.5 ml of SM buffer containing a few drops of chloroform. The screening procedure was repeated two more times, until 100% of the lifted plaques were positive using the guinea pig anti-*M. catarrhalis* 4223 Tbp1 antiserum.

The EMBL3/A8 library was plated onto LE392 cells on YT plates using 0.7% top agar in YT as overlay. Plaques were lifted onto nitrocellulose filters and the filters were probed with oligonucleotide probes labelled with $^{32}$Pα-dCTP (Random Primed DNA labeling kit, Boehringer Mannheim). The pre-hybridization was performed in sodium chloride/sodium citrate (SSC) buffer (ref. 27) at 37° C. for 1 h and the hybridization was performed at 42° C. overnight. The probes were based upon an internal sequence of 4223 tbpA:

```
              I   R   D   L   T   R   Y   D   P   G      (Seq ID No. 27)
4236-RD 5' ATTCGAGACTTAACACGCTATGACCCTGGC 3' (Seq ID No 28)
4237-RD 5' ATTCGTGATTTAACTCGCTATGACCCTGGT 3' (Seq ID No 29)
```

Putative plaques were re-plated and submitted to second and third rounds of screening using the same procedures. Phage clone SLRD-A was used to subclone the tfr genes for sequence analysis.

Example 5

This Example illustrates immunoblot analysis of the phage lysates using anti-*M. catarrhalis* 4223 Tbp1 and Tbp2 antisera.

Protein expressed by the phage eluants selected in Example 4 above were precipitated as follows. 60 μL of each phage eluant were combined with 200 μl *E. coli* LE392 plating cells, and incubated at 37° C. for 15 min. The mixture was inoculated into 10 ml of 1.0% NZamine A-0.5% NaCl-0.1% casamino acids-0.5% yeast extract-0.2% magnesium sulfate heptahydrate (NZCYM broth), supplemented with 200 mM EDDA, and grown at 37° C. for 18 hr, with shaking. DNAse was added to 1.0 ml of the culture, to a final concentration of 50 μg/ml, and the sample was incubated at 37° C. for 30 min. Trichloroacetic acid was added to a final concentration of 12.5%, and the mixture was left on ice for 15 min. Proteins were pelleted by centrifugation at 13,000×g for 10 min, and the pellet was washed with 1.0 ml of acetone. The pellet was air-dried and resuspended in 50 μL 4% SDS-20 mM Tris-HCl (pH 8.0)-0.2 mM EDTA (lysine buffer).

Following SDS-PAGE electrophoresis through an 11.5% gel, the proteins were transferred to Immobilon-P filters (Millipore) at a constant voltage of 20 V for 18 hr, in 25 mM Tris-HCl, 220 mM glycine-20% methanol (transfer buffer). Membranes were blocked in 5% BSA in TBS for 30 min. at room temperature. Blots were exposed either to guinea pig anti-*M. catarrhalis* 4223 Tbp1, or to guinea pig anti-*M. catarrhalis* 4223 Tbp2 antiserum, diluted 1/500 in TBS-Tween, for 2 hr at room temperature. Following three sequential 10 min. washes in TBS-Tween, membranes were incubated in TBS-Tween containing a 1/4000 dilution of rProtein G-HRP for 30 min. at room temperature. Membranes were washed as above, and immersed into CN/DAB substrate solution. Color development was arrested by immersing blots into water.

Three EMBL3 phage clones expressed both a 115 kDa protein which reacted with anti-Tbp1 antiserum, and an 80 kDa protein, which reacted with anti-Tbp2 antiserum on Western blots and were thus concluded to contain genes encoding the transferrin receptor proteins of *Moraxella catarrhalis*.

Example 6

This Example illustrates the subcloning of the *M. catarrhalis* 4223 Tbp1 protein gene tbpA.

Plate lysate cultures of the recombinant phage were prepared by combining phage eluant and *E. coli* LE392 plating cells, to produce confluent lysis on LB agar plates. Phage DNA was extracted from the plate lysates using a Wizard Lambda Preps DNA Purification System (Promega), according to manufacturer's instructions.

The EMBL3 clone LM3-24 was found to contain a 13.2 kb insert, flanked by two SalI sites. A probe to a tbpA gene was prepared and consisted of a 300 base pair amplified product generated by PCR using two degenerate oligonucleotide primers corresponding to an amino acid sequence of part of the Tbp1 protein (FIG. 1). The primer sequences were based upon the amino acid sequences NEVTGLG (SEQ ID NO: 13) and GAINEIE (SEQ ID NO: 14), which had been found to be conserved among the deduced amino acid sequences from several different *N. meningitidis* and *Haemophilus influenzae* tbpA genes. The amplified product was cloned into pCRII (Invitrogen, San Diego, Calif.) and sequenced. The deduced amino acid sequence shared homology with other putative amino acid sequence derived from *N. meningitidis* and *H. influenzae* tbpA genes (FIG. 10). The subclone was linearized with NotI (New England Biolabs), and labelled using a digoxigenin random-labelling kit (Boehringer Mannheim), according to manufacturer's instructions. The concentration of the probe was estimated to be 2 ng/µL.

DNA from the phage clone was digested with HindIII, AvrII, SalI/SphI, or SalI/AvrII, and electrophoresed through a 0.8% agarose gel. DNA was transferred to a nylon membrane (Genescreen Plus, Dupont) using an LKB VacuGene XL vacuum transfer apparatus (Pharmacia). Following transfer, the blot was air-dried, and pre-hybridized in 5× SSC-0.1% N-lauroylsarcosine-0.02% sodium dodecyl sulfate-1.0% blocking reagent (Boehringer Mannheim) in 10 mM maleic acid-15 mM NaCl (pH 7.5) (pre-hybridization solution). Labelled probe was added to the pre-hybridization solution to a final concentration of 6 ng/ml, and the blot was incubated in the probe solution at 42° C. for 18 hr. The blot was washed twice in 2× SSC-0.1% SDS, for 5 min. each at room temperature, then twice in 0.1× SSC-0.1% SDS for 15 min. each at 60° C. Following the washes, the membrane was equilibrated in 100 mM maleic acid-150 mM NaCl (pH 7.5) (buffer 1) for 1 min, then left in 1.0% blocking reagent (Boehringer Mannheim) in buffer 1 (buffer 2) for 60 min, at room temperature. The blot was exposed to anti-DIG-alkaline phosphatase (Boehringer Mannheim) diluted 1/5000 in buffer 2, for 30 min. at room temperature. Following two 15 min. washes in buffer 1, the blot was equilibrated in 100 mM Tris-HCl (pH 9.5), 100 mM NaCl, 50 mM MgCl₂ (buffer 3) for 2 min. The blot was wetted with Lumigen PPD substrate (Boehringer-Mannheim), diluted 1/100 in buffer 3, then wrapped in Saran wrap, and exposed to X-ray film for 30 min. The probe hybridized to a 3.8 kb HindIII-HindIII, a 2.0 kb AvrII-AvrII, and a 4.2 kb SalI-SphI fragment.

In order to subclone the 3.8 kb HindIII-HindIII fragment into pACYC177, phage DNA from the EMBL3 clone, and plasmid DNA from the vector pACYC177 (New England Biolabs), were digested with HindIII, and fractionated by electrophoresis on a 0.8% agarose gel. The 3.8 kb HindIII-HindIII phage DNA fragment , and the 3.9 kb HindIII-HindIII pACYC177 fragment, were excised from the gel and purified using a Geneclean kit (Bio 101 Inc., LaJolla, Calif.), according to manufacturer's directions. Purified insert and vector were ligated together using T4 DNA ligase (New England Biolabs), and transformed by conventional procedure into *E. coli* HB101 (Gibco BRL). A Qiagen Plasmid Midi-Kit (Qiagen) was used to extract and purify sequencing-quality DNA from one of the ampicillin-resistant/kanamycin-sensitive transformants, which was found to carry a 3.8 kb HindIII-HindIII insert. The subclone was named pLEM3. As described in Example 7, below, subsequent sequencing revealed that pLEM3 contained the first about 2.0 kb of tbpA sequence (FIGS. 2 and 5).

In order to subclone the remaining 1 kb of the tbpA gene, a 1.6 kb HindIII-HindIII fragment was subcloned into pACYC177 as described above, and transformed by electroporation into *E. coli* HB101 (Gibco BRL). A Midi-Plasmid DNA kit (Qiagen) was used to extract plasmid DNA from a putative kanamycin-sensitive transformant carrying a plasmid with a 1.6 kb HindIII-HindIII insert. The subclone was termed pLEM25. As described in Example 7 below, sequencing revealed that pLEM25 contained the remaining 1 kb of the tbpA gene (FIGS. 2 and 5).

The *M. catarrhalis* Q8 tfr genes were subcloned as follows. Phage DNA was prepared from plates. Briefly, the top agarose layer from three confluent plates was scraped into 9 ml of SM buffer (0.1 M NaCl, 0.2% MgSO₄, 50 mM Tris-HCl, pH 7.6, 0.01% gelatin) and 100 µl of chloroform was added. The mixture was vortexed for 10 sec, then incubated at room temperature for 2 h. The cell debris was removed by centrifugation at 8000 rpm for 15 min at 4° C. in an SS34 rotor (Sorvall model RC5C). The phage was pelleted by centrifugation at 35,000 rpm in a 70.1 Ti rotor at 10° C. for 2 h (Beckman model L8-80) and was resuspended in 500 µl of SM buffer. The sample was incubated at 4° C. overnight, then RNAse and DNAse were added to final concentrations of 40 µg/ml and 10 µg/ml, respectively and the mixture incubated at 37° C. for 1 h. To the mixture were added 10 µl of 0.5 M EDTA and 5 µl of 10% SDS and the sample was incubated at 6° C. for 15 min. The mixture was extracted twice with phenol/chloroform (1:1) and twice with chloroform and the DNA was precipitated by the addition of 2.5 volumes of absolute ethanol.

Figure 4:
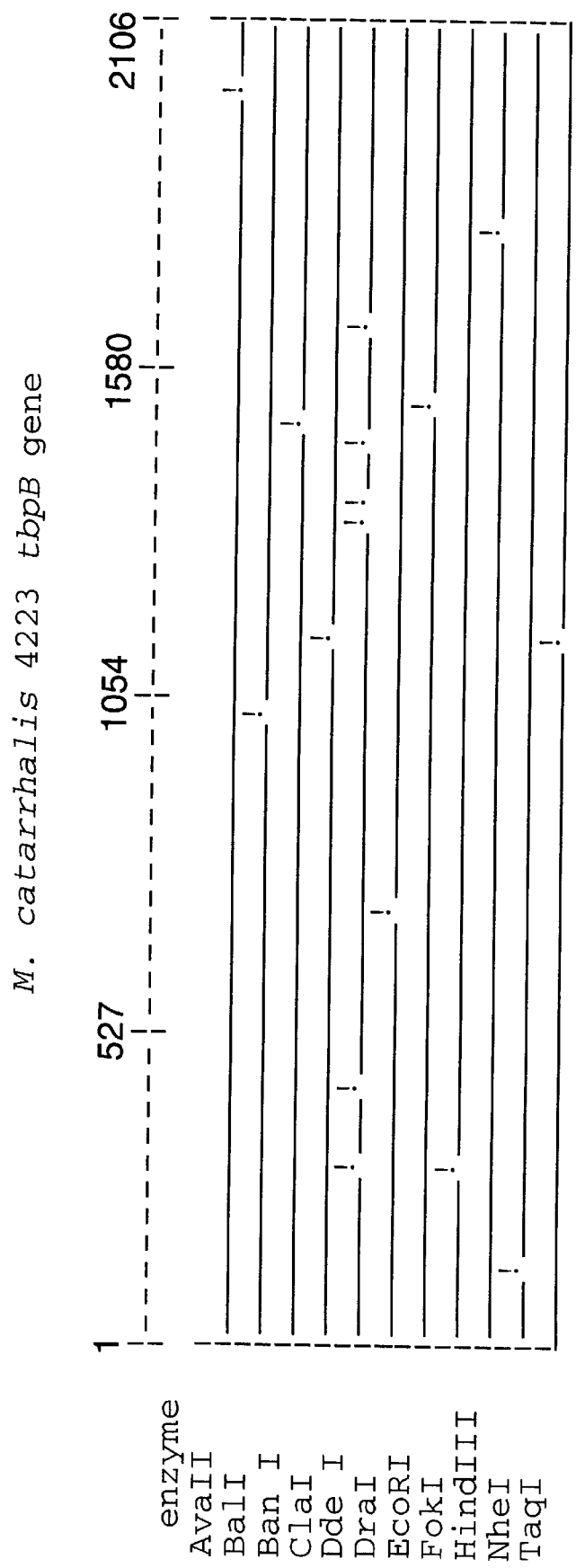
FIG. 4 shows a restriction map of the tbpB gene for M. catarrhalis 4223.

A partial restriction map was generated and fragments were subcloned using the external Sal I sites from EMBL3 and internal AvrII or EcoR I sites as indicated in FIG. 4. In order to facilitate the subcloning, plasmid pSKMA was constructed which introduces a novel multiple cloning site into pBluescript.SK (Stratagene). Oligonucleotides were used to introduce restriction sites for Mst II, Sfi I, and Avr II between the Sal I and Hind III sites of pBluescript.SK:

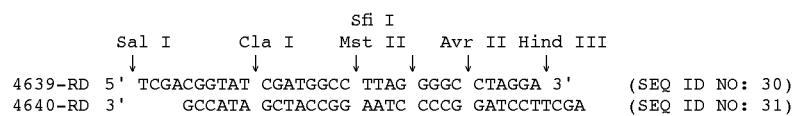

Plasmid pSLRD1 contains a −1.5 kb Sal I-Avr II fragment cloned into pSKMA; plasmids pSLRD2 and pSLRD4 contain −2 kb and 4 kb AvrII-AvrII fragments cloned into pSKMA, respectively; and plasmid pSLRD3 contains a −2.3 kb AvrII-EcoR I fragment cloned into pSKMA.

Example 7

This Example illustrates the subcloning of the *M. catarrhalis* 4223 tbpB gene.

As described above, in all Neisseriae and Haemophilus species examined prior to the present invention, tbpB genes have been found immediately upstream of the tbpA genes which share homology with the tbpA gene of *M. catarrhalis* 4223. However, the sequence upstream of *M. catarrhalis* 4223 did not correspond with other sequences encoding tbpB.

In order to localize the tbpB gene within the EMBL3 phage clone, a Southern blot was carried out using a degenerate probe from a highly conserved amino acid region within the Tbp2 protein. A degenerate oligonucleotide probe, was designed corresponding to the sequence encoding EGGFYGP (SEQ ID No: 23), which is conserved within the Tbp2 protein in a variety of Neisseriae and Haemophilus species. The probe was labelled with digoxigenin using an oligonucleotide tailing kit (Boehringer Mannheim), following the manufacturer's instructions. HindIII-digested EMBL3 clone DNA was fractionated through a 0.8% agarose gel, and transferred to a Geneclean Plus nylon membrane as described in Example 6. Following hybridization as described above, the membrane was washed twice in 2× SSC-0.1% SDS, for 5 min. each at room temperature, then twice in 0.1× SSC-0.1% SDS for 15 min. each, at 50° C. Detection of the labelled probe was carried out as described above. The probe hybridized to a 5.5 kb NheI-SalI fragment.

The 5.5 kb NheI-SalI fragment was subcloned into pBR328 as follows. LEM3-24 DNA, and pBR326 DNA, were digested with NheI-SalI, and electrophoresed through 0.8% agarose. The 5.5 kb NheI-SalI fragment, and the 4.9 kb pBR328 NheI-SalI fragments were excised from the gel, and purified using a Geneclean kit as described in Example 6. The fragments were ligated together using T4 DNA ligase, and transformed into *E. coli* DH5 using conventional procedures. A Midi-Plasmid DNA kit (Qiagen) was used to extract DNA from an ampicillin resistant/tetracycline sensitive clone containing a 5.5 kb NheI-SalI insert. This subclone was termed pLEM23. Sequencing revealed that pLEM23 contained 2 kb of the tbpB gene (FIG. 2).

Example 8

This Example illustrates sequencing of the *M. catarrhalis* tbp genes.

Both strands of the tbp genes were sequenced using an Applied Biosystems DNA sequencer. The sequence of the *M. catarrhalis* 4223 and Q8 tbpA genes are shown in FIGS. 5 and 9 respectively. A derived amino acid sequence was compared with other Tbp1 amino acid sequences, including those of *Neisseriae meningitidis, Neisseriae gonorrhoeae,* and *Haemophilus influenzae* (FIG. 10). The sequence of the *M. catarrhalis* 4223 tbpB gene is shown in FIG. 6. In order to obtain sequence from the putative beginning of the tbpB gene, sequence data were obtained directly from the clone LEM3-24 DNA. This sequence was verified by screening clone DS-1754-1. The sequence of the translated tbpB gene shared homology with deduced Tbp2 amino acid sequences of *Neisseria meningitidis, Neisseria gonorrhoeae,* and *Haemophilus influenzae* (FIG. 11).

Example 9

Figure 12A:
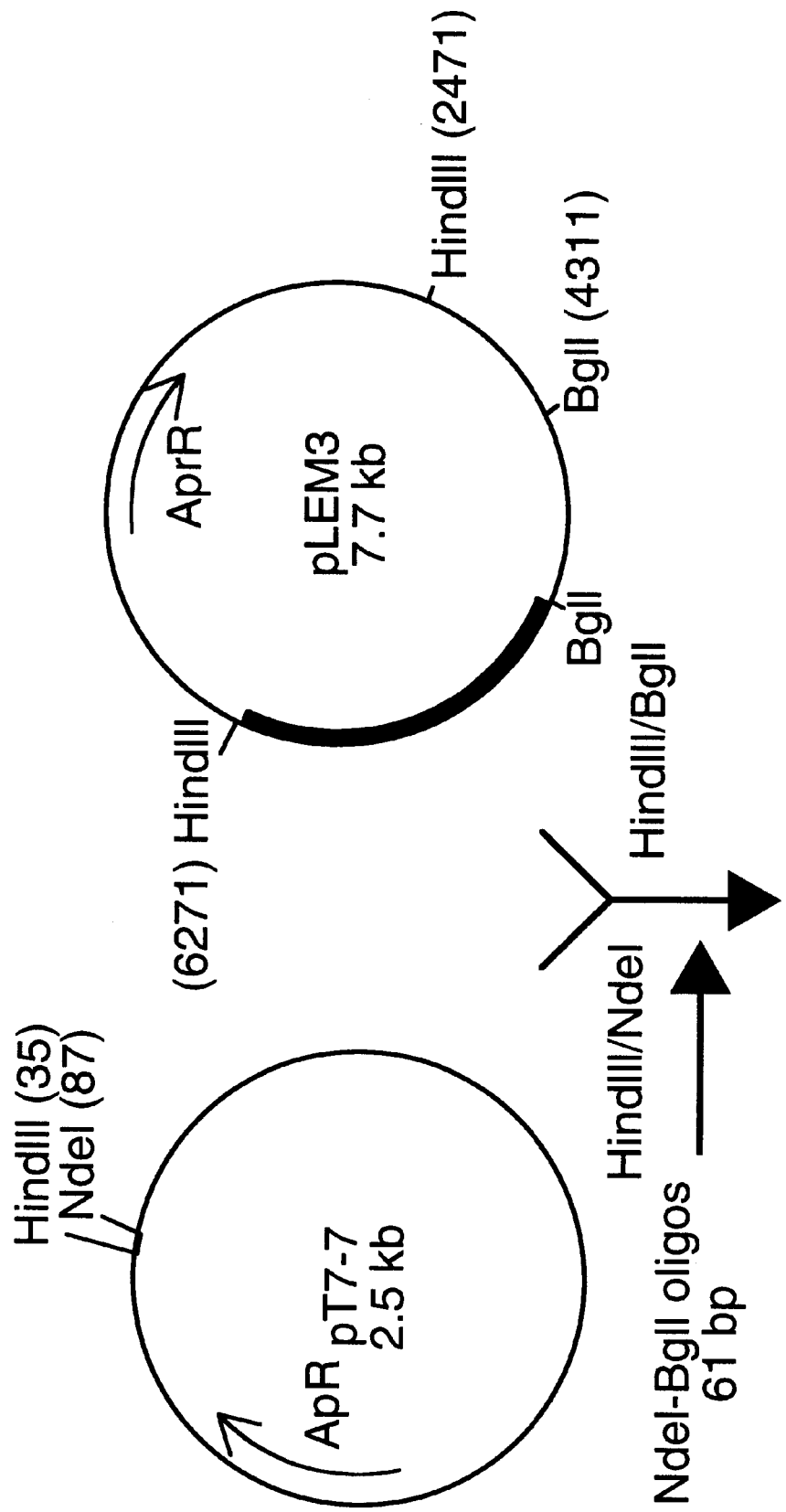
FIGS. 12A to 12B show the construction of plasmid pLEM29 for expression of recombinant Tbp1 protein from E. coli.
Figure 12B:
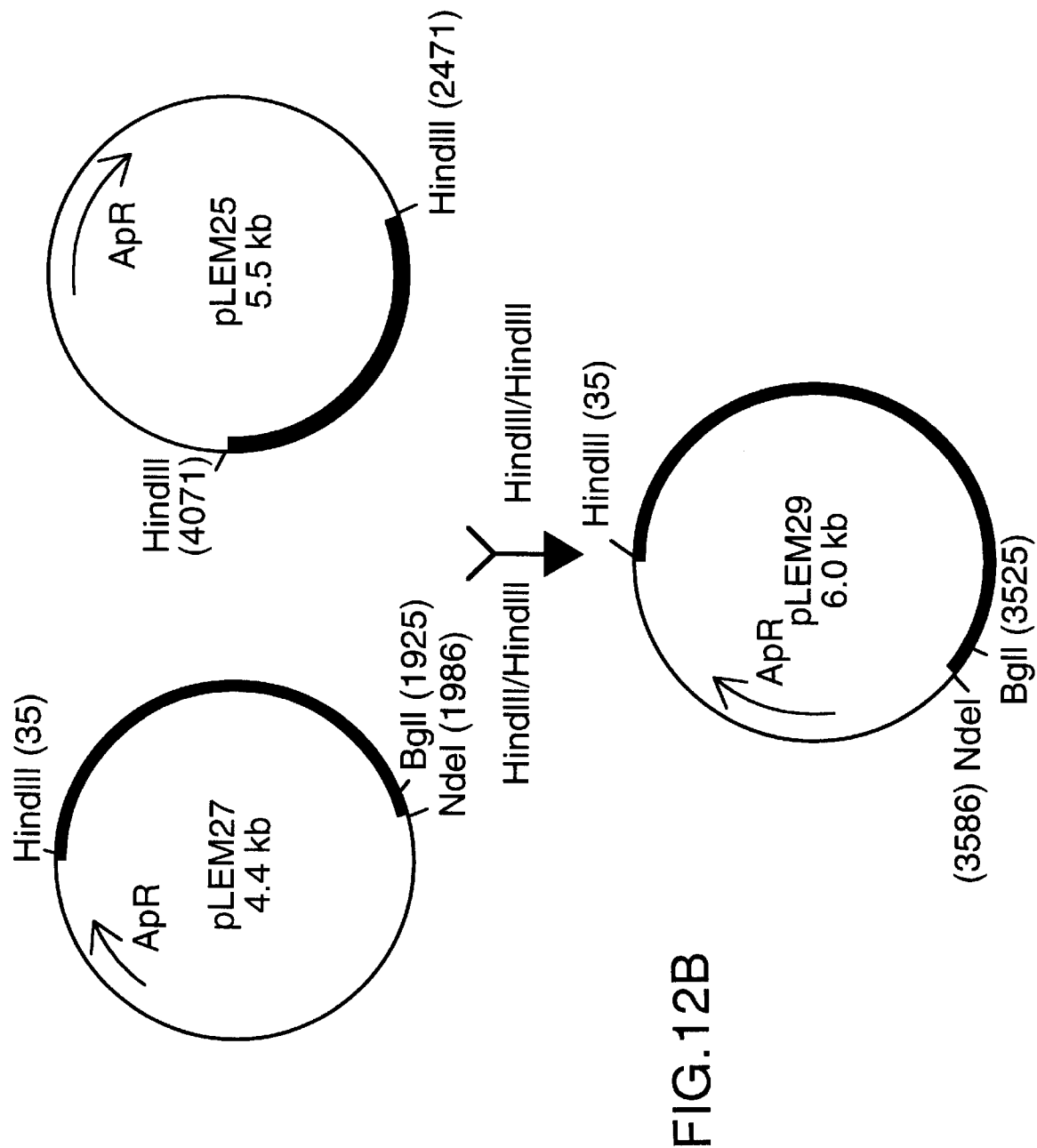

This Example illustrates the generation of an expression vector to produce recombinant Tbp1 protein. The construction scheme is shown in FIG. 12.

Figure 13:
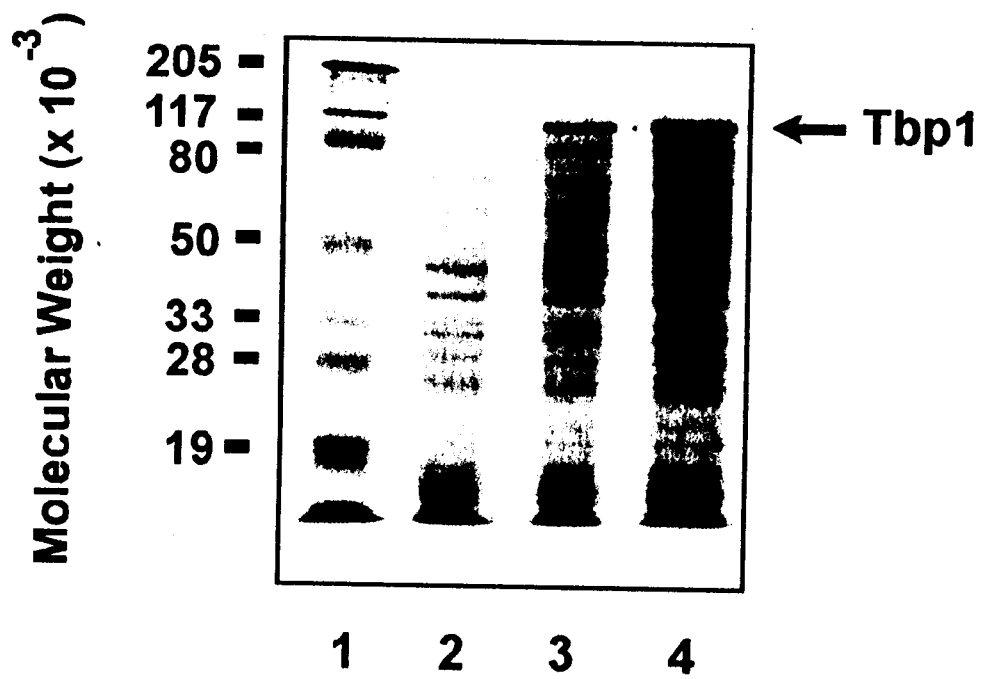
FIG. 13 shows the expression of Tbp1 protein by E. coli cells transformed with plasmid pLEM29.

Plasmid DNA from subclone pLEM3 was digested with HindIII and BglI to generate a 1.84 kb BglI-HindIII fragment, containing approximately two-thirds of the tbpA gene. BamHI was added to the digest to eliminate a comigrating 1.89 kb BglI-HindIII vector fragment. In addition, plasmid DNA from the vector pT7-7 was digested with NdeI and HindIII. In order to create the beginning of the tbpA gene, an oligonucleotide was synthesized based upon the first 61 bases of the tbpA gene to the BglI site; and NdeI site was incorporated into the 5' end. Purified insert, vector and oligonucleotide were ligated together using T4 ligase (New England Biolabs), and transformed by conventional procedure into *E. coli* DH5α. DNA was purified from one of the 4.4 kb ampicillin-resistant transformants containing correct restriction sites (pLEM27). Purified pLEM27 DNA was digested with HindIII, ligated to the 1.6 kb HindIII-HindIII insert fragment of pLEM25, and transformed into *E. coli* DH5α. DNA was purified from an ampicillin-resistant transformant containing the correct restriction sites (pLEM29), and was transformed by electroporation into electrocompetent BL21(DE3) (Novagen; Madison, Wis.) to produce *E. coli* pLEM29B-1. A single isolated transformed colony was used to inoculate 100 ml of YT broth containing 100 μg/ml ampicillin, and the culture was grown at 37° C. overnight, shaking at 200 rpm. 200 μl of the overnight culture was inoculated into 10 ml of YT broth containing 100 μg/ml ampicillin, and the culture was grown at 37° C. to an $OD_{578}$ of 0.35. The culture was induced by the addition of 30 μl of 100 mM IPTG, and the culture was grown at 37° C. for an additional 3 hours. One ml of culture was removed at the time of induction (t=0), and at t=1 and t=3 hrs. One ml samples were pelleted by centrifugation, and resuspended in 4% SDS-20 mM Tris.Cl, pH 8–200 μM EDTA (lysis buffer). Samples were fractionated on an 11.5% SDS-PAGE gel, and transferred by conventional procedures onto Immobilon filters (Amersham). Blots were developed using anti-Tbp1 (*M. catarrhalis* 4223) antiserum, diluted 1:1000, as the primary antibody, and rproteinG conjugated with horseradish peroxidase (Zymed) as the secondary antibody. A chemiluminescent substrate (Lumiglo; Kirkegaard and Perry Laboratories, Gaithersburg, Md.) was used for detection. Induced recombinant proteins were visible on the Coomassie-stained gels (FIG. 13). The anti-Tbp1 (4223) antiserum recognized the recombinant proteins on Western blots.

Example 10

This Example illustrates the generation of an expression vector to produce recombinant Tbp2.

Figure 16A:
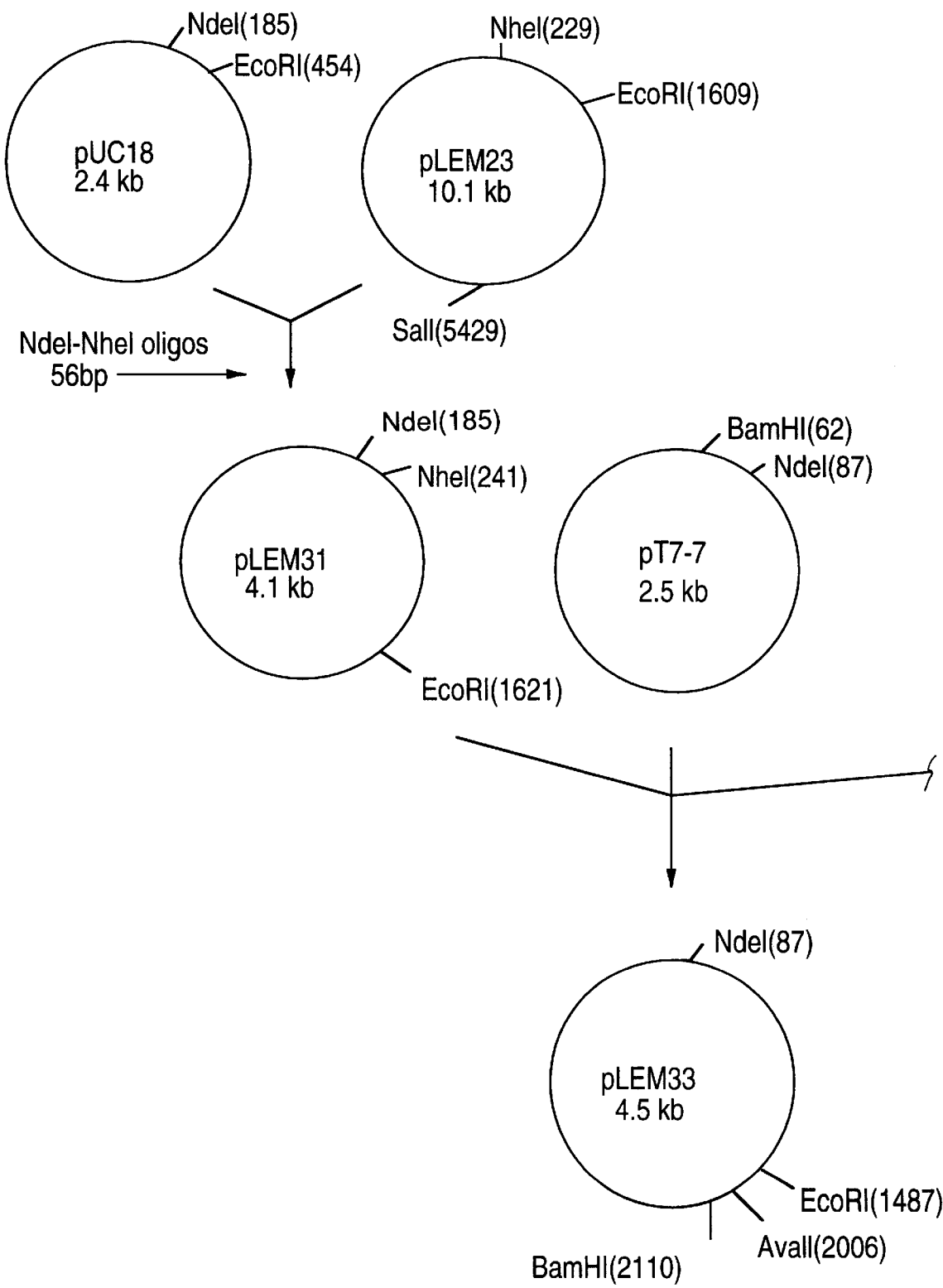
FIGS. 16A to 16B show the construction of a plasmid pLEM33 for expression of Tbp2 in E. coli.
Figure 16B:
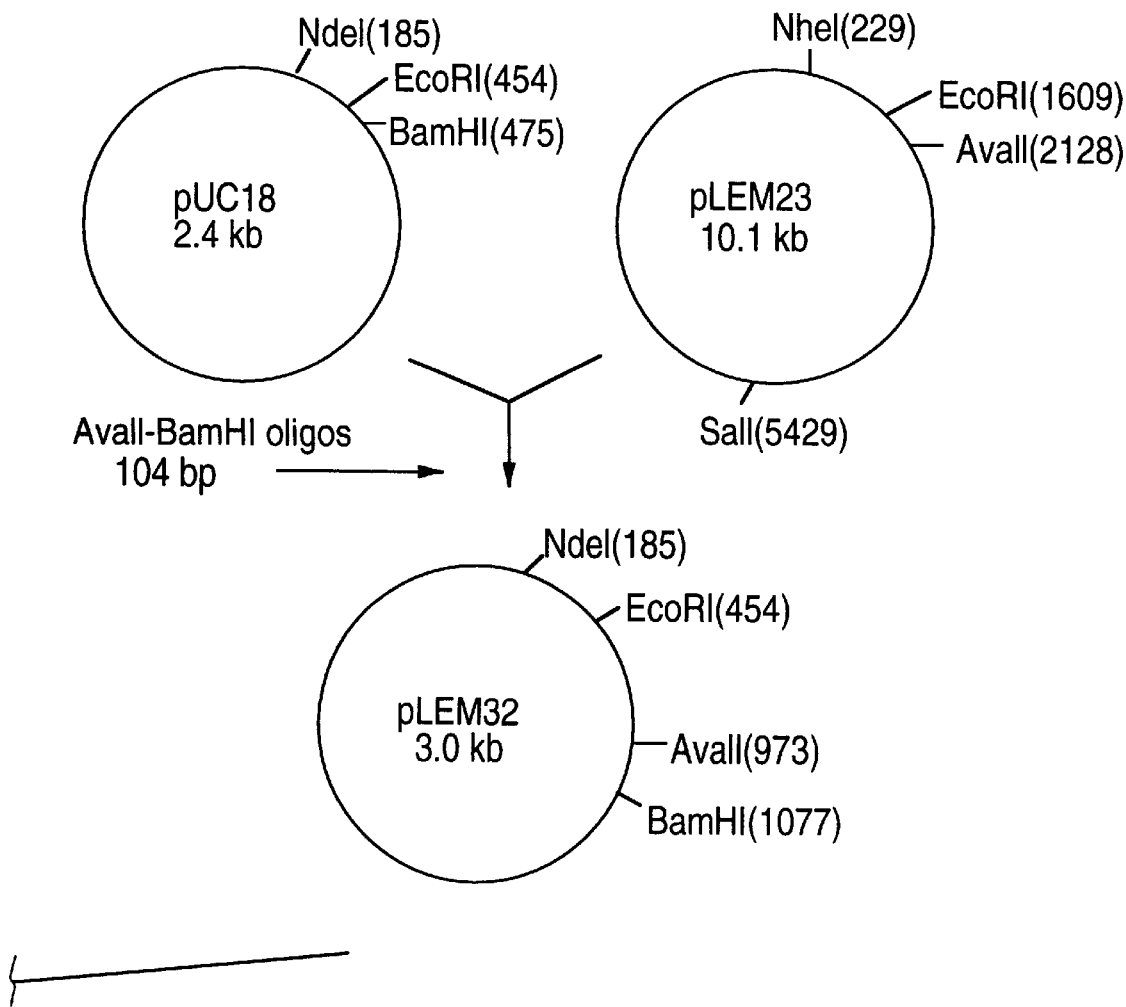

The construction scheme is shown in FIG. 16. Oligonucleotides were used to construct the first approximately 56 bases of the *M. catarrhalis* 4223 tbpB gene. An NdeI site was incorporated into the 5' end of the oligonucleotides. An NheI-EcoRI kb fragment, containing 1.38 kb of the tbpB gene from pLEM23, was ligated to the above oligonucleotides, and subsequently inserted into the NdeI-EcoRI site of pUC18 to create pLEM31. Oligonucleotides also were used to construct the last 104 bases of the tbpB gene, from the AvaII site to the end of the gene. A BamHI site was incorporated into the 3' end of the oligonucleotides. An EcoRI-AvaII fragment from pLEM23, containing 519 basepairs of the tbpB gene, was ligated with the AvaII-BamHI oligonucleotides, and subsequently ligated to pUC18 cut with EcoRI-BamHI, to create pLEM32. The 1.4 kb NdeI-EcoRI insert of pLEM31, and the 623 basepair EcoRI-BamHI insert of pLEM32 were ligated together, and inserted into pT7-7 cut with NdeI-BamHI, to create pLEM33.

DNA was purified and transformed by electroporation into electrocompetent BL21 (DE3) (Novagen; Madison, Wis.), to generate strain pLEM33B-1. Strain pLEM33B-1 was grown and induced using IPTG as described above. Expressed proteins are resolved by SDS-PAGE and transferred to membranes suitable for immunoblotting. Blots were developed using anti-Tbp2 (*M. catarrhalis* 4223) antiserum, diluted 1:1000, as the primary antibody, and rprotein G conjugated with horseradish peroxidase (Zymed) as the secondary antibody. Kirkegaard and Perry Laboratories, Gaithersbur, Md.) can be used for detection.

Example 11

This Example illustrates the extraction and purificationn of recombinant Tbp1.

Figure 14:
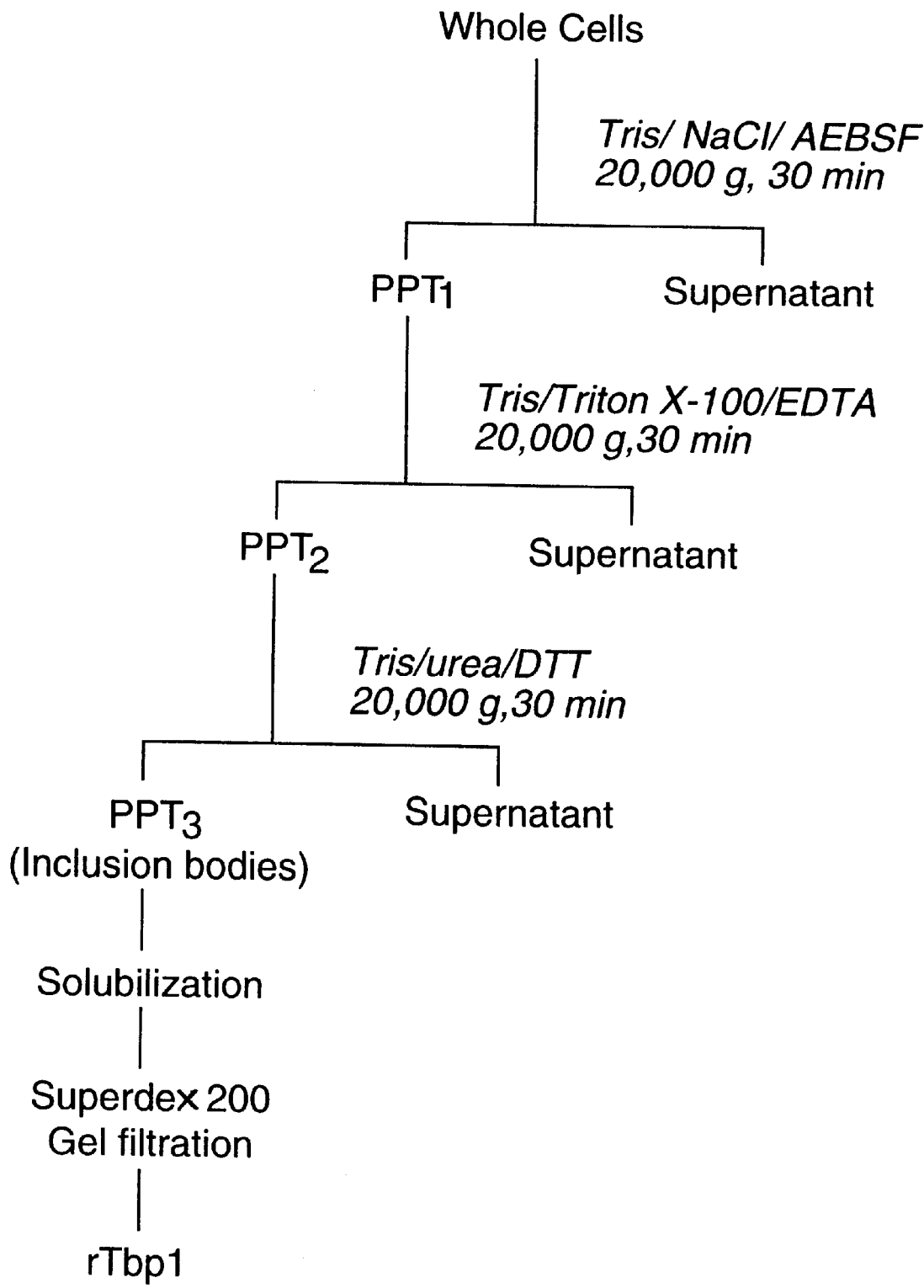
FIG. 14 shows a flow chart for purification of recombinant Tbp1 protein.
Figure 15:
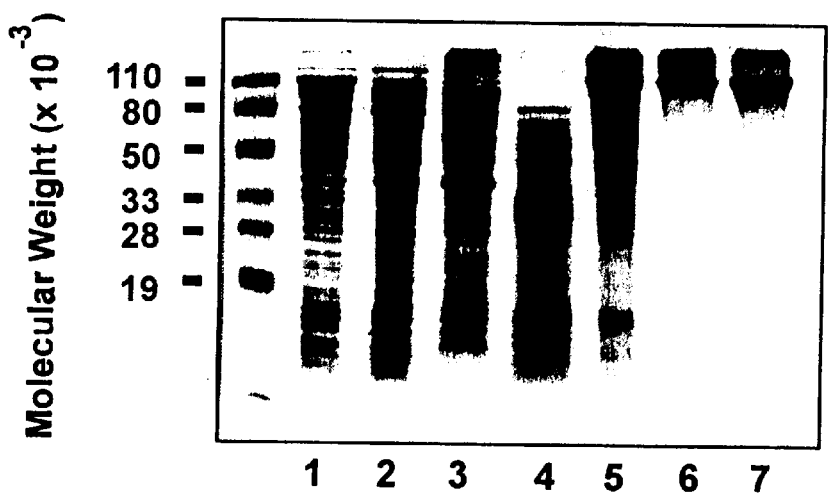
FIG. 15 shows an SDS-PAGE analysis of purified recombinant Tbp1 protein.

Recombinant Tbp1 protein was purified from *E. coli* cells expressing the tbpA gene as shown in FIG. 14.

*E. coli* cells from a 500 ml culture, prepared as described in Example 9, were resuspended in 50 ml of 50 mM Tris-HCl, pH 8.0 containing 0.1 M NaCl and 5 mM AEBSF (protease inhibitor), and disrupted by sonication (3×10 min. 70% duty circles). The extract was centrifuged at 20,000×g for 30 min. and the resultant supernatant which contained >85% of the soluble proteins from *E. coli* was discarded.

The remaining pellet (FIG. 14; PPT1) was further extracted in 50 mall of 50 mM Tris, pH 8.0 containing 0.5% Triton X-100 and 10 mM EDTA. After centrifugation at 20,000×g for 30 min., the supernatant containing residual soluble proteins and the majority of the membrane proteins was discarded.

The remaining pellet (FIG. 14, PPT2) was further extracted in 50 ml of 50 mM Tris, pH 8.0 containing 2M urea and 5 mM dithiothroitol (DTT). After centrifugation at 20,000×g for 30 min., the resultant pellet (FIG. 14, PPT3) obtained after the above extraction contained the inclusion bodies. The Tbp1 protein was solubilized in 50 mM Tris, pH 8.0, containing 6 M guanidine hydrochloride and 5 mM DTT. After centrifugation, the resultant supernatant was further purified on a Superdex 200 gel filtration column equilibrated in 50 mM Tris, pH 8.0, containing 2M guanidine hydrochloride and 5 mM DTT. The fractions were analyzed by SDS-PAGE and those containing purified Tbp1 were pooled. Triton X-100 was added to the pooled Tbp1 fraction to a final concentration of 0.1%. The fraction was then dialyzed overnight at 4° C. against 50 mM Tris, pH 8.0 and then centrifuged at 20,000×g for 30 min. The protein remained soluble under these conditions and the purified Tbp1 was stored at −20° C. The purification procedure shown in FIG. 14 produced Tbp1 protein that was at least 70% pure.

SUMMARY OF THE DISCLOSURE

In summary of this disclosure, the present invention provides purified and isolated DNA molecules containing transferrin receptor genes for *Moraxella catarrhalis*, the sequences of these transferring receptor genes, and the derived amino acid sequences thereof. The genes and DNA sequences are useful for diagnosis, immunization, and the generation of diagnostic and immunological reagents. Immunogenic compositions, including vaccines based upon expressed recombinant Tbp1 and/or Tbp2, portions thereof, or analogs thereof, can be prepared for prevention of diseases caused by Moraxella. Modifications are possible within the scope of this invention.

TABLE I

BACTERIAL ANTIBODY TITRES FOR *M. CATARRHALIS* ANTIGENS

| ANTIGEN | SOURCE OF ANTISERA[2] | BACTERIAL TITRE[3] RH408[4] | | BACTERIAL TITRE Q8[6] | |
|---|---|---|---|---|---|
| | | Pre-Immune | Post-Immune | Pre-Immune | Post-Immune |
| TBP1 | GP | <3.0 | 4.2–6.9 | <3.0 | 4.4–6.2 |
| TBP2 | GP | <3.0 | 12.0–13.6 | <3.0 | <3.0–4.0 |

[1]antigens isolated from *M. catarrhalis* 4223
[2]GP = guinea pig
[3]bacterial titres: expressed in $\log_2$ as the dilution of antiserum capable of killing 50% of cells
[4]*M. catarrhalis* RH408 is a non-clumping derivative of 4223
[5]*M. catarrhalis* Q8 is a clinical isolate which displays a non-clumping phenotype

REFERENCES

1. Brorson, J-E., A. Axelsson, and S. E. Holm. 1976. Studies on *Branhamella catarrhalis* (*Neisseria catarrhalis*) with special reference to maxillary sinusitis. Scan. J. Infect. Dis. 8:151–155.
2. Catlin, B. W., 1990. *Branhamella catarrhalis:* an organism gaining respect as a pathogen. Clin. Microbiol. Rev. 3: 293–320.
3. Hager, H., A. Verghese, S. Alvarez, and S. L. Berk. 1987. *Branhamella catarrhalis* respiratory infections. Rev. Infect. Dis. 9:1140–1149.
4. McLeod, D. T., F. Ahmad, M. J. Croughan, and M. A. Calder, 1986. Bronchopulmonary infection due to *M. catarrhalis*. Clinical features and therapeutic response. Drugs 31(Suppl.3):109–112.
5. Nicotra, B., M. Rivera, J. I. Luman, and R. J. Wallace. 1985. *Branhamella catarrhalis* as a lower respiratory tract pathogen in patients with chronic lung disease. Arch. Intern. Med. 146:890–893.
6. Ninana, G., J. Joly, and M. Kraytman. 1978. Bronchopulmonary infection due to *Branhamella catarrhalis* 11 cases assessed by transtracheal puncture. Br. Med. Jr. 1:276–278.
7. Srinivasan, G., M. J. Raff, W. C. Templeton, S. J. Givens, R. C. Graves, and J. C. Mel. 1981. *Branhamella catarrhalis* pneumonia. Report of two cases and review of the literature. Am. Rev. Respir. Dis. 123:553–555.
8. West, M., S. L. Berk, and J. K Smith. 1982. *Branhamella catarrhalis* pneumonia. South. Med. J. 75:1021–1023.
9. Christensen, J. J., and B. Bruun. 1985. Bacteremia caused by a beta-lactamase producing strain of *Branhamella catarrhalis*. Acta. Pathol. Microbiol. Immunol. Scand. Sect. B 93:273–275.
10. Craig, D. B., and P. A. Wehrle. 1983. *Branhamella catarrhalis* septic arthritis. J. Rheumatol. 10:985–986.
11. Guthrie, R., K. Bakenhaster, R. Nelson, and R. Woskobnick. 1988. *Branhamella catarrhalis* sepsis: a case report and review of the literature. J. Infect. Dis. 158:907–908.
12. Hiroshi, S., E. J. Anaissie, N. Khardori, and G. P. Bodey. 1988. *Branhamella catarrhalis* septicemia in patients with leukemia. Cancer 61:2315–2317.
13. O'Neill, J. H., and P. W. Mathieson. 1987. Meningitis due to *Branhamella catarrhalis*. Aust. N. Z. J. Med. 17:241–242.
14. Murphy, T. F. 1989. The surface of *Branhamella catarrhalis:* a systematic approach to the surface antigens of an emerging pathogen. Pediatr. Infect. Dis. J. 8:875–877.

15. Van Hare, G. F., P. A. Shurin, C. D. Marchant, N. A. Cartelli, C. E. Johnson, D. Fulton, S. Carlin, and C. H. Kim. Acute otitis media caused by *Branhamella catarrhalis:* biology and therapy. Rev. Infect. Dis. 9:16–27.
16. Jorgensen, J. H., Doern, G. V., Maher, L. A., Howell, A. W., and Redding, J. S., 1990 Antimicrobial resistance among respiratory isolates of *Haemophilus influenza, Moraxella catarrhalis,* and *Streptococcus pneumoniae* in the United States. Antibicrob. Agents Chemother. 34: 2075–2080.
17. Schryvers, A. B. and Morris, L. J. 1988 Identification and Characterization of the transferring receptor from *Neisseria meningitidis.* Mol. Microbiol. 2:281–288.
18. Lee, B. C., Schryvers, A. B. Specificity of the lactoferrin and transferring receptors in *Neisseria gonorrhoeae.* Mol. Microbiol. 1988; 2-827-9.
19. Schryvers, A. B. Characterization of the human transferrin and lactoferrin receptors in *Haemophilus influenzae.* Mol. Microbiol. 1988; 2: 467–72.
20. Schryvers, A. B. and Lee, B. C. (1988) Comparative analysis of the transferrin and lactoferrin binding proteins in the family Neisseriaceae.Can. J. Microbiol. 35, 409–415.
21. Yu, R. and Schryvers, A. B., 1993. The interaction between human transferrin and transferrin binding protein 2 from *Moraxella* (*Branhamella*) *catarrhalis* differs from that of other human pathogens. Microbiol. Pathogenesis, 15:433–445.
22. O'Hagen, 1992. Clin. Pharmokinet. 22:1
23. Ulmer et al., 1993. Curr. Opinion Invest. Drugs 2: 983–989.
24. Lockhoff, O., 1991. glycolipds as immunomoclutators: Synthesis and properties. cChem. Int. Ed. Engl. 30: 1611–1620.
25. Nixon-George, 1990. J. Immunol. 14: 4798–4802.
26. Wallace, R. J. Jr., Nash, D. R., and Steingrube, V. A. 1990. Antibiotic susceptibilites and drug resistance in *Moraxella* (*Branhaemella*) *catarrhalis.* Am. J. Med. 88 (5A): 465–505.
27. F. M. Ausubel et al., Short protocols in Molecular Biology, Greene Publishing Associates and John Wiley and Sons.

What we claim is:

1. A purified and isolated DNA molecule having a DNA sequence wherein the DNA sequence is:

(a) any one of the DNA sequences set forth in FIGS. 5, 6 or 9 (SEQ ID NOS: 1, 2, 3, 4, 5 or 6) or the complementary DNA sequence thereto; or (b) any one of the DNA sequences encoding an amino acid sequence as set out in FIGS. 5, 6 or 9 (SEQ ID NOS: 7, 8, 9, 10, 11 or 12) or the complementary DNA sequence thereto.

2. A vector adapted for transformation of a host comprising the nucleic acid molecule of claim 1.

Figure 7:
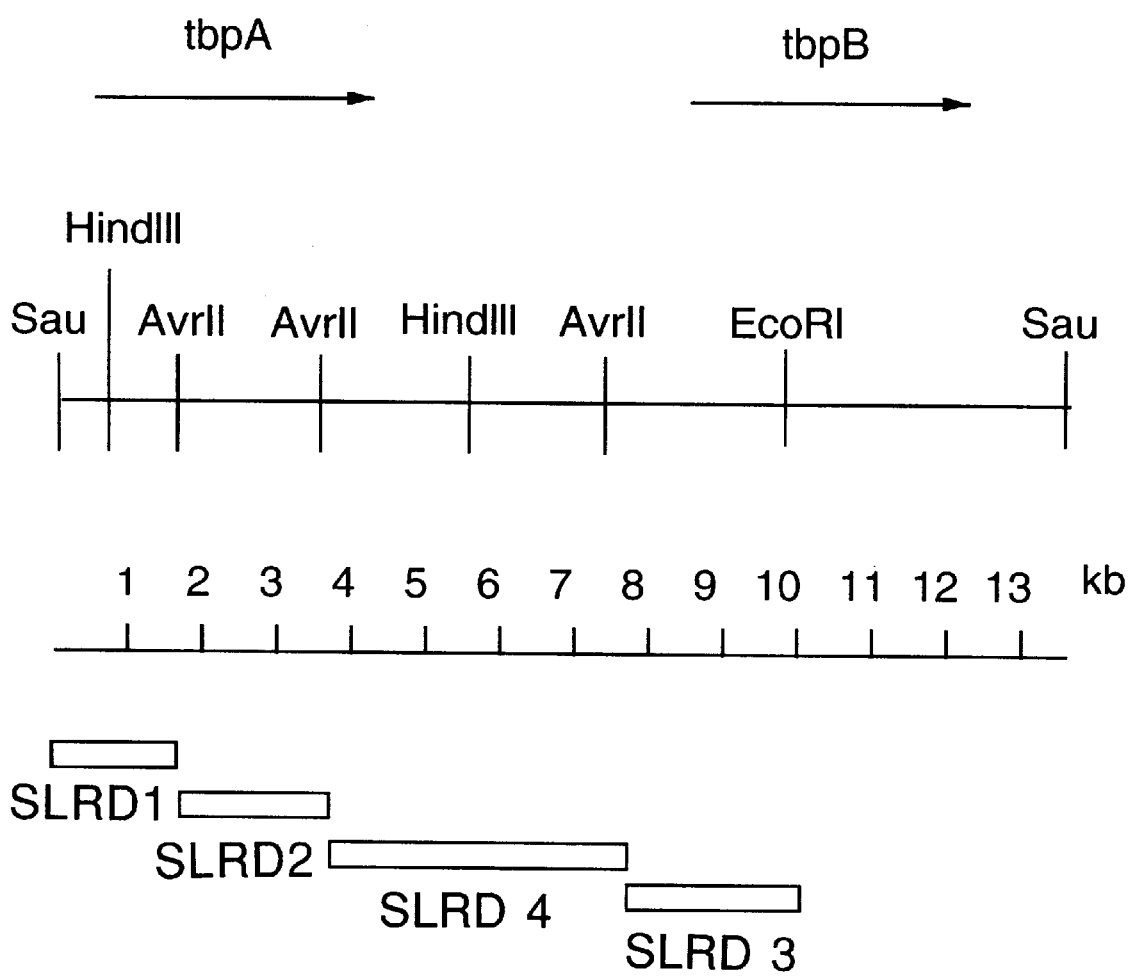
FIG. 7 shows a restriction map of clone SLRD-A containing the tbpA and tbpB genes from M. catarrhalis Q8.
Figure 8:
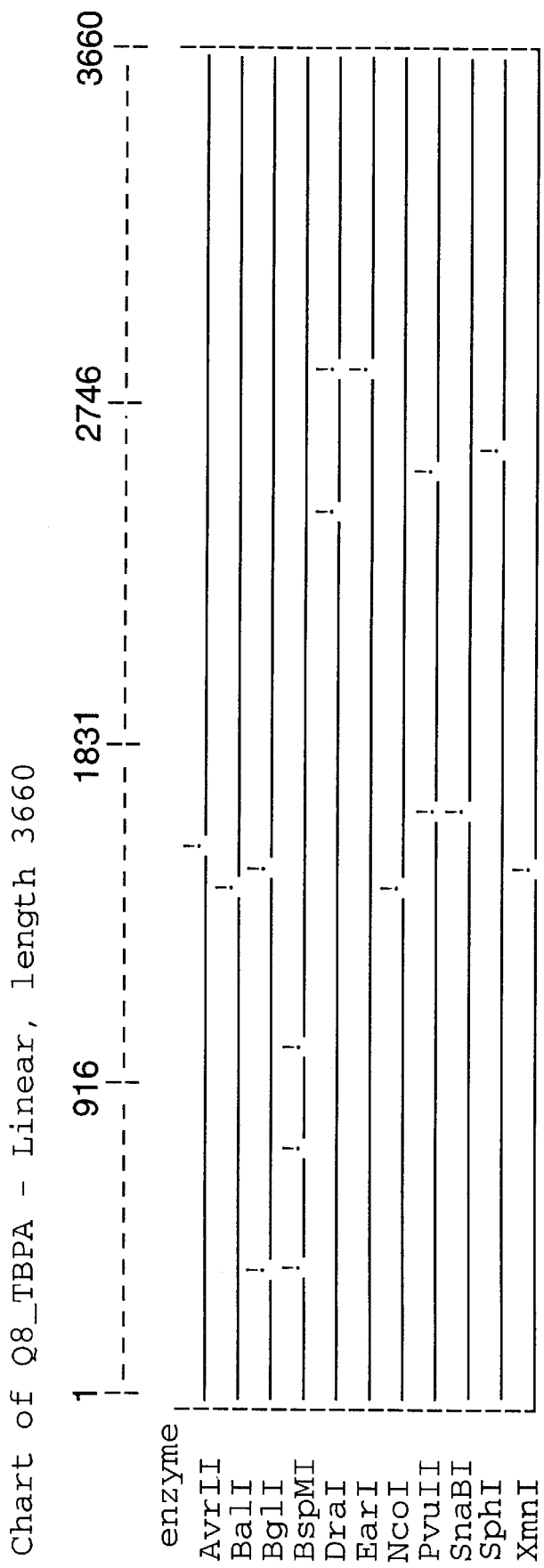
FIG. 8 shows a restriction map of the tbpA gene from M. catarrhalis Q8.

3. A vector adapted for transformation of a host comprising a nucleic acid molecule encoding a fragment of a transferrin receptor protein of Moraxella and which is a plasmid
  (a) selected from the group consisting of pLEM3, pLEM25, pLEM23, DS-1698-1 and DS-1754-1 derived from phage clone LEM3-24 having ATCC deposit number 97,381 and each containing a restriction enzyme delimited fragment of the tbpA or tbpB genes of *Moraxella catarrhalis* strain 4223 as shown in FIG. 2; or
  (b) selected from the group consisting of pSLRD2, pSLRD3 and pSLRD4 derived from phage clone SLRD-A having ATCC deposit number 97,380 and each containing a restriction enzyme delimited fragment of the tbpA or tbpB genes of *Moraxella catarrhalis* strain Q8 as shown in FIG. 7.

4. The vector of claim 2 further comprising expression means operatively coupled to the nucleic acid molecule for expression by the host of a transferrin receptor protein of a strain of Moraxella.

5. The vector of claim 4 which is pLEM-29 having ATCC deposit number 97,461 or pLEM-33.

6. A transformed host containing a vector as claimed in claim 4.

7. A method of forming a substantially pure recombinant transferring receptor protein of a strain of Moraxella, which comprises:

growing the transformed host of claim 6 to express a transferrin receptor protein of a strain of Moraxella as inclusion bodies, purifying the inclusion bodies free from cellular material and soluble proteins, solubilizing the transferring receptor protein of a strain of Moraxella free from the purified inclusion bodies, and purifying the transferring receptor protein of a strain of Moraxella free from other solubilized materials.

8. The method of claim 7 wherein said transferrin receptor protein comprises the Tbp1 protein of the strain of Moraxella alone, the Tbp2 protein of the strain of Moraxella alone or a mixture of the Tbp1 and Tbp2 proteins of the strain of Moraxella.

9. The method of claim 8 wherein said transferrin receptor protein is at least 70% pure.

10. The method of claim 9 wherein said transferrin receptor protein is at least 90% pure.

11. A diagnostic kit for determining the presence, in a sample, of nucleic acid encoding a transferring receptor protein of a strain of Moraxella, comprising:
  (a) the nucleic acid molecule of claim 1;
  (b) means for contacting the nucleic acid molecule with the sample to produce duplexes comprising the nucleic acid molecule and any said nucleic acid present in the sample and hybridizable with the nucleic acid molecule; and
  (c) means for determining production of the duplexes.

* * * * *